US009605012B2

(12) United States Patent
Garnett

(10) Patent No.: US 9,605,012 B2
(45) Date of Patent: Mar. 28, 2017

(54) PALLADIUM-RUTHENIUM-ZINC-ORGANO COMPLEXES AND METHODS FOR THEIR USE IN THE TREATMENT OF INFLAMMATORY DISEASES

(71) Applicant: GARNETT McKEEN LABORATORY, INC., East Islip, NY (US)

(72) Inventor: Merrill Garnett, East Islip, NY (US)

(73) Assignee: Garnett McKeen Laboratory, Inc., East Islip, NY (US)

( * ) Notice: Subject to any disclaimer, the term of this patent is extended or adjusted under 35 U.S.C. 154(b) by 0 days.

(21) Appl. No.: 13/792,377

(22) Filed: Mar. 11, 2013

(65) Prior Publication Data

US 2014/0199407 A1    Jul. 17, 2014

Related U.S. Application Data

(60) Provisional application No. 61/753,616, filed on Jan. 17, 2013.

(51) Int. Cl.
*C07F 19/00* (2006.01)
*C07F 15/00* (2006.01)

(52) U.S. Cl.
CPC ................ *C07F 15/0066* (2013.01)

(58) Field of Classification Search
CPC .................................................. C07F 15/0066
USPC .................... 424/502; 554/75; 514/492
See application file for complete search history.

(56) References Cited

U.S. PATENT DOCUMENTS

| | | | |
|---|---|---|---|
| 5,463,093 A | 10/1995 | Garnett | |
| 5,679,697 A | 10/1997 | Garnett | |
| 5,776,973 A | 7/1998 | Garnett | |
| 6,331,559 B1 | 12/2001 | Bingham et al. | |
| 2008/0200443 A1* | 8/2008 | Goel | 514/184 |

FOREIGN PATENT DOCUMENTS

| | | | |
|---|---|---|---|
| WO | WO 2010/111218 | * 9/2010 | ............. A01N 43/26 |
| WO | 2011/130271 A1 | 10/2011 | |
| WO | WO 2011/130271 | * 10/2011 | ........... A61K 31/385 |

OTHER PUBLICATIONS

Bonnet et al. (Organometallics 2009, 28, 2325-2333).*
Rijt et al. (Drug Discover Today, vol. 14, No. 23/24, Dec. 2009).*
Bonnet et al. "Bimetallic η6,η1 SCS- and PCP-Pincer Ruthenium Palladium Complexes: Synthesis, Structure, and Catalytic Activity", Organomatallics, 2010 pp. 1157-1167, abstract.
Wakamatsu T.H., et al., "Evaluation of lipid oxidative stress status and inflammation in atopic ocular surface disease", Molecular Vision, 2010, vol. 16, pp. 2465-2475.
Wang J. H-C, et al., "Biomedical basis for tendinopathy", Clinical Orthopaedics and Related Research, 2006, No. 443, pp. 320-332.
Yin Z., et al., "Glutathione s-transferase p elicits protection against H2 O2-induced cell death via coordinated regulation of stress kinase", Cancer Research, 2000, vol. 60, pp. 4053-4057.
Yu F., et al., "Electrochemical impedance spectroscopy to characterize inflammatory atherosclerotic plaques", Biosens Bioelectron, 2011, vol. 30, pp. 165-173.
Yu F., et al., "Electrochemical impedance spectroscopy to assess vascular oxidative stress", Ann Biomed Eng. 2011, vol. 39, pp. 287-296.
Akhavan A., et al., "Topical acne drugs and systemic exposure", Am J Clin Dermatol, 2003, vol. 4, pp. 473-492, Adis Data Information BV.
Anaya J-M, Common mechanisms of autoimmune diseases (the autoimmune tautology), Autoimmunity Reviews, 2012, vol. 11, pp. 781-784.
Bacsi A., et al., "Effect of pollen-mediated oxidative stress on immediate hypersensitivity reactions and late-phase Inflammation in allergic conjunctivitis", J Allergy Clin Immunol., 2005, vol. 116, pp. 836-843.
Caorsi R., et al., "Biologic drugs in autoinflammatory syndroms", Autoimmunity Reviews, 2012, vol. 12, pp. 81-86, Elsevier B.V.
Chen Z., et al., "Three-dimensional vortex pinning by nano-precipitates in a Sm-doped YBA2Cu3O7-x coated conductor", Superconductor Science and Technology, 2007, vol. 20, pp. 205-210, IOP Publishing.
Crescentini M., et al., "Recent trends for (Bio) Chemical Impedance Sensor Electronic Interfaces", Electroanalysis, 2012, vol. 24, pp. 563-572, Wiley-VCH Verlag GmbH & Co. KGaA, Weinheim.
Dalal A., et al., "Orthopedic implant cobalt-alloy particles produce greater toxicity and inflammatory cytokines than titanium alloy and zirconium alloy-based particles in vitro, in human osteoblasts, fibroblasts, and macrophages", J Biomed Mater Res Part A, vol. 100A, 2012, pp. 2147-2158.
Esser P.R., et al., "Contact sensitizers induce skin inflammation via ROS production and hyaluronic acid degradation", PLoS ONE, 2012, vol. 7, pp. 1-17.
Fan J., et al., "Direct evidence for catalase and peroxidase activities of ferritin-platinum nanoparticles", Biomaterials, 2011, vol. 32, pp. 1611-1618.
Fathman C.G., et al., "An array of possibilities for the study of autoimmunity", Nature, 2005, vol. 435, pp. 605-611.
Feldman M., et al., "Design of effective immunotherapy for human autoimmunity", Nature, 2005, vol. 435, pp. 312-619.
Gabbita S.P., et al., "Redox regulatory mechanisms of cellular signal transduction", Archives of Biochemistry and Biophysics, 2000, vol. 376, pp. 1-13, Academic Press.
Goldbach-Mansky R., "Immunology in clinic review series; focus on autoinflammatory diseases: update on monogenic autoinflammatory diseases: the role of interlukin (IL)-1 and an emerging role for cytokines behone IL-1", Clinical and Experimental Immunology, 2011, vol. 167, pp. 391-404.

(Continued)

*Primary Examiner* — Anna Falkowitz
(74) *Attorney, Agent, or Firm* — Chiesa Shahinian & Giantomasi PC

(57) ABSTRACT

The described invention provides organometallic complexes capable of spin transfer, comprising at least three different metals and the use of pharmaceutical compositions comprising such complexes in detoxification of reactive oxygen species in inflammatory conditions.

61 Claims, 16 Drawing Sheets

(56) References Cited

OTHER PUBLICATIONS

Goodnow C.C., et al., "Cellular and gentic mechanisms of self tolerance and autoimmunity", Nature, 2005, vol. 435, pp. 590-598.
Gross O., et al., "The inflammasome: an integrated view", Immunological Reviews, 2011, vol. 243, pp. 136-151.
Hammelmann E., et al., Noninvasive measurement of airway responsiveness in allergic mice using barometric plethysmography, Am J Respir Crit Care Med, 1997, vol. 156, pp. 7767-775.
Hayter S.M., et al., "Updated assessment of the prevalence, spectrum and case definition of autoimmune disease", Autoimmunity Reviews, 2012, vol. 11, pp. 754-765.
Kaleagasioglu F., et al., "Fluoroquinolone-induced tendinopathy: Etiology and preventive measures", Tohoku J. Exp. Med., 2012, vol. 226, pp. 251-258.
Kanta J., "The role of hydrogen peroxide and other reactive oxygen species in wound healing", ACTA MEDICA, 2011, vol. 54, pp. 97-101.
Keegan G.M., et al., "Orthopaedic metals and their potential toxicity in the arthroplasty patient" J Bone Joint Surg (BR), vol. 89, pp. 567-573, (2007).
Kloprogge J. Theo, et al., " FT-Raman and FT-IR spectroscopic study of synthetic Mg/Zn/Al-hydrotalcites", Journal of Raman Spectroscopy, 2004, vol. 35, pp. 967-974.
Kronenberg M., et al., "Regulation of immunity by self-reactive T cells", Nature, 2005, vol. 435, pp. 598-604.
Leung D. Y.M., "Atopic dermatitis: New insights and opportunities for therapeutic intervention", J Allergy Clin Immunol, 2000, vol. 105, pp. 860-876.
Iijima M.K., et al., "Exposure to ozone aggravates nasal allergy-like symptoms in guinea pigs", Toxicology Letters, 2001, vol. 123, pp. 77-85.
Longo U.G., et al.,, "Oxygen species and overuse tendionopathy in athletes", Disability and Rehabilitatio, 2008, vol. 30, pp. 1563-1571.
Malefyt R. D.W., "Interlukin-17 Kick-Starts T Helper 1 cell differentiation" Immunity, 2009, vol. 31, pp. 700-702.
Mankan A.K., et al., "Immunology in clinic review series; focus on autoinflammatory diseases: inflammasome: mechanisms of activation", Clinical and Experimental Immunology, vol. 167, pp. 369-381. (2011).
Mao X., et al., "Therapeutic potential of the proteasome inhibitor bortzomib of titanium particle-induced inflammation in a murine model" Inflammation, 2012, vol. 35, pp. 905-912.
McMillan S.J., et al., "Therapeutic administration of budesonide ameliorates allergen-induced airway remodeling", Clin Exp Allergy, 2005, vol. 35, pp. 388-396.
Moseley R., et al., "Comparison of the antioxidant properties of wound dressing materials-carboxymethylcellulose, hyaluronana benzyl ester and hyaluronan, towards polymorphonuclear leukocyte-derived reactive oxygen species", Biomaterials, 2003, vol. 24, pp. 1549-1557.
Nalawade P., et al., "Layered double hydroxides: A review", Journal of Scientific & Industrial Research, 2009, vol. 38, pp. 267-272.
Nauseef W.M., et al., "Assembly of the phagocyte NADPH oxidase", Histochem Cell Biol, 2004, pp. 122, vol. 277-291.
Nauseef W.M., "Contributions of myeloperoxidase to proinflammatory events: More than an antimicrobial system", International Journal of Hematology, 2001, vol. 74, pp. 125-133.
Nials A.T., et al., "Mouse models of allergic asthma: acute and chronic allergen challenge", Disease Models & Mechanisms, 2008, vol. 1, pp. 213-220.
Niethammer P., et al., "A tissue-scale gradient of hydrogen peroxide mediates rapid wound detection in zebrafish", Nature, 2009, vol. 459, pp. 996-999.
Ozkurede V.U., et al., "Immunology in clinic review series; focus on autoinflammatory diseases: role of inflammasomes in autoinflammatory syndromes", Clinical and Experimental Immunology, 2011, vol. 167, pp. 382-390.
Pouzaud F., et al., "Age-dependent effects on redox status, oxidative stress, mitochondrial activity and toxicity induced by flouroquinolones on primary cultures of rabbit tendon cells", Comparative Biochemistry and Physiology, Part C, 2006, vol. 143, pp. 232-241.
Rada B., et al., "Oxidative innate immune defenses by noxlduox family NADPH oxidases", NADPH Oxidases in Innate Immunity, 2008, vol. 15, pp. 164-187.
Rioux J.D., et al., "Paths to understanding the genetic basis of autoimmune disease", Nature, 2005, vol. 435, pp. 584-589.
Rojkind M., et al., "Role of hydrogen peroxide and oxidative stress in healing responses", Cell. Mol. Life Sci., 2002, vol. 59, pp. 1872-1891.
Rosenberg H.F., et al., "Inflammation", Fundamental Immunology, 1999, pp. 1051-1053, Lippincott-Raven Publishers, Philadelphia.
Schonfelder U., et al., "Influence of selected wound dressings on PMN elastase in chronic wound fluid and their antioxidative potential in vitro", Biomaterials, 2005, vol. 26, pp. 6664-6673.
Schoonbroodt S., et al., "Crucial role of amino-terminal tyrosine residue 42 and the carboxyl-terminal PEST domain of I kba in NF-kB activation bg and oxidative stress" J Immunol, 2000, vol. 164, pp. 4292-4300, Beckman Coulter Life Sciences.
Schuster-Bockler B., et al., "Chromatin organization is a major influence on regional mutation rates in human cancer cells", Nature, 2012, vol. 488, pp. 504-507.
Sen C.K., et al., "Redox signals in wound healing", Biochim Biophys Acta., 2008, vol. 1780, pp. 1348-1361.
Sharma P., et al., "Tendon injury and tendinopathy: Healing and repair", J. Bone Joint Surg. Am., 2005, vol. 87, pp. 187-202.
Swarnakar N.K., et al., "Oral bioavailability, therapeutic efficacy and reactive oxygen species scavenging properties of coenzyme Q10-loaded polymeric nanoparticles", Biomaterials, 2011, vol. 32, pp. 6860-6874.
Takeuchi O., et al, "Pattern recognition receptors and inflammation", Cell, 2010, vol. 140, pp. 805-820.
Tang D., et al., Hydrogen peroxide stimulates macrophages and monocytes to actively release HMGB1, J Leukoc Biol., 2007, vol. 81, pp. 741-747.
Tsukahara H., et al., Oxidative stress and altered antioxidant defenses in children with acute exacerbation of atopic dermatitis:, Life Sciences, 2003, vol. 72, pp. 2509-2516.

* cited by examiner

PALLADIUM-RUTHENIUM-ZINC-ORGANO COMPLEXES AND METHODS FOR THEIR USE IN THE TREATMENT OF INFLAMMATORY DISEASES

CROSS-REFERENCE TO RELATED APPLICATIONS

This application claims priority from U.S. provisional patent application Ser. No. 61/753,616, filed Jan. 17, 2013, the entire disclosure of which is incorporated herein by reference.

FIELD OF THE INVENTION

The described invention relates to organo-metallic complexes capable of charge and/or spin transfer and the use of pharmaceutical compositions comprising such complexes for the treatment of inflammatory conditions.

BACKGROUND OF THE INVENTION

Electrochemical Properties of Living Tissue

A living tissue functions as an electrical machine, and the matrix of cells comprising the tissue exhibit electrical properties including, but not limited to, the ability to conduct electricity, create electric fields, and function as electrical generators. The primary charge carriers in living organisms are negatively charged electrons, positively charged hydrogen protons, positively charged sodium, potassium, calcium and magnesium ions and negatively charged anions, particularly phosphate ions. (Reviewed in Haltiwanger, S., "The Electrical Properties of Cancer Cells," July 2010, accessed from royalrife.com/haltiwanger1).

The body uses the exterior cell membrane, and positively charged mineral ions that are maintained in different concentrations on each side of the cell membrane, to create a cell membrane potential (a voltage difference across the membrane) and a strong electrical field around the cell membrane. (As used herein the term "electrical field" refers to the effect which a charged particle or body exerts on charged particles or bodies situated in the medium surrounding it; i.e., if a negatively charged particle is placed within the electric field of a positively charged particle, there will be an attractive force, while there will be a repulsive force if the charges are alike. The electric field is perpendicular to the magnetic field). This electrical field is a readily available source of energy for cellular activities, such as membrane transport, and the generation of electrical impulses in the brain, nerves, heart and muscles. The storage of electrical charge in the membrane and the generation of an electrical field create a battery function so that the liquid crystal (meaning symmetrically packed) eletroactive intermediates and catalysts can transfer membrane charge to DNA. The body also uses the mitochondrial membrane and positively charged hydrogen ions to create a strong membrane potential across the mitochondrial membrane. Hydrogen ions are maintained in a high concentration on the outside of the mitochondrial membrane by the action of the electron transport chain (Haltiwanger, S., "The Electrical Properties of Cancer Cells," July 2010, accessed from royalrife.com/haltiwanger1).

Animal cells are organized structures with an internal architecture of cytoskeletal proteins that connects all components of the cell. Cellular components do not randomly float around in the cell but are attached to the cytoskeletal framework and the membranes. Cytoskeletal filaments and tubules form a continuous system that links the cell surface to all organelle structures including passage through the nuclear membrane to the chromosomes. The liquid crystal proteins that compose the cytoskeleton support, stabilize and connect the liquid crystal components of the cell membrane with other cell organelles. The cytoskeletal proteins have multiple roles. They serve as mechanical scaffolds that organize enzymes and water and anchor the cell to structures in the extracellular matrix (ECM) via linkages through the cell membrane, and are dynamic network structures that create a fully integrated electronic that structurally and electronically links and integrates the proteins of the extracellular matrix with the cell organelles. (Haltiwanger, S., "The Electrical Properties of Cancer Cells," July 2010, accessed from the royalrife.com/haltiwanger1).

The vascular space, filled with blood, is strictly within the confines of arteries, veins, arterioles, veinules, and capillaries. The interstitial space is designated as the cell-poor residual space beyond vascular containment and in between the capillaries and the tissue cells. These spaces create an inflammatory divide. Protective enzymes, such as peroxidases, are only present in functional concentrations in the vascular space. The interstitial space is vulnerable to metabolically produced radicals such as peroxide. Synovial space in joints contains hyaluronic acid and resembles the interstitial space Cartilage, which has a poor blood supply and contains a structural form of hyaluronic acid, also resembles the interstitial space. It is the interstitial space that undergoes allergic edema. Inflammation is usually treated with small molecules that can diffuse into the interstitial space and into sites of inflammation. The use of steroids, for example, increases the local permeability of the sites of inflammation, thereby increasing access to the vascular circulation.

The cytoskeleton is also attached through cell membrane connectors to liquid crystal protein polymers located in the external extracellular matrix (ECM) and to other cells. The liquid crystal protein polymers of the ECM are mostly composed of collagen, elastin, hylauronic acid, and interweaving glycoproteins such as fibronectin. The ECM is a transit area for the passage of nutrients from the bloodstream into the cells, for toxins released by the cells that pass through to the bloodstream, and for migrating immune cells involved in inflammatory reactions that secrete cytokines and other inflammatory mediators. (Haltiwanger, S., "The Electrical Properties of Cancer Cells," July 2010, accessed from the royalrife.com/haltiwanger1).

Biochemically, the ECM is a metabolically and electrically active space that is involved in regulating cell growth control. Cellular components of the ECM are involved in the local production of growth factors, growth inhibitors and cytokines that affect the growth and metabolic activity of tissue/organ cells. (Reichart, L. F., "Extracellular matrix molecules," In "Guidebook to the Extracellular Matrix, Anchor, and Adhesion Proteins," (ed. T. Kreis and R. Vale). Oxford, England: Oxford University Press, pgs. 335-344, 1999). Immune cells such as leukocytes, lymphocytes and macrophages that migrate into the ECM are involved in initiating the removal of damaged cells and in stimulating the growth of new cells.

Cells are electromagnetic in nature, and are capable of generating their own electromagnetic fields and of harnessing external electromagnetic energy of the right wavelength to communicate, control and drive metabolic reactions. Communications in living organisms are accomplished by chemical communication through the circulatory system and energetic communication through the nervous system. A solid state electronic communication system has also been hypothesized to operate in series and in parallel with the nervous system through the liquid crystal protein polymer connective system continuum of the cytoskeleton and extracellular matrix. It has been hypothesized that this continuum of liquid crystal connections function as electronic semiconductors and fiberoptic cables allowing the shunting of charge and associated electronic energy in and out of the cell. (Haltiwanger, S., "The Electrical Properties of Cancer Cells," July 2010, accessed from the royalrife.com/haltiwanger1).

Most molecules in the body are electrical dipoles capable of oscillations and resonance. Electric fields induce or cause alignment of dipole moments. A dipole moment is a function of polarization processes and the strength of the electric field. When biological tissue is exposed to an electric field in the right frequency and amplitude windows, a preferential alignment of dipoles becomes established. Since the cell membrane contains many dipole molecules, an applied electric field causes a preferential alignment of the dipoles. Both internally generated and externally applied electromagnetic fields can affect cell functions. (Haltiwanger, S., "The Electrical Properties of Cancer Cells," July 2010, accessed from the royalrife.com/haltiwanger1).

Electrical Properties of the Cell in Disease Repair and Healing

The body uses electricity (biocurrents) as part of its mechanism for controlling growth and repair. Some of these biocurrents travel through hydrated liquid crystal semiconducting (the term "semiconductor" refers a material whose conductivity lies between that of an electrical conductor, such as a metal, and an insulator) protein-proteoglycan (collagen-hyaluronic acid) complexes of the ECM. It has been hypothesized that biocurrents in the ECM pass through the cell membrane into the cell and electrons produced in the cell also pass out through the cell membrane. The biological liquid crystal molecules and structures such as hyaluronic acid, prothrombin, DNA, cytoskeletal proteins and cell membranes maintain both an inward and outward current. The inward current flows from the cell membrane to cell structures like mitochondria and DNA, and the outward current flows back along liquid crystal semiconducting cytoskeletal proteins through the cell membrane to the ECM. Electrical charges stored in the cell membrane (capacitance) and electrical charges of oxygen free radicals are normally transferred to DNA and are involved in DNA activation and the creation of an electrical field around DNA. DNA is very effective in transferring large amounts of electrical charge along its long axis. (Haltiwanger (2010) citing Garnett M., "First Pulse: A Personal Journey in Cancer Research," New York, N.Y.: First Pulse Projects, 1998). An alternating current oscillating circuit between the cell membrane and DNA conducted over the electronic liquid crystal network of the cell is thought to be involved in cellular processes such as gene expression. (Garnett, M. and Remo, J. L., "DNA Reductase: A Synthetic Enzyme with Opportunistic Clinical Activity Against Radiation Sickness," International Symposium on Applications of Enzymes in Chemical and Biological Defense, Orlando, Fla., May, 2001, p. 41.)

It has also been hypothesized that electrical pathways between the cell membrane and DNA are related to cell development, and use anaerobic mechanisms of ATP production. This natural electrical pathway is thought to be transiently disrupted in healthy cells that are involved in wound healing and inflammation, and permanently disrupted in cancer cells that rely on anaerobic glycolysis for energy production. (Haltiwanger (2010) citing Garnett M., "First Pulse: A Personal Journey in Cancer Research," New York, N.Y.: First Pulse Projects, 1998).

Glycoproteins secreted from the cell interior and cellular components of the ECM produce a glycocalyx that covers the cells. These glycoproteins characteristically have a negative charge. The negative charges of the ECM-glycocalyx interface help determine water balance, ion balance and osmotic balance both in the ground substance of the ECM and inside the cells. ECM proteoglycans exist in fern shapes that allow electric charges to flow, and in disorganized shapes that impair transit through the ECM of electrical currents and nutrients. These disorganized shapes occur in the presence of tissue inflammation and toxins, such as free radicals, reactive oxygen species (e.g. superoxide, peroxide, or hydroxyl ions) in the ECM. Such structures produce pockets of high electrical resistance. (Haltiwanger (2010)).

Measuring Electrical Properties of Biological Tissue

The electrical properties of biological tissue can be measured when current flows through the tissue by a phenomenon termed "impedance" or alternatively "bioimpedance", which refers to the opposition to the flow of alternating current through a conductor, and is described by a relation between voltage and current in a system. (Holder, D. S., "Appendix A: A brief introduction to bioimpedance," in "Electrical Impedance Tomography", Institute of Physics Publishing, Bristol and Philadelphia (2005), pp. 411-422). Impedance is defined as the ratio of incremental change in voltage to the resulting current (or vice versa) across an electrochemical cell or an electrical circuit. (Crescentini, M. et al., "Recent trends for (bio)chemical impedance sensor electronic interfaces," Electroanalysis, 24(3): 563-572 (2012)).

Impedance can be measured in tissues and cells using electrochemical impedance spectroscopy (EIS). Through the application of a small sinusoidally varying potential U, one measures the resulting current response I. By repeating the process at varying excitation frequencies f, impedance can be calculated as a function of the angular frequency $\omega$, given by the relation:

$$Z(j\omega) = \frac{U(j\omega)}{I(j\omega)} = Z_r(\omega) + jZ_i(\omega),$$

where $\omega=2\Pi f$. (Grieshaber, D. et al., "Electrochemical biosensors," Sensors, 8: 1400-1458 (2008)).

More specifically, when applying a sinusoidal voltage reference $V_{ref}(t)=|V_{ref}|\sin(\omega_0 t)$ across the cell and assuming linear behavior, the corresponding current flowing through the cell is $I(t)=|I|\sin(\omega_0 t+\theta)$, wherein $\theta$ is the phase shift of the signal with respect to the excitation. Thus, the relationship between excitation and readout signals depends only on phases and amplitude ratios. (Crescentini, M. et al., "Recent trends for (bio)chemical impedance sensor electronic interfaces," Electroanalysis, 24(3): 563-572 (2012)). Therefore, impedance is made of two components: resistance or the real part of the data, and reactance, the out-of-phase data. (Crescentini, M. et al., "Recent trends for (bio)chemical impedance sensor electronic interfaces," Electroanalysis, 24(3): 563-572 (2012)).

Resistance (R) is a measure of the extent to which a substance opposes the flow of electrons or, in aqueous solution as in living tissue, the flow of ions among its cells. The three fundamental properties governing the flow of electricity are "voltage", "current" and "resistance". Voltage is the pressure exerted on a stream of charged particles moving down a wire or through an ionized salt solution. Current is the amount of charge flowing per unit time. Resistance is the ease or difficulty with which the charged particles can flow. Voltage, current and resistance are related by Ohm's law: V (voltage, Volts)=I (current, Amps)×R (resistance, Ohms (Ω)). Ohm's law applies to both direct current (d.c. or steadily flowing) or alternating current (a.c. or current that flows backwards and forwards).

Capacitance (C) refers to the extent to which an electronic component, circuit, or system stores and releases energy as the current and voltage fluctuate with each AC cycle. The capacitance physically corresponds to the ability of plates in a capacitor to store charge. With each cycle, charges accumulate and then discharge. Direct current cannot pass through a capacitor. Alternating current can pass because of the rapidly reversing flux of charge. The capacitance is an unvarying property of a capacitive or more complex circuit. However, the effect in terms of the ease of current passage depends on the frequency of the applied current; charges pass backwards and forwards more rapidly if the applied frequency is higher.

Reactance (X), analogous to resistance, refers to the current travelling through a capacitor or a coil. A higher reactance has a higher effective resistance to alternating current. Like resistance, its value is in Ohms, but it depends on the applied frequency, and is described by the relation: Reactance (Ohms)=1/(2×Π×Frequency (Hz)×Capacitance (Farads)). When a current is passing through a purely resistive circuit, the voltage recorded across the resistor will coincide exactly with the timing, or phase, of the applied alternating current. However, when current flows across a capacitor, the voltage recorded across it lags behind the applied current because of back and forth flow of current requiring alternating charging and discharging of the plates of the capacitor. In terms of a sine wave which has 360° in a full cycle, the lag is one quarter of a cycle, i.e., 90°.

Impedance is the frequency dependent resistance derived from the following three components of an AC circuit: direct current (DC) resistance; capacitive resistance; and inductive reactance. Capacitance is produced by storing charge on a surface at an energy expense producing a retardation of voltage flow. Inductance is produced by storing energy in a magnetic field in bulk space at an energy expense producing a retardation of current flow. Capacitance is counted in Farad units and inductance in Henry units. These two retardation effects are combined in a process and representation called the phase angle, which is the angular summation of the two waves or pulses of voltage and current. In the Mott-Schottky form of impedance measurement, only a single frequency influence is used. This is a departure from Nyquist or Cole (Cole, K. S, and Cole, R. H, "Dispersion and Absorption in Dielectrics. I. Alternating Current Characteristics," J. Chem. Phys. 9: 341-351 (1941)) plots, which utilize a descending frequency series. The Mott-Schottky method is useful for analysis of the underlying impedance vectors within devices and within molecules.

Palladium Compounds and Complexes

Certain palladium compounds have been described as inhibitors of growth, and have been shown to be interactive, or able to bind, with DNA. Such working concepts of growth inhibition are quite general and the mechanism of disease specificity has not been further approached.

Palladium is a transition metal of Group 10 of the periodic table. Its electron configuration is $1s^2 2s^2 p^6$, $3s^2 p^6 d^{10}$, $4s^2 p^6 d^{10}$. Palladium is a well-known catalyst. The d-orbital contribution of palladium allows an exaggerated extension of electronic radii, thereby minimizing Coloumbic attractive force and giving the d-orbital electrons the properties of unpaired electrons. Consequently, palladium presents a stable electronic state closely resembling the free radical state.

According to quantum theory, each electron has a spin that is associated with an angular momentum leading to a magnetic moment. Consequently, the negative charge carried by the electron is also associated with a spin resulting in a circulating electric current. The circulating current induces a magnetic moment $\mu_S$ which, if the electron is subjected to a steady magnetic field $H_0$, causes the electron to experience a torque that tends to align the magnetic moment with the field. The energy of the system depends upon the projection of the spin vector along $H_0$. Quantum theory stipulates that only two values are permitted for an electron, which means that the electron magnetic moment can only assume two projections or spin states onto the applied field: the "+½ spin state", when the electron's magnetic moment $\mu_S$ is aligned with the direction of the applied magnetic field $H_0$; and the "−½ spin state", when the electron's magnetic moment $\mu_S$ is aligned opposed to the direction of $H_0$. Consequently, the ensemble of energy levels also reduces to two values, designated as $E_+$, a lower energy level corresponding to the +½ spin state (aligned with the direction of the applied magnetic field) and $E_-$, a higher energy level corresponding to the −½ spin state (opposed to the direction of the applied magnetic field). Because the +½ spin state is of slightly lower energy, in a large population of electrons, slightly more than half of the electrons will occupy this state, while slightly less than half will occupy the −½ spin state. The slight excess of the electron spin in the direction of the magnetic field constitutes a slight net magnetization of the material, a phenomenon known as spin polarization. The difference in energy between the two spin states increases with increasing strength of the magnetic field $H_0$. The higher the strength of $H_0$, the more the net magnetization or the spin polarization, i.e. the higher the number of electrons that will occupy the +½ state as compared to the −½ state.

In addition to the spinning motion, the angular momentum vector of a spinning electron as a result of the torque exhibits a precession around the external field axis with an angular frequency $\omega_L$. The precessional motion, known as Larmour precession, is similar to a spinning top whose spin axis rotates slowly around the vertical. The frequency of precession, $\omega_L$ termed the Larmour frequency, is the number of times per second the electron precesses in a complete circle. The precessional frequency increases the strength of the magnetic field $H_0$.

If an electron that is precessing in an applied magnetic field is exposed to electromagnetic radiation of a frequency $\omega_A$ that matches with the precessional frequency $\omega_L$, the resulting condition is known as resonance. In the resonance condition, an electron of a lower energy +½ spin state (aligned with the applied magnetic field) will transition or flip to the higher energy −½ spin state (opposed to the applied magnetic field). In doing so, the electron absorbs radiation at this resonance frequency, $\omega_A = \omega_L$. This frequency corresponds to the separation between the energy levels of the two spin states, equal to $\Delta E = E_+ - E_-$. This phenomenon is called electron spin resonance (ESR). ESR measures a molecular splitting constant, which is the Gaussian distance or hyperfine shift between the repetitive peaks.

When stimulated by a reaction, the rate of precession can increase, and the dynamic effect is described as Rabi frequency. According to Maxwell-Faraday-Heaviside laws, a moving charge produces a magnetic field in its path, given by: Curl B=4 pi C, where Curl is the net circulating magnetic energy, and C is the charge density or rate of charge moving through a cross section of space or material.

When an atom or molecule has an even number of electrons, electron spins pair off in atomic or molecular orbitals so that virtually no net spin magnetism is exhibited; such material is said to be "diamagnetic". However, when an atom or molecule has an odd number of electrons, complete pairing is not possible and the material is said to be "paramagnetic". The phenomena of spin magnetism (spin polarization) and ESR are observed in paramagnetic materials. The minimally attracted spinning d-orbital electrons in palladium render paramagnetic properties in palladium complexes.

The motion of the palladium d-orbital electrons produces an intermittent or pulsed magnetic field. In suitable palladium complexes, the d-orbital electrons are capable of introducing long range molecular magnetic signals into chemical systems. Thus, palladium can form coordination complexes with suitable solubility, voltametric behavior, and oxidation state, such as the palladium-lipoic acid complex (PdLA). The transfer of electrons from PdLA to DNA or RNA and their consequent interactions have been shown with voltammetry and ESR spectroscopy. The shunting of electron energy from PdLA to DNA or RNA has been hypothesized to alter the nucleic acid configuration to heterochromatin. (U.S. Pat. Nos. 5,463,093, 5,679,697 and 5,776,973).

Palladium lipoic acid (PdLA) complexes and their use in the treatment of tumors and psoriasis have been disclosed in U.S. Pat. Nos. 5,463,093, 5,679,697 and 5,776,973, each of which is incorporated by reference in its entirety. Crystallographic studies have shown that the palladium lipoic acid complex forms a trigonal prism. The bonds of the palladium-lipoic acid complex are coordinate covalent, with the complex between palladium and lipoic acid bonded (1) at the carbonyl of the carboxyl group with probable resonance involvement of both oxygens; and (2) at one or more sulfur atoms. The result is a bent chain of lipoic acid, with its ends bonded by way of palladium coordination.

PdLA is a charge transfer catalyst and a synthetic DNA reductase. It was shown to electronically reduce DNA by spin coupling to the guanine base and to thereby condense chromatin to the heterochromatic inactive state. (Garnett, M., Krishnan, C., Jones, B., Spin coupled DNA, Electrochem. Soc. 217th Meeting, A774, 2010). Microscopic effects of PdLA on tumor cells and on yeast showed that cell nuclei were condensed by PdLA into a heterochromatic configuration that is associated with gene silencing. (U.S. Pat. Nos. 5,463,093, 5,679,697 and 5,776,973). It has recently been shown that regional mutation-rate variation is strongly associated with regional variation in chromatin organization into heterochromatin- and euchromatin-like domains. (Schuster-Buchler, B and Lehner, B., Nature 488: 504-507 (2012). PdLA was shown to resemble fern structures of liquid crystal polymers of ECM. (Garnett, M. and Remo, J. L., "DNA Reductase: A Synthetic Enzyme with Opportunistic Clinical Activity Against Radiation Sickness," International Symposium on Applications of Enzymes in Chemical and Biological Defense, Orlando, Fla., May, 2001, p. 41.)

Palladium and lipoic acid have unique electronic properties. In vivo, lipoic acid is part of mitochondrial Complex I, pyruvic dehydrogenase, and therefore directly interacts with the charge relay system of the mitochondria as a source of charge.

In parallel research, organo-palladium-zinc complexes of general formula $(Me)_a(Lipoic\ acid)_b(fatty\ acid)_c(amino\ acid)_e$, where a, b and c are each 1, d is 0 or 1, and e is 0, 1, or, wherein the standard potential of the complex is electropositive (meaning having a positive electric charge tending to attract electrons), have been developed. See PCT/US2011/032114, filed on Apr. 12, 2011, entitled NOVEL ORGANO-PALLADIUM COMPLEXES, which is incorporated by reference in its entirety. These complexes are cytotoxic to breast cancer, brain cancer and Ehrlich ascites carcinoma cells.

The inorganic catalyst literature identifies the palladium-ruthenium system (Pd—Ru) (Tripathi, S. N., Bharadwaj, S. R., Dharwadkar, S. R., The Pd—Ru System (Palladium-Ruthenium), J. of Phase Equilibria, V. 14, No. 5, 638-642, 1993; Adams, R. D., Captain, B. F. W., Smith, M. D. Lewis Acid-Base Interactions Between Metal Atoms and their Applications for the Synthesis of Bimetallic Cluster Complexes, J. Am. Chem. Soc., V. 124, No. 20, 5628-9, May 2002) as having a singular peritectic phase with synergic effect on the catalytic hydrogenation of nitroaromatics (Wan, B. S., Liao, S. J., XU, Y., Yu, D. R., Synergic Effect of Palladium-Based Bimetallic Catalysts for the Hydrogenation of Nitroaromatics, Reaction Kinetics and Catalysis Letters, V. 63, No. 2, 397-401). In peritectic transformations, a liquid and solid of fixed proportions react to form a new microcrystal phase capable of nucleation and growth. Pd—Ru also has Lewis acid-base interactions between the metal atoms (Tripathi, S. N., Bharadwaj, S. R., Dharwadkar, S. R., The Pd—Ru System (Palladium-Ruthenium), J. of Phase Equilibria, V. 14, No. 5, 638-642, 1993; Adams, R. D., Captain, B. F. W., Smith, M. D. Lewis Acid-Base Interactions Between Metal Atoms and their Applications for the Synthesis of Bimetallic Cluster Complexes, J. Am. Chem. Soc., V. 124, No. 20, 5628-9, May 2002). Ruthenium is a transition metal of group 8 of the periodic table. Its electronic configuration is 1s2 2s2p6 3s2p6d10 4s2p6d7 5s1.

The present invention describes organo-metallic complexes comprising palladium, ruthenium, and zinc, and their charge transfer properties.

SUMMARY

According to one aspect, the described invention provides an organo-metallic complex comprising a metal component comprising three metals and at least one organyl component, wherein the metal component comprise a transition metal component and a nontransition metal component. According to one embodiment, the transition metal component comprises a palladium component and a ruthenium component. According to another embodiment, the palladium component is a palladium complex. According to another embodiment, the ruthenium component is a ruthenium complex. According to another embodiment, the nontransition metal component is a zinc component, and the zinc component is a structural link between the ruthenium component and the palladium component. According to another embodiment, the organyl component is a structural link between the palladium component and the nontransition metal component. According to another embodiment, the organyl component comprises lipoic acid or a derivative thereof, a fatty acid component or a derivative thereof, at least one amino acid component, or a combination thereof. According to another embodiment, the fatty acid component comprises a hydrocarbon chain of from 2 to twenty carbon atoms, wherein at one end of the hydrocarbon chain ($\omega$ carbon) is a methyl group and at the other end ($\alpha$ carbon) is a carboxyl group. According to another embodiment, the fatty acid component is linoleic acid or a derivative thereof. According to another embodiment, a first amino acid component comprises arginine. According to another embodiment, the arginine is linked to the fatty acid component, and wherein the fatty acid component is a linoleic acid. According to another embodiment, the arginine facilitates water solubility of the linoleic acid. According to another embodiment, a second amino acid component is a structural link between ruthenium and zinc. According to another embodiment, the second amino acid component is N-formyl methionine.

According to another aspect, the described invention provides an organometallic complex of Formula I:

$$(Me)_a(\text{Lipoic acid})_b(\text{fatty acid})_c(\text{zinc})_d(\text{amino acid})_e \quad \text{(Formula I)}$$

wherein Me signifies a metal; the Me component contains a palladium component and a ruthenium component; the lipoic acid component comprises lipoic acid or a derivative thereof, wherein the lipoic acid component comprises at least two sulfur atoms and at least one carboxyl group; the fatty acid component comprises a hydrocarbon chain of from 2 to twenty carbon atoms wherein at one end of the hydrocarbon chain (ω carbon) is a methyl group and at the other end (α carbon) is a carboxyl group; and the zinc component is bonded to a methyl group at one end of the fatty acid component, wherein a is at least 2; b, and c are each 1; d is 0 or 1; e is 0, 1, or 2, and when e is 2, the amino acid component comprises a first amino acid and a second amino acid, wherein the first amino acid is bonded to the zinc component, and the second amino acid is bonded to the fatty acid component; wherein the palladium component is bonded to the lipoic acid component via both sulfur atoms and by the carboxyl group oxygens of the lipoic acid component; the fatty acid is bonded to the palladium via the carboxyl group of the fatty acid; and the ruthenium component is bonded to the amino acid that is bonded to the zinc component.

According to one embodiment, the palladium component is elemental palladium or a palladium salt selected from the group consisting of palladium chloride, palladium bromide, palladium iodide, palladium nitrate, palladium oxide, palladium sulfide, or a combination thereof. According to another embodiment, the ruthenium component is elemental ruthenium or a ruthenium salt selected from the group consisting of ruthenium chloride, ruthenium bromide, ruthenium iodide, ruthenium nitrate, ruthenium oxide, ruthenium sulfide, or a combination thereof. According to another embodiment, the lipoic acid comprises a side group selected from a carboxyl, a sulfur, an amine or a combination thereof. According to another embodiment, the lipoic acid derivative is lipoamide. According to another embodiment, the fatty acid component is linoleic acid. According to another embodiment, the fatty acid component is docosahexaenoic acid. According to another embodiment, the zinc component is a form of zinc selected from elemental zinc, zinc carbonate, zinc gluconate, zinc chloride, zinc pyrithione, zinc sulfide, zinc methyl or zinc diethyl. According to another embodiment, the first amino acid is formyl-methionine. According to another embodiment, the second amino acid is arginine. According to another embodiment, the complex further comprises at least one ligand, selected from an inorganic anionic ligand or a cationic ligand. According to another embodiment, the inorganic anionic ligand is acetate, acetylacetonate, amine, ammonium chloride, ammonium nitrate, bromide chloride, fluoride, iodide, nitrate, nitrite, oxalate, oxide, pyridine, sulfate or sulfide. According to another embodiment, the cationic ligand selected from sodium, potassium, magnesium, calcium, ammonia, vanadate, molybdate, zinc, and tin. According to another embodiment, the complex is thermodynamically stable. According to another embodiment, a Fourier Transform infrared spectrum of the complex comprises peaks at: :742 cm(−1), 965 cm(−1), 1034 cm(−1), 1356 cm(−1), 1402 cm(−1), 1604 cm(−1), 1668 cm(−1), 1958 cm(−1), 2921 cm(−1), and 3262 cm(−1). According to another embodiment, an electron spin resonance spectrum of the complex with hyaluronic acid is associated with a hyperfine splitting constant at 10.34 Gauss. According to another embodiment, the complex in the presence of hyaluronic acid is capable of depolarization of hydrogen peroxide inductance.

According to another aspect, the described invention provides a pharmaceutical composition comprising a therapeutic amount of an organometallic complex of Formula I:

$$(Me)_a(\text{Lipoic acid})_b(\text{fatty acid})_c(\text{zinc})_d(\text{amino acid})_e \quad \text{(Formula I)}$$

wherein Me signifies a metal; the Me component contains a palladium component and a ruthenium component; the lipoic acid component comprises lipoic acid or a derivative thereof, wherein the lipoic acid component comprises at least two sulfur atoms and at least one carboxyl group; the fatty acid component comprises a hydrocarbon chain of from 2 to twenty carbon atoms wherein at one end of the hydrocarbon chain (ω carbon) is a methyl group and at the other end (α carbon) is a carboxyl group; and the zinc component is bonded to a methyl group at one end of the fatty acid component, wherein a is at least 2; b, and c are each 1; d is 0 or 1; e is 0, 1, or 2, and when e is 2, the amino acid component comprises a first amino acid and a second amino acid, wherein the first amino acid is bonded to the zinc component, and the second amino acid is bonded to the fatty acid component; wherein the palladium component is bonded to the lipoic acid component via both sulfur atoms and by the carboxyl group oxygens of the lipoic acid component; the fatty acid is bonded to the palladium via the carboxyl group of the fatty acid; and the ruthenium component is bonded to the amino acid that is bonded to the zinc component; and a pharmaceutically acceptable carrier.

According to one embodiment, a therapeutic amount of a complex according to claim 15, and a pharmaceutically acceptable carrier. According to another embodiment, the complex is a solution or a dispersion. According to another embodiment, the complex is a solution, and wherein the complex in solution is present in an amount amount sufficient to obtain a concentration of about 5 mg/mL to 50 mg/mL. According to another embodiment, the composition is administered orally, enterally, parenterally, or topically. According to another embodiment, the therapeutic amount of the composition is effective in depolarization of hydrogen peroxide inductance.

According to another aspect, the described invention provides a method of treating an inflammatory disease or condition in a mammal, comprising: (a) providing the therapeutic amount of a pharmaceutical composition comprising a therapeutic amount of an organometallic complex of Formula I:

$$(Me)_a(\text{Lipoic acid})_b(\text{fatty acid})_c(\text{zinc})_d(\text{amino acid})_e \quad \text{(Formula I)}$$

wherein Me signifies a metal; the Me component contains a palladium component and a ruthenium component; the lipoic acid component comprises lipoic acid or a derivative thereof, wherein the lipoic acid component comprises at least two sulfur atoms and at least one carboxyl group; the fatty acid component comprises a hydrocarbon chain of from 2 to twenty carbon atoms wherein at one end of the hydrocarbon chain (ω carbon) is a methyl group and at the other end (α carbon) is a carboxyl group; and the zinc component is bonded to a methyl group at one end of the fatty acid component, wherein a is at least 2; b, and c are each 1; d is 0 or 1; e is 0, 1, or 2, and when e is 2, the amino acid component comprises a first amino acid and a second amino acid, wherein the first amino acid is bonded to the zinc component, and the second amino acid is bonded to the fatty acid component; wherein the palladium component is bonded to the lipoic acid component via both sulfur atoms and by the carboxyl group oxygens of the lipoic acid component; the fatty acid is bonded to the palladium via the carboxyl group of the fatty acid; and the ruthenium component is bonded to the amino acid that is bonded to the zinc component; and a pharmaceutically acceptable carrier; and (b) administering the therapeutic amount of the pharmaceutical composition to the mammal such that the therapeutic amount has at least one of the following effects: (i) an anti-inflammatory effect; and (ii) an anti-oxidant effect.

According to one embodiment, the inflammatory disease or condition is selected from the group consisting of an allergic condition, asthma, atopic dermatitis, atopic keratoconjunctivitis, angioedema, contact dermatitis, seborrheic dermatitis, rosacea, psoriasis, acne, an autoimmune disorder, an atherosclerotic condition, an arthritic condition, an inflammatory condition associated with a wound injury, a tendinopathy, an inflammatory condition associated with metal toxicity from an implantable device, or a combination thereof. According to another embodiment, the inflammatory disease or condition is an allergic condition. According to another embodiment, the allergic condition is allergic rhinitis. According to another embodiment, the allergic condition is allergic conjunctivitis. According to another embodiment, the inflammatory disease or condition is asthma. According to another embodiment, the inflammatory disease or condition is atopic dermatitis. According to another embodiment, the inflammatory disease or condition is atopic keratoconjunctivitis. According to another embodiment, the inflammatory disease or condition is angioedema. According to another embodiment, the inflammatory disease or condition is contact dermatitis. According to another embodiment, the inflammatory disease or condition is seborrheic dermatitis. According to another embodiment, the inflammatory disease or condition is rosacea. According to another embodiment, the inflammatory disease or condition is psoriasis. According to another embodiment, the inflammatory disease or condition is acne. According to another embodiment, the inflammatory disease or condition is an autoimmune disorder. According to another embodiment, the inflammatory disease or condition is an atherosclerotic condition. According to another embodiment, the inflammatory disease or condition is an arthritic condition. According to another embodiment, the inflammatory disease or condition is an inflammatory condition associated with a wound injury. According to another embodiment, the inflammatory disease or condition is a tendinopathy. According to one embodiment, the tendinopathy is a tendonitis. According to another embodiment, the tendinopathy is a tendinosis. According to another embodiment, the inflammatory disease or condition is an inflammatory condition associated with toxicity from a metal released from an implantable device. According to another embodiment, the implantable device is selected from the group consisting of a surgical implant, a prosthetic device, a dental device, a metal containing contraception device, or a combination thereof. According to one embodiment, the prosthetic device is selected from the group consisting of a prosthetic joint, a hip replacement device, a joint arthroplasty implant, a heart valve, or a combination thereof. According to another embodiment, the surgical implant is selected from the group consisting of a plate, a rod, a screw, a stent, a pacemaker, a defibrillator, a catheter, or a combination thereof. According to another embodiment, the metal containing contraception device is an intra-uterine device. According to another embodiment, the metal is selected from the group consisting of copper, chromium, molybdenum, aluminium, vanadium, nickel, iron, titanium, or a combination thereof. According to another embodiment, the metal is in a form selected from the group consisting of a metal particle, a metal ion, a metal oxide, a metal hydroxide, or a combination thereof. According to one embodiment, the metal particle is at least 5 nm, at least 50 nm, or at least 500 nm in size. According to another embodiment, the anti-inflammatory effect of the therapeutic amount is effective to reduce the level of at least one inflammatory mediator selected from the group consisting of TNF-α, IL-1β, NF-κB, IL-6, and IL-8, as compared to a normal control. According to another embodiment, the anti-oxidant effect of the therapeutic amount is effective to increase the oxidation-reduction status of an affected cell, as compared to a normal control. According to another embodiment, the anti-oxidant effect of the therapeutic amount is effective to reduce oxidative stress by reducing the level of at least one reactive oxygen species in an affected cell, as compared to a normal control. According to another embodiment, the administering is parenterally, enterally, topically, transdermally, or nasally by inhalation.

DETAILED DESCRIPTION OF THE INVENTION

Glossary

Figure 1:
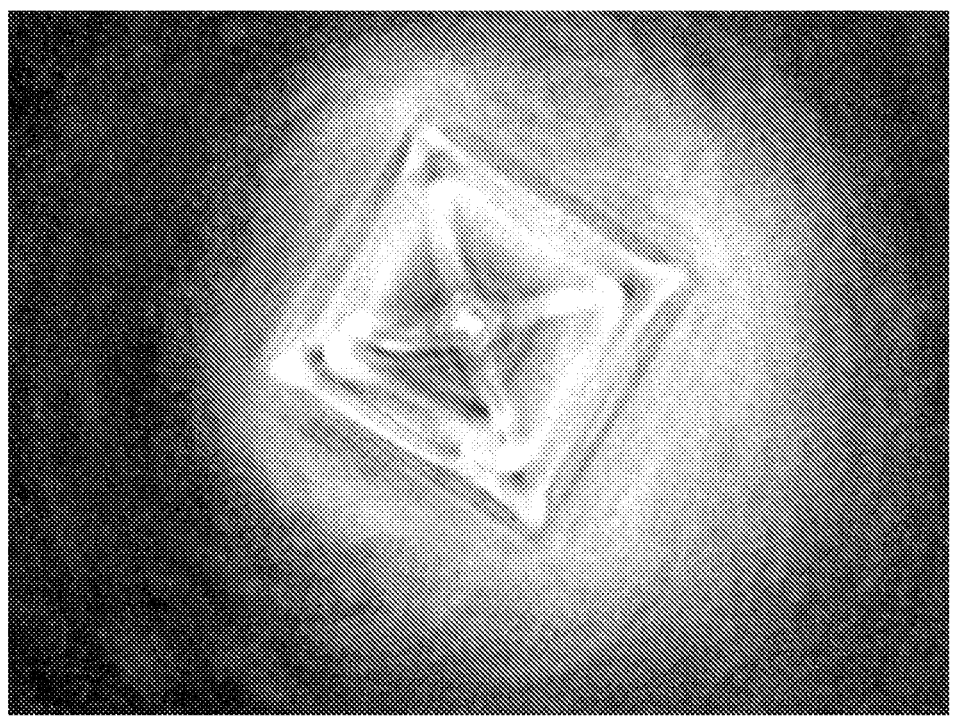
FIG. 1 is a low power phase microscope image of a single GML-X3 crystal about 0.2 μm in dimension. Solid state crystals of GML-X3 are prepared by making a dozen glass streak slides from a stock solution of GML-X3. A 10.0 μL loupe is used to spread the GML-X3 evenly over an entire slide. The slides are allowed to dry for three days and then examined under low power Nikon Labophot-2 Phase Fluorescence microscope at phase magnification of 300×. The crystals appear octahedral in shape. Generally, they vary in size ranging between 0.2 μm to 0.2 mm in dimension.

The term "alloy" as used herein refers to a mixture of two or more elements, one of which must be a metal, to form a macroscopically homogeneous metallic product.

The term "anionic ligand" as used herein refers to a monoatomic or polyatomic species capable of bonding having one or more elementary charges of an electron and is therefore negatively charged.

The term "anti-inflammatory" as used herein refers to reducing inflammation by acting on body responses, without directly antagonizing the causative agent.

The term "anti-inflammatory effect" as used herein refers to the ability of a substance to reduce signs and symptoms of inflammation, such as swelling, tenderness, fever and pain.

The term "antioxidant" as used herein refers to an agent that inhibits oxidation, that can neutralize the oxidant effect of free radicals and other substances. An oxidant is the substance that is reduced (i.e., gains electrons) and therefore oxidizes the other component of an oxidation-reduction system (which therefore loses electrons).

The term "capacitor" as used herein refers to a component, which has capacitance.

The term "cationic ligand" as used herein refers to a monoatomic or polyatomic species capable of bonding having one or more elementary charges of a proton, and is therefore positively charged.

The term "charge transfer" as used herein refers to the transfer of electric charge, for example transfer of electrons or protons, from one entity to another, or from one location to another within the same entity.

The term "chemokine" as used herein refers to a class of chemotactic cytokines that signal leukocytes to move in a specific direction.

The term "condition," as used herein, refers to a variety of health states and is meant to include disorders or diseases caused by any underlying mechanism or disorder.

The term "coordinate bond" or "coordinate covalent bond" as used herein refers to a covalent bond consisting of a pair of electrons donated by only one of the two atoms it joins. Coordinate bonds are weaker than covalent bonds that formed by the sharing of pairs of electrons between atoms.

The term "coordination alloy" as used herein refers to an alloy containing one or more coordinate bonds joining one or more of its constituent chemical entities.

The term "coordination entity", "coordination complex", "complex" or "complex entity" as used herein refers to a molecular entity formed in a crystal and ligand field produced by a metal and a second molecule. The strength of the complex is derived from the stability of the crystal symmetry and the delocalization and sharing of charges. A coordination complex may or may not be covalent. There are many covalent coordination complexes, including, without limitation, vitamin B12, hemoglobin, chlorophyll, the nitrogenase enzyme, and the cytochromes.

The term "cytokine" as used herein refers to small soluble protein substances secreted by cells, which have a variety of effects on other cells. Cytokines mediate many important physiological functions, including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "derivative" as used herein means a compound that may be produced from another compound of similar structure in one or more steps. A "derivative" or "derivatives" of a component or a compound retains at least a degree of the desired function of the component or compound. Accordingly, an alternate term for "derivative" may be "functional derivative." Derivatives can include chemical modifications, such as alkylation, acylation, carbamylation, iodination or any modification that derivatizes the component or compound. Examples of such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "depolarization" as used herein refers to the removal, decrease or prevention of polarization, the separation of electric charges into a positive and negative pole. Depolarization includes a removal or decrease in charge separation of an electric dipole, or separation of $+\frac{1}{2}$ and $-\frac{1}{2}$ spin states of a magnetic dipole.

The term "detoxification" as used herein refers to lowering of the level of free radicals such that their toxic effects are reduced. Detoxification includes, but is not limited to, depolarization of free radicals.

The terms "dipole" as used herein refers to state of separation of two opposite or opposing attributes, magnitudes or the like. A dipole can be an electric dipole or a magnetic dipole. The term "electric dipole" used herein refers to a state of separation of two opposite charges of equal magnitude separated by a very small distance. A dipole is characterized by a vector quantity, known as the dipole moment, that points from the negative charge towards the positive charge. The dipole moment is the product of the magnitude of one of the charges and the distance between the centers of the charges. The term "magnetic dipole" as used herein refers to the state of separation of two equal magnetic poles with opposite polarity separated by a distance. The term "magnetic spin dipole" as used herein refers to the state of separation of separation of $+\frac{1}{2}$ and $-\frac{1}{2}$ spin states along an applied magnetic field.

The term "discharge" as used herein refers to the depletion or removal of stored electric charge.

The terms "disease" or "disorder" as used herein refer to an impairment of health or a condition of abnormal functioning.

The term "electronegative" as used herein refers to the ability of a chemical entity to attract electrons or electron density toward itself.

The term "electropositive" as used herein refers to the ability of a chemical entity to donate electrons or electron density away from itself.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "impedance", "bioimpedance", "electrical impedance" or "electrochemical impedence" as used herein refers to frequency dependent resistance derived from three components of an AC circuit: direct current (DC) resistance; capacitive reactance (or capacitance); and inductive reactance (or inductance). Impedance is the opposition to the flow of alternating current through a conductor, and is described by a relation between voltage and current in a system. Impedance is defined as the ratio of incremental change in voltage to the resulting current (or vice versa) across an electrochemical cell or an electrical circuit. Impedance has two components: resistance, which is a real number, and reactance, an imaginary number. It is usually measured by applying a sinusoidally varying AC potential to an electrochemical cell and then measuring the current through the cell as a function of frequency. The terms "capacitance" and "capacitive resistance" is used interchangeably to mean resistance that is produced by storing charge on a surface at an energy expense producing a retardation of voltage flow. The terms "inductance" and "inductive resistance" are used interchangeably to mean resistance that is produced by storing energy in a magnetic field in bulk space at an energy expense producing a retardation of current flow. These two retardation effects are combined in a process and representation called the phase angle which is the angular summation of the two waves or pulses of voltage and current.

The term "implantable device" as used herein refers to a medical device intended to be placed in the body of a subject, such as a human, surgically or within a naturally formed cavity to assist, restore, or replace a structure of the body.

A free radical is a highly reactive and usually short-lived molecular fragment with one or more unpaired electrons. Free radicals are highly chemically reactive molecules. Because a free radical needs to extract a second electron from a neighboring molecule to pair its single electron, it often reacts with other molecules, which initiates the formation of many more free radical species in a self-propagating chain reaction. This ability to be self-propagating makes free radicals highly toxic to living organisms. Oxidative injury may lead to widespread biochemical damage within the cell. The molecular mechanisms responsible for this damage are complex. For example, free radicals may damage intracellular macromolecules, such as nucleic acids (e.g., DNA and RNA), proteins, and lipids. Free radical damage to cellular proteins may lead to loss of enzymatic function and cell death. Free radical damage to DNA may cause problems in replication or transcription, leading to cell death or uncontrolled cell growth. Free radical damage to cell membrane lipids may cause the damaged membranes to lose their ability to transport oxygen, nutrients or water to cells. There are many types of free radicals but most common radicals in biological systems are derived from oxygen, collectively known as reactive oxygen species (ROS). ROS comprise oxygen derived small molecules such as oxygen radicals: superoxide, hydroxyl, peroxyl, and alkoxyl; or the nonradicals: hypochlorous acid, ozone, singlet oxygen, and hydrogen peroxide. Oxygen ($O_2$) has two unpaired electrons in separate orbitals in its outer shell. Sequential reduction of molecular oxygen (equivalent to sequential addition of electrons) leads to the formation of a group of reactive oxygen species: superoxide anion ($O_2^{\cdot-}$), peroxide ($O_2^{\cdot-2}$) and hydroxyl radical (.OH). Another radical derived from oxygen is singlet oxygen ($^1O_2$), an excited form of oxygen in which one of the electrons is present in a higher energy level upon absorption of energy.

The term "Lewis acid" as used herein refers to any molecule (called an electrophile) that can combine with another molecule or ion by forming a covalent bond with two electrons from the second molecule or ion. A Lewis acid is thus an electron acceptor.

The term "Lewis base" as used herein refers to a substance (also called a nucleophile) that forms a covalent bond by donating a pair of electrons, with neutralization resulting from reaction between the base and the acid with formation of a coordinate covalent bond. A Lewis base is therefore an electron donor.

The term "ligand" as used herein refers to a chemical entity or species, an atom, a molecule, or an ion, that is bonded to the central metal atom of a coordinate complex via coordinate covalent bonds.

The term "liquid crystal" as used herein refers matter that has properties between those of a conventional liquid and those of a solid crystal.

The term "lone pair" as used herein refers to two paired electrons localized in the valence shell, the highest molecular orbitals, on a single atom.

The term "organified" as used herein refers to a state of being bonded to an organyl group by a covalent or coordination covalent bond.

The term "organometallic complex" as used herein refers to a coordination entity having one or more coordination covalent bonds between one or more metal atoms and one or more carbon atoms of an organyl group.

The term "organometallic compound" as used herein refers to a compound having one or more bonds between one or more metal atoms and one or more carbon atoms of an organyl group.

The term "organyl" as used herein refers to containing any organic substituent group, regardless of functional type, having one free valence at a carbon atom.

The term "oscillation" as used herein refers to a periodic variation around a set point.

The term "oxidation" as used herein refers to the loss of one or more electrons or a concomitant increase in the oxidation state. The term "oxidized form" as used herein refers to a form of a chemical entity which has undergone oxidation, i.e. lost one or more electrons.

The term "oxidation state" as used herein refers to the degree of oxidation in a chemical entity.

The term "oxidative stress" as used herein refers to a redox imbalance within the cell usually due to increased reactive oxygen species (ROS) and decreased antioxidants.

Peroxide depolarization and denaturation as used herein refers to a phase angle reversal of the polarity of the inductance spike, which represents a plot of the inductance field discharge and the denaturation of the peroxide in the electric double layer.

The term "peritectic point" as used herein refers to the point on a phase diagram where a reaction takes place between a previously precipitated phase and the liquid to produce a new solid phase.

The term "pharmaceutically acceptable carrier" as used herein refers to one or more compatible solid or liquid filler, diluent or encapsulating substance which is/are suitable for administration to a human or other vertebrate animal. The components of the pharmaceutical compositions also are capable of being commingled in a manner such that there is no interaction which would substantially impair the desired pharmaceutical efficiency. As used herein the phrase "pharmaceutically acceptable carrier" refers to any substantially non-toxic carrier useable for formulation and administration of the composition of the described invention in which the organometallic complex of the described invention will remain stable and bioavailable.

The term "pharmaceutical composition" is used herein to refer to a composition that is employed to prevent, reduce in intensity, cure or otherwise treat a target condition or disease.

The term "polarity" as used herein refers to the possession or manifestation of two opposite or opposite attributes, magnitudes, or the like, for example, electrical or magnetic polarity. The term "electrical polarity" as used herein refers to the property of having an excess or a deficiency of electrons. An excess of electrons produces a negative polarity and a deficiency of electrons produces a positive polarity. This determines the flow of electric current as electrons move from a point with an excess of electrons towards a point deficient in electrons. The term "magnetic spin polarity" as used herein refers to the presence of two regions representing opposite spin states.

The term "potential" or "standard potential" as used herein refers to the work required to bring a unit charge from a reference point to a specific point within an electric field. The term "electropositive potential" or "electropositive standard potential" or "oxidation potential" as used herein refers to a measure of the tendency to donate electrons, and thereby be oxidized. The term "electronegative potential" or "electronegative standard potential" or "reduction potential" as used herein refers to a measure of the tendency to attract electrons, and thereby be reduced.

The term "potential difference" as used herein refers to the difference between the potentials of two points in an electric field.

The term "potential gradient" as used herein refers to the rate of change of potential with respect to distance in the direction of the greatest charge.

The term "precession" as used herein refers to the change in orientation of the rotational axis of a rotating body, analogous to the wobble of a spinning top. The term "Larmour precession" refers to the precession of an electron subjected to a torque induced by an applied magnetic field around the axis of the applied magnetic field. The term "Larmour frequency $\omega L$" or "precessional frequency" as used interchangeably herein refers to the angular frequency, the number of times per second the electron precesses in a complete circle around the field axis.

The term "Reactance (X)" as used herein refers to the current travelling through a capacitor. A higher reactance has a higher effective resistance to alternating current. Like resistance, its value is in Ohms, but it depends on the applied frequency, and is described by the relation: Reactance (Ohms)=$1/(2 \times \Pi \times Frequency\ (Hz) \times Capacitance\ (Farads))$. When a current is passing through a purely resistive circuit, the voltage recorded across the resistor will coincide exactly with the timing, or phase, of the applied alternating current. However, when current flows across a capacitor, the voltage recorded across it lags behind the applied current because of back and forth flow of current requiring alternating charging and discharging of the plates of the capacitor. In terms of a sine wave which has 360° in a full cycle, the lag is one quarter of a cycle, i.e., 90°.

The term "reduction" as used herein refers to the gain of electrons or a concomitant decrease in the oxidation state. The term "reduced form" as used herein refers to a form of a chemical entity which has undergone reduction, i.e. gained one or more electrons.

The term "resistance (R)" as used herein refers to a measure of the extent to which an element opposes the flow of electrons or, in aqueous solution as in living tissue, the flow of ions among its cells. The three fundamental properties governing the flow of electricity are "voltage", "current" and "resistance". Voltage is the pressure exerted on a stream of charged particles moving down a wire or through an ionized salt solution. Current is the amount of charge flowing per unit time. Resistance is the ease or difficulty with which the charged particles can flow. Voltage, current and resistance are related by Ohm's law: V (voltage, Volts)=I (current, Amps)×R (resistance, Ohms ($\Omega$)).

The term "semiconductor" as used herein refers a material whose conductivity lies between that of an electrical conductor, such as a metal, and an insulator The term "solid state" as used herein refers to consisting of, pertaining to, characterized of or arising from matter whose state of matter is solid. The function usually depends on electrical, magnetic and/or optical phenomena occurring within the solid.

The term "spin" as used herein refers to the rotation of a subatomic charged particle, such as electron or nucleus around its axis. Spins result in generation of a magnetic field that is associated with a small quantity of angular momentum leading to a magnetic moment intrinsic to a charge carrier (such as an electron).

The terms "spin coupling" or "spin-spin interaction" as used herein refer to the interaction between the magnetic moment of an spinning charged particle (such as an electron or atomic nucleus) with the magnetic moment of another in its vicinity. In case of electron systems, spin-spin coupling results in the splitting of electron spin resonance lines, a phenomenon known as hyperfine splitting or hyperfine interaction.

The terms "spin moment" or "spin vector" are used interchangeably to refer to the magnetic moment, a vector quantity, induced by the circulating electric current resulting from the negative charge carried by a spinning electron.

The term "spin polarization" or "spin magnetism" as used herein refers to the degree to which the intrinsic spin moment is aligned with a given direction. When an atom or molecule has an even number of electrons, electron spins pair off in atomic or molecular orbitals so that virtually no net spin magnetism is exhibited; such material is said to be "diamagnetic". However, when an atom or molecule has an odd number of electrons, complete pairing is not possible and the material is said to be "paramagnetic".

The term "spin state" as used herein refers to the projection of the spin moment (spin vector) $\mu S$ along an applied magnetic field $H_0$. When subjected to a magnetic field, an electron with magnetic moment $\mu_S$ experiences a torque that tends to align the magnetic moment with the magnetic field. The energy of the system depends upon the projection of the spin vector along $H_0$. Quantum theory stipulates that only two values are permitted for an electron, which means that the electron magnetic moment can only assume two projections or spin states onto the applied field: the "+½ spin state", when the electron's magnetic moment $\mu_S$ is aligned with the direction of the applied magnetic field $H_0$; and the "−½ spin state", when the electron's magnetic moment $\mu_S$ is aligned opposed to the direction of $H_0$. Consequently, the ensemble of energy levels also reduce to two values, designated as $E_+$, a lower energy level corresponding to the +½ spin state (aligned with the direction of the applied magnetic field) and K, a higher energy level corresponding to the −½ spin state (opposed to the direction of the applied magnetic field). Because the +½ spin state is of slightly lower energy, in a large population of electrons, slightly more than half of the electrons will occupy this state, while slightly less than half will occupy the −½ spin state. The slight excess of the electron spin in the direction of the magnetic field constitutes a slight net magnetization of the material, a phenomenon known as spin polarization or spin magnetism. The difference in energy between the two spin states increases with increasing strength of the magnetic field $H_0$. Higher the strength of $H_0$, more is the net magnetization or the spin polarization, i.e. more number of electrons will occupy the +½ state as compared to the −½ state.

The terms "spin resonance" or "electron spin resonance (ESR)" are used interchangeably to refer to a condition in which an electron absorbs energy in flipping from a lower energy level to a higher energy level when exposed to an electromagnetic radiation of a frequency that matches the precessional frequency (Larmour frequency) of the electron. In this resonance condition, an electron of a lower energy +½ spin state (aligned with the applied magnetic field) will transition or flip to the higher energy −½ spin state (opposed to the applied magnetic field). In doing so, the electron absorbs radiation at this resonance frequency, $\omega_A=\omega_L$.

The term "spin polarized current" as used herein refers to a current with more electrons of either spin.

The term "spin transfer" as used herein refers to the following. By passing a current through a thick magnetic layer, one can produce a spin-polarized current. If a spin-polarized current is directed into a magnetic layer, angular momentum can be transferred to the layer changing its orientation. This can be used to excite oscillations or to flip the orientation of the magnet.

The term "superconductor" as used herein refers to an element, alloy, compound or other material which exhibits superconductivity, meaning the flow of current with a complete, or nearly complete, disappearance of all electrical resistance. Superconductors have a "gap" in energy where there are no states (so electrons cannot tunnel in); at a vortex line, the magnetic field closes the gap and there are states to tunnel into.

The term "tendinopathy" as used herein refers to a disease, disorder or condition of a tendon, e.g., tendinitis, and tendinosis. The terms "tendinitis" or "tendonitis" are used interchangeably to mean inflammation of a tendon. The term "tendinosis" as used herein refers to damage to a tendon at a cellular level exhibiting a pathology of chronic degeneration without inflammation. The term "tendon" as used herein refers to a nondistensible fibrous cord or band of variable length that is the part of muscle that connects the contracile part of the muscle with its bony attachment or other structure.

The terms "therapeutic amount", "therapeutic effective amount" or an "amount effective" of one or more of the therapeutic agents is an amount that is sufficient to provide the intended beneficial effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. A therapeutic effective amount for any particular application may vary depending on such factors as the disease or condition being treated, the particular therapeutic agent being administered, the size of the subject, or the severity of the disease or condition. One of ordinary skill in the art may determine empirically the effective amount of a particular therapeutic agent without necessitating undue experimentation. It is preferred generally that a maximum tolerated dose (MTD) be used, that is, the highest dose that will produce the desired effect without unacceptable toxicity according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "transition metal" or "transition element" as used herein refers to an element whose atom has an incomplete d sub-shell, or which can give rise to cations with an incomplete d sub-shell. Non-transition metals are metals that are not transition metals.

The term "valence" as used herein refers to the maximum number of univalent atoms that may combine with an atom of another element.

The term "vortex" as used herein refers to a specific phase state that can have diverse morphologies, such as hurricane, whirlpool, or black hole, but has a unique funnel geometry designed for energy focus.

The term "vortex pinning" as used herein refers to a dynamic phase change involving the localization and maturation of a vortex with a surface or a matrix. Pinning involves an exchange of vortex energy with the matrix or the surface. Glycine is one example of a chemical matrix suitable for pinning certain vortices.

Organo Metallic Complexes

According to one aspect, the described invention comprises an organo-metallic complex comprising three metal components. According to one embodiment, the complex comprises two transition metal components, a nontransition metal component, and at least one organyl component. According to one embodiment, the transition metal component comprises a palladium component and a ruthenium component. According to one embodiment, the palladium component is a palladium complex. According to one embodiment, the ruthenium component is a ruthenium complex. According to one embodiment, the nontransition metal component is a zinc component. According to another embodiment, the zinc component links a ruthenium complex with a palladium complex. According to one embodiment, the at least one organyl component comprises lipoic acid or a derivative thereof. According to one embodiment, the at least one organyl component comprises a fatty acid component or a derivative thereof. According to one embodiment, the fatty acid comprises a hydrocarbon chain of from 2 to twenty carbon atoms, wherein at one end of the hydrocarbon chain is a methyl group and at the other end is a carboxyl group. According to one embodiment, the fatty acid component is linoleic acid or a derivative thereof. According to one embodiment, the at least one organyl component comprises at least one amino acid component. According to one embodiment, a first amino acid component comprises arginine. According to one embodiment, the fatty acid derivative is a linoleic acid to which the arginine is linked. According to one embodiment, the arginine facilitates the water solubility of the linoleic acid. According to one embodiment, the linoleic acid or derivative thereof is a structural link between the palladium component and the zinc component. According to another embodiment, a second amino acid component forms a structural link between ruthenium and zinc. According to one such embodiment, the second amino acid component is N-formyl methionine.

According to one embodiment, the described invention comprises an organometallic complex of Formula I:

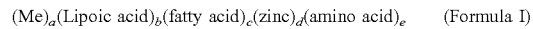

wherein

Me signifies a metal;

the metal (Me) component contains a palladium component and a ruthenium component;

the lipoic acid component comprises lipoic acid or a derivative thereof, wherein the lipoic acid component comprises at least two sulfur atoms and at least one carboxyl group;

the fatty acid component comprises a hydrocarbon chain of from 2 to twenty carbon atoms wherein at one end of the hydrocarbon chain is a methyl group and at the other end is a carboxyl group; and the zinc component is bonded to a methyl group at one end of the fatty acid, wherein a is at least 2;

b, and c are each 1;

d is 0 or 1;

e is 0, 1, or 2, and when e is 2, the amino acid component comprises a first amino acid and a second amino acid, wherein the first amino acid is bonded to the zinc component, and the second amino acid is bonded to the fatty acid component;

wherein the palladium component is bonded to the lipoic acid component via both sulfur atoms and by the carboxyl group oxygens of the lipoic acid component;

the fatty acid is bonded to the palladium via the carboxyl group of the fatty acid; and the ruthenium component is bonded to the amino acid that is bonded to the zinc component.

According to one embodiment, the complex comprises an organified ruthenium component comprising a ruthenium component and at least one organyl component, wherein the ruthenium component is bonded to the organyl component. According to one embodiment, the organyl component comprises a first amino acid component. According to one such embodiment, the first amino acid component is N-formyl methionine.

According to one embodiment, the complex comprises an organified palladium component comprising a palladium component and at least one organyl component, wherein the palladium component is bonded to the organyl component. According to one embodiment, the organyl component comprises lipoic acid or a derivative thereof. According to one embodiment, the organyl component comprises a fatty acid component or a derivative thereof. According to one embodiment, the fatty acid component comprises a hydrocarbon chain of from 2 to twenty carbon atoms, wherein at one end of the hydrocarbon chain (the ω carbon) is a methyl group and at the α carbon at the other end is a carboxyl group. According to one embodiment, the fatty acid component is linoleic acid or a derivative thereof. According to one embodiment, the at least one organyl component comprises a second amino acid component. According to one such embodiment, the amino acid component is arginine. According to one embodiment, the fatty acid derivative is a linoleic acid to which the arginine is linked. According to one embodiment, the arginine facilitates water solubility of the linoleic acid.

Figure 16:
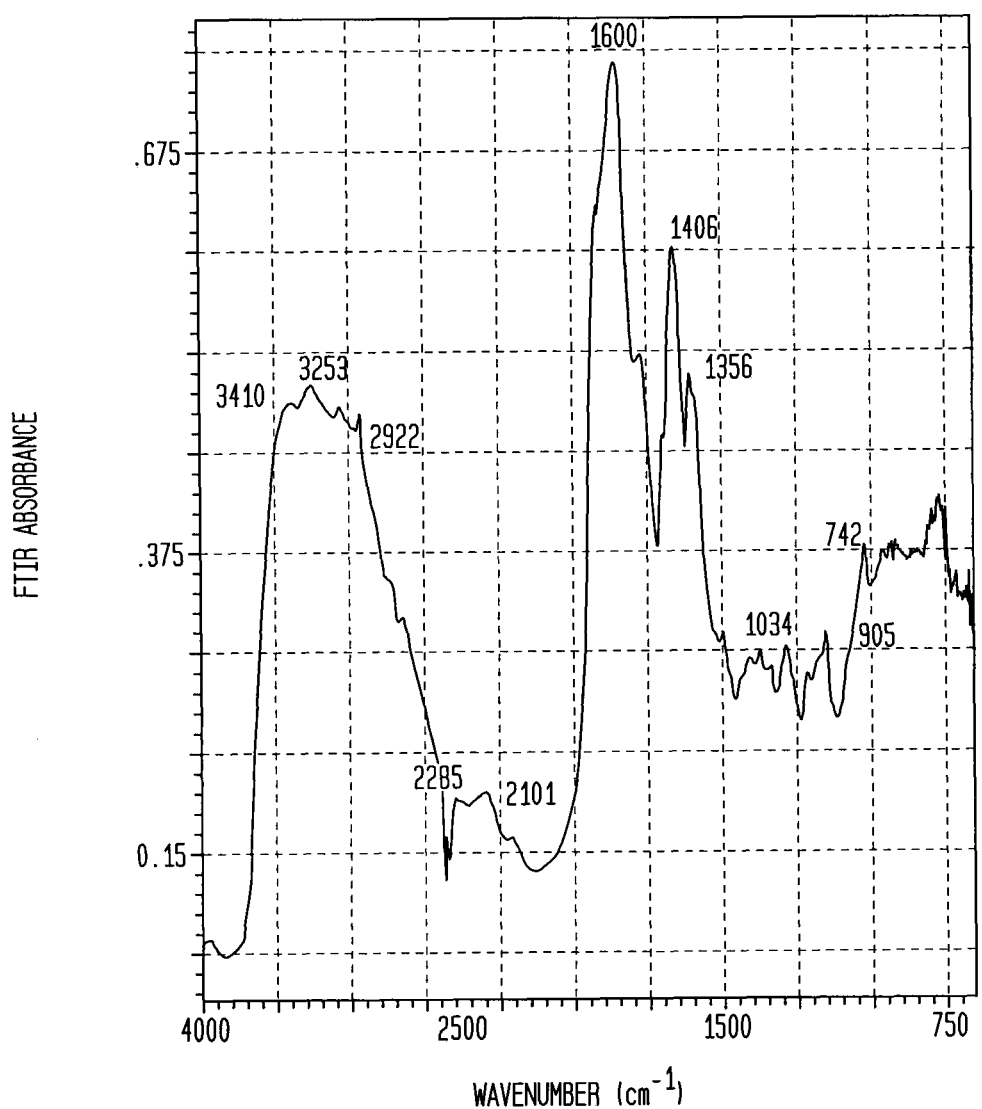
FIG. 16 shows a Fourier Transform Infrared (FTIR) spectrum of a mixture of GML-X3 in glycine Shimadzu Model 8400S FTIR Spectrophotometer, revealing induction of a new peak at 3410 cm(−1).

According to one embodiment, the organified palladium component is bonded to the organified ruthenium component via a zinc component, wherein the first amino acid component is formyl methionine, and the second amino acid component is arginine. According to one embodiment, the arginine functions as a charge donor. According to one embodiment, the complex is monomolecular in nature. According to one embodiment, the complex is capable of charge transfer. An exemplary general structure of GML-X3, a monomolecular charge transfer organo-metallic complex containing two transition metals palladium, ruthenium, and the nontransition metal zinc is shown in FIG. 16. The organometallic complex of GML-X3 comprises an organified palladium component that is referred to as G10, and an organified ruthenium component that is referred to Ru-formyl methionine. In the GML-X3 complex, the G10 component is bonded to the Ru-formyl methionine component via a zinc component.

According to one embodiment, GML-X3 is assembled from a plurality of precursor chemical entities to produce a single monomolecular complex. According to one embodiment, the first precursor chemical entity comprises an organified ruthenium component comprising a ruthenium component and at least one organyl group, wherein the ruthenium component is bonded to the at least one organyl group. According to one such embodiment, the at least one organyl group comprises a first amino acid. According to one such embodiment, the first amino acid is formyl methionine. According to one embodiment, the second precursor chemical entity comprises an organified palladium component, comprising a palladium-lipoic acid complex bonded to at least one organyl group. According to one such embodiment, the palladium-lipoic acid complex comprises a palladium component and a lipoic acid component, wherein the palladium component is bonded to the lipoic acid component via both sulfur atoms and by the carboxyl group oxygens of the lipoic acid component. According to one such embodiment, the at least one organyl group is a fatty acid. According to one such embodiment, the at least one organyl group is a second amino acid. According to one such embodiment, the second amino acid is arginine. According to another embodiment, integrated electronic transport of the single GML-X3 complex enables spin transfer.

Palladium Component

Palladium is a transition metal of Group 10 of the periodic table. According to some embodiments, the palladium component is selected from elemental palladium or a palladium salt. According to one embodiment, the palladium component is in the form of elemental palladium. According to one embodiment, the palladium component is a palladium salt. According to another embodiment, a palladium salt is employed in preparing the organified palladium component of the described invention. Such palladium salts include, without limitation, palladium acetate, palladium acetylacetonate, palladium ammonium chloride, palladium ammonium nitrate, palladium bromide, palladium chloride, palladium diamine nitrite, palladium diamylamine nitrite, palladium dibromide, palladium difluoride, palladium dioxide, palladium dipyridine nitrite, palladium ethylenediamine nitrite, palladium iodide, palladium monoxide, palladium nitrate, palladium oxalate, palladium oxide, palladium sulfate, palladium sulfide, palladium tetramine dichloride, palladous potassium bromide, palladous potassium chloride, palladous sodium bromide, and palladous sodium chloride. According to some such embodiments, the palladium salt is palladium chloride, palladium bromide, palladium iodide, palladium nitrate, palladium oxide or palladium sulfide. According to some such embodiments, the palladium salt is palladium chloride.

Ruthenium Component

Ruthenium is a transition metal of Group 8 of the periodic table. According to some embodiments, the ruthenium component is selected from elemental ruthenium or a ruthenium salt. According to one embodiment, the ruthenium component is in the form of elemental ruthenium. According to another embodiment, a ruthenium salt is employed in preparing the organified ruthenium component of the described invention. Such ruthenium salts include, without limitation, ruthenium acetate, ruthenium acetylacetonate, ruthenium ammonium chloride, ruthenium ammonium nitrate, ruthenium bromide, ruthenium chloride, ruthenium diamine nitrite, ruthenium diamylamine nitrite, ruthenium dibromide, ruthenium difluoride, ruthenium dioxide, ruthenium dipyridine nitrite, ruthenium ethylenediamine nitrite, ruthenium iodide, ruthenium monoxide, ruthenium nitrate, ruthenium oxalate, ruthenium oxide, ruthenium sulfate, ruthenium sulfide, ruthenium tetramine dichloride, ruthenium potassium bromide, ruthenium potassium chloride, ruthenium sodium bromide, and ruthenium sodium chloride. According to some such embodiments, the ruthenium salt is ruthenium chloride, ruthenium bromide, ruthenium iodide, ruthenium nitrate, ruthenium oxide or ruthenium sulfide. According to some such embodiments, the ruthenium salt is ruthenium chloride.

Lipoic Acid Component:

According to some embodiments, the lipoic acid component comprises lipoic acid or a derivative thereof. Lipoic acid and its derivatives are highly specific for transferring electron energy from a normal metabolic hydrogen carrier to nucleic acids. Lipoic acid has a long, flexible side chain, which enables it to rotate from one active site to another in enzyme complexes. As shown in Campbell et al, Biochemistry Illustrated, 2d, Churchill Livingstone, 126 (1988), lipoic acid is a hydrogen carrier and an acetyl-group carrier for the decarboxylation of pyruvic acid. Lipoic acid is then present as acetyl-lipoic acid, having both an acetyl group and a hydrogen atom. In the pyruvic decarboxylation reaction, the acetyl group is donated to CoA and the H is donated to NAD+.

According to one embodiment, the lipoic acid component comprises at least two sulfur atoms, a hydrocarbon chain having a length of two to twenty carbon atoms, and one or more carboxyl groups. According to one embodiment, the lipoic acid component is in its reduced or dithiol form. According to another embodiment, the lipoic acid component is in its oxidized or disulfide form. Whether the oxidized or reduced form is favored will depend upon the pH of the solution containing the complex.

According to some embodiments, the lipoic acid component is a derivative of lipoic acid, in either its oxidized or reduced form, which is capable of transferring electron energy from a normal hydrogen carrier to a nucleic acid. Such lipoic acid derivatives include, without limitation, lipoic acid analogues having a shortened or lengthened carbon chain, e.g., the lipoic acid derivative may comprise a carbon chain of at least 2 carbon atoms. According to some such embodiments, the lipoic acid derivative comprises a $C_2$ to $C_{20}$ hydrocarbon chain. According to some such embodiments, the lipoic acid derivative comprises a $C_2$ hydrocarbon chain, a $C_3$ hydrocarbon chain, a $C_4$ hydrocarbon chain, a $C_5$ hydrocarbon chain, a $C_6$ hydrocarbon chain, a $C_7$ hydrocarbon chain, a $C_8$ hydrocarbon chain, a $C_9$ hydrocarbon chain, a $C_{10}$ hydrocarbon chain, a $C_{11}$ hydrocarbon chain, a $C_{12}$ hydrocarbon chain, a $C_{13}$ hydrocarbon chain, a $C_{14}$ hydrocarbon chain, a $C_{15}$ hydrocarbon chain, a $C_{16}$ hydrocarbon chain, a $C_{17}$ hydrocarbon chain, a $C_{18}$ hydrocarbon chain, a $C_{19}$ hydrocarbon chain, or a $C_{20}$ hydrocarbon chain. According to some embodiments, the lipoic acid derivative comprises one to three additional side groups, for example, without limitation, a carboxyl group, a sulfur group, an amino group, or a combination thereof. The side groups may be attached, for example, to one of the sulfur atoms, along the carbon chain, or may be substituted for the hydroxyl group at the carbonyl end of the lipoic acid moiety. According to one embodiment, the lipoic acid derivative is lipoamide. According to one embodiment, the lipoic acid derivative comprises a side group selected from a carboxyl, a sulfur, an amine or a combination thereof.

Fatty Acid Component

The complex of the invention contains a $C_2$ to $C_{20}$ fatty acid component. Any fatty acid can be utilized in the complex, as long as the fatty acid is able to bond effectively to the palladium via its carboxyl end, and to bond to zinc via its methyl end.

Fatty acid carbon atoms are numbered starting at the carboxy terminal end:

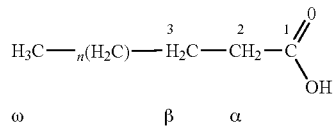

Carbon atoms 2 and 3 often are referred to as α and β, respectively. The methyl carbon at the distal end of the chain is called the ω carbon.

According to some embodiments, the fatty acid component is saturated, meaning it contains no double bonds. According to some embodiments, the fatty acid component is unsaturated, meaning it contains at least one double bond. The position of a double bond may be represented by the symbol Δ followed by a superscript number. According to one embodiment, the fatty acid is docosahexaenoic acid. According to one embodiment, the fatty acid component is the $C_{18}$ fatty acid containing two double bonds, linoleic acid (octadecadienoate). For example, a $C_{18}$ fatty acid with one double bond is oleate or octadecenoic acid, with two double bonds is octadecadienoic acid, or linoleic acid, and with three double bonds is linolenate, or octadecatrienoic acid. The symbol 18:0 denotes a $C_{18}$ fatty acid with no double bonds, whereas 18:2 signifies that there are two double bonds.

Zinc Component

The complex of the invention further contains a zinc component comprising the nontransition metal element zinc. According to one embodiment, the zinc component is bonded to the ω carbon of the fatty acid component According to another embodiment, the zinc component is bonded to one or both amino acids of the amino acid component. The zinc component can be in the form of elemental zinc, or in the form of a derivative of zinc including, without limitation, zinc carbonate, zinc gluconate, zinc chloride, zinc pyrithione, zinc sulfide, zinc methyl or zinc diethyl.

Amino Acid Component:

The terms "amino acid component", "amino acid residue", "amino acid" or "residue" are used interchangeably to refer to an amino acid (meaning an organic acid in which one of the hydrogen atoms on a carbon atom has been replaced by $NH_2$) that is incorporated into the complex of the described invention, including, but not limited to, a naturally occurring amino acid and known analogs of natural amino acids that can function in a similar manner as naturally occurring amino acids. When utilized to denote an amino acid, the abbreviations for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acid may be an L- or D-amino acid. An amino acid may be replaced by a synthetic amino acid. When the complex comprises two amino acid residues, the two amino acids are the same amino acid or two different amino acids.

Optional Additional Ligand:

According to one embodiment, the organometallic complex of the described invention further comprises at least one ligand. According to some embodiments, the at least one ligand is selected from an inorganic anionic ligand or an inorganic cationic ligand. Exemplary inorganic anionic ligands, include without limitation acetate, acetylacetonate, amine, ammonium chloride, ammonium nitrate, bromide, chloride, fluoride, iodide, nitrate, nitrite, oxalate, oxide, pyridine, sulfate and sulfide. Exemplary cationic ligands include, but are not limited to, sodium, potassium, magnesium, calcium, ammonia, vanadate, molybdate, zinc, tin, etc.

According to one embodiment, the ligand can be bound to any component of the organiometallic complex.

Optional Additives:

According to one embodiment, the organometallic complex of the described invention further comprise at least one additive. Exemplary additives include, without limitation, glycine, hyaluronic acid, etc.

Structural Properties:

According to one embodiment, the organometallic complex crystallizes to form an octahedrally shaped crystal. According to one embodiment, the organometallic complex is monomolecular.

According to some embodiments, the complexes of the invention can be identified using UV-visible spectroscopy, by cyclic voltammetry, and by Fourier transform-infrared spectroscopy (FTIR).

The complex of the invention may exist in a form including in a solid form, in a liquid form as a dispersion, suspension, or as a solution. In a solution, the molecules of the solute (or dissolved substance) are uniformly distributed among those of the solvent (the substance capable of dissolving another substance). A dispersion is a mixture of constituent species. A "suspension" is a dispersion in which a finely-divided species is combined with another species, with the former being so finely divided and mixed that it doesn't rapidly settle out.

As is common in metal to ligand syntheses, multiple complexes may be produced.

Functional Properties

According to one embodiment, the organometallic complex is capable of spin transfer.

According to one embodiment, the organometallic complex has an electropositive standard potential. According to one embodiment, the organometallic complex is an oxidized form of the complex. According to one embodiment, the organometallic complex is a reduced form of the complex. Whether the oxidized or reduced form is favored will depend upon the pH of the particular solution containing the complex, and the value of the standard potential of the described organometallic complex, governed by the Nernst equation.

According to one embodiment, the organometallic complex is thermodynamically stable.

According to another aspect, the described invention provides a coordinate alloy comprising:

(a) an organometallic complex of Formula I:

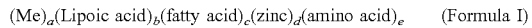

(Me)$_a$(Lipoic acid)$_b$(fatty acid)$_c$(zinc)$_d$(amino acid)$_e$ (Formula I)

wherein

ME signifies a metal;

the Me component contains a palladium component and a ruthenium component;

the lipoic acid component comprises lipoic acid or a derivative thereof, wherein the lipoic acid component comprises at least two sulfur atoms and at least one carboxyl group;

the fatty acid component comprises a hydrocarbon chain of from 2 to twenty carbon atoms wherein at one end of the hydrocarbon chain is a methyl group and at the other end is a carboxyl group; and the zinc component is bonded to a methyl group at one end of the fatty acid, wherein a is at least 2;

b, and c are each 1;

d is 0 or 1;

e is 0, 1, or 2, and when e is 2, the amino acid component comprises a first amino acid and a second amino acid, wherein the first amino acid is bonded to the zinc component, and the second amino acid is bonded to the fatty acid component;

wherein the palladium component is bonded to the lipoic acid component via both sulfur atoms and by the carboxyl group oxygens of the lipoic acid component;

the fatty acid is bonded to the palladium via the carboxyl group of the fatty acid; and the ruthenium component is bonded to the amino acid that is bonded to the zinc component; and (b) at least one additive.

(a) An Organometallic Complex

According to one embodiment, the organometallic complex comprises an organified ruthenium component comprising a ruthenium component and at least one organyl component, wherein the ruthenium component is bonded to the organyl component. According to one embodiment, the organyl component comprises a first amino acid component. According to one such embodiment, the first amino acid component is N-formyl methionine.

According to one embodiment, the complex comprises an organified palladium component comprising a palladium component and at least one organyl component, wherein the palladium component is bonded to the organyl component. According to one embodiment, the organyl component comprises lipoic acid or a derivative thereof. According to one embodiment, the organyl component comprises a fatty acid component or a derivative thereof. According to one embodiment, the fatty acid component comprises a hydrocarbon chain of from 2 to twenty carbon atoms, wherein at one end of the hydrocarbon chain (the ω carbon) is a methyl group and at the α carbon on the other end is a carboxyl group. According to one embodiment, the fatty acid component is linoleic acid or a derivative thereof. According to one embodiment, the at least one organyl component comprises a second amino acid component. According to one such embodiment, the amino acid component is arginine. According to one embodiment, the fatty acid derivative is a linoleic acid to which the arginine is linked. According to one embodiment, the arginine facilitates water solubility of the linoleic acid.

According to one embodiment, the organified palladium component is bonded to the organified ruthenium component via a zinc component, wherein the first amino acid component is formyl methionine, and the second amino acid component is arginine. According to one embodiment, arginine functions as a charge donor. According to one embodiment, the complex is monomolecular in nature. According to one embodiment, the complex is capable of charge transfer. According to one embodiment, when a connecting bond between organified palladium and organified ruthenium is accomplished using both a fatty acid (linoleic acid), and zinc, amino acid 1 is formyl methionine, and amino acid 2 is the charge donor arginine, the complex is referred to as GML-X3. An exemplary general structure of GML-X3, a monomolecular charge transfer organo-metallic complex containing two transition metals palladium, ruthenium, and the nontransition metal zinc is shown in FIG. 16. The organometallic complex of GML-X3 comprises an organified palladium component that is referred to as G10, and an organified ruthenium component that is referred to Ru-formyl methionine. In the GML-X3 complex, the G10 component is bonded to the Ru-formyl methionine component via a zinc component.

According to one embodiment, GML-X3 is assembled from a plurality of precursor chemical entities to produce a single monomolecular complex. According to one embodiment, the precursor chemical entity comprises an organified ruthenium component comprising a ruthenium component and at least one organyl group, wherein the ruthenium component is bonded to the at least one organyl group. According to one such embodiment, the at least one organyl group comprises a first amino acid. According to one such embodiment, the first amino acid is formyl methionine. According to one embodiment, the precursor chemical entity comprises an organified palladium component, comprising a palladium-lipoic acid complex bonded to at least one organyl group. According to one such embodiment, the palladium-lipoic acid complex comprises a palladium component and a lipoic acid component, wherein the palladium component is bonded to the lipoic acid component via both sulfur atoms and by the carboxyl group oxygens of the lipoic acid component. According to one such embodiment, the at least one organyl group is a fatty acid. According to one such embodiment, the at least one organyl group comprises a second amino acid. According to one such embodiment, the second amino acid is arginine. According to another embodiment, integrated electronic transport of the single GML-X3 complex enables spin transfer.

Palladium Component

Palladium is a transition metal of Group 10 of the periodic table. According to some embodiments, the palladium component is selected from elemental palladium or a palladium salt. According to one embodiment, the palladium component is in the form of elemental palladium. According to one embodiment, the palladium component is a palladium salt. According to another embodiment, a palladium salt is employed in preparing the organified palladium component of the described invention. Such palladium salts include, without limitation, palladium acetate, palladium acetylacetonate, palladium ammonium chloride, palladium ammonium nitrate, palladium bromide, palladium chloride, palladium diamine nitrite, palladium diamylamine nitrite, palladium dibromide, palladium difluoride, palladium dioxide, palladium dipyridine nitrite, palladium ethylenediamine nitrite, palladium iodide, palladium monoxide, palladium nitrate, palladium oxalate, palladium oxide, palladium sulfate, palladium sulfide, palladium tetramine dichloride, palladous potassium bromide, palladous potassium chloride, palladous sodium bromide, and palladous sodium chloride. According to some such embodiments, the palladium salt is palladium chloride, palladium bromide, palladium iodide, palladium nitrate, palladium oxide or palladium sulfide. According to some such embodiments, the palladium salt is palladium chloride.

Ruthenium Component

Ruthenium is a transition metal of Group 8 of the periodic table. According to some embodiments, the ruthenium component is selected from elemental ruthenium or a ruthenium salt. According to one embodiment, the ruthenium component is in the form of elemental ruthenium. According to another embodiment, a ruthenium salt is employed in preparing the organified ruthenium component of the described invention. Such ruthenium salts include, without limitation, ruthenium acetate, ruthenium acetylacetonate, ruthenium ammonium chloride, ruthenium ammonium nitrate, ruthenium bromide, ruthenium chloride, ruthenium diamine nitrite, ruthenium diamylamine nitrite, ruthenium dibromide, ruthenium difluoride, ruthenium dioxide, ruthenium dipyridine nitrite, ruthenium ethylenediamine nitrite, ruthenium iodide, ruthenium monoxide, ruthenium nitrate, ruthenium oxalate, ruthenium oxide, ruthenium sulfate, ruthenium sulfide, ruthenium tetramine dichloride, ruthenium potassium bromide, ruthenium potassium chloride, ruthenium sodium bromide, and ruthenium sodium chloride. According to some such embodiments, the ruthenium salt is ruthenium chloride, ruthenium bromide, ruthenium iodide, ruthenium nitrate, ruthenium oxide or ruthenium sulfide. According to some such embodiments, the ruthenium salt is ruthenium chloride.

Lipoic Acid Component:

Lipoic acid and its derivatives are highly specific for transferring electron energy from a normal metabolic hydrogen carrier to nucleic acids. Lipoic acid has a long, flexible side chain, which enables it to rotate from one active site to another in enzyme complexes. As shown in Campbell et al, Biochemistry Illustrated, 2d, Churchill Livingstone, 126 (1988), lipoic acid is a hydrogen carrier and an acetyl-group carrier for the decarboxylation of pyruvic acid. Lipoic acid is then present as acetyllipoic acid, having both an acetyl group and a hydrogen atom. In the pyruvic decarboxylation reaction, the acetyl group is donated to CoA and the H is donated to NAD+.

According to one embodiment the lipoic acid component comprises at least two sulfur atoms, a hydrocarbon chain having a length of two to twenty carbon atoms, and one or more carboxyl groups. According to one embodiment, the lipoic acid component is in its reduced or dithiol form. According to another embodiment, the lipoic acid component is in its oxidized or disulfide form. Whether the oxidized or reduced form is favored will depend upon the pH of the solution containing the complex.

According to some embodiments, the lipoic acid component is a derivative of lipoic acid, in either its oxidized or reduced form, that is capable of transferring electron energy from a normal hydrogen carrier to a nucleic acid Such lipoic acid derivatives include lipoic acid analogues having a shortened or lengthened carbon chain, e.g., the lipoic acid derivative may comprise a carbon chain of at least 2 carbon atoms. According to some such embodiments, the lipoic acid derivative comprises a $C_2$ to $C_{20}$ hydrocarbon chain. According to some embodiments, the lipoic acid derivative comprises a $C_2$ hydrocarbon chain, a $C_3$ hydrocarbon chain, a $C_4$ hydrocarbon chain, a $C_5$ hydrocarbon chain, a $C_6$ hydrocarbon chain, a $C_7$ hydrocarbon chain, a $C_8$ hydrocarbon chain, a $C_9$ hydrocarbon chain, a $C_{10}$ hydrocarbon chain, a $C_{11}$ hydrocarbon chain, a $C_{12}$ hydrocarbon chain, a $C_{13}$ hydrocarbon chain, a $C_{14}$ hydrocarbon chain, a $C_{15}$ hydrocarbon chain, a $C_{16}$ hydrocarbon chain, a $C_{17}$ hydrocarbon chain, a $C_{18}$ hydrocarbon chain, a $C_{19}$ hydrocarbon chain, or a $C_{20}$ hydrocarbon chain. According to some embodiments the lipoic acid derivative comprises one to three additional side groups, for example, without limitation, a carboxyl group, a sulfur group, an amino group, or a combination thereof. The side groups may be attached, for example, to one of the sulfur atoms, along the carbon chain, or may be substituted for the hydroxyl group at the carbonyl end of the lipoic acid moiety. According to one embodiment, the lipoic acid derivative is lipoamide. According to one embodiment, the lipoic acid derivative comprises a side group selected from a carboxyl, a sulfur, an amine or a combination thereof.

Fatty Acid Component

The complex of the invention contains a $C_2$ to $C_{20}$ fatty acid component. Any fatty acid can be utilized in the complex, as long as the fatty acid is able to bond effectively to the palladium via its carboxyl end, and to bond to zinc via its methyl end.

Fatty acid carbon atoms are numbered starting at the carboxy terminal end:

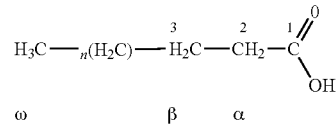

Carbon atoms 2 and 3 often are referred to as α and β, respectively. The methyl carbon at the distal end of the chain is called the ω carbon.

According to some embodiments, the fatty acid component is saturated, meaning it contains no double bonds. According to some embodiments, the fatty acid component is unsaturated, meaning it contains at least one double bond. The position of a double bond may be represented by the symbol Δ followed by a superscript number. According to one embodiment, the fatty acid is docosahexaenoic acid. According to one embodiment, the fatty acid component is the $C_{18}$ fatty acid containing two double bonds, linoleic acid (octadecadienoate). For example, a $C_{18}$ fatty acid with one double bond is oleate or octadecenoic acid, with two double bonds is octadecadienoic acid, or linoleic acid, and with three double bonds is linolenate, or octadecatrienoic acid. The symbol 18:0 denotes a $C_{18}$ fatty acid with no double bonds, whereas 18:2 signifies that there are two double bonds.

Zinc Component

The complex of the invention further contains a zinc component comprising the nontransition metal element zinc. According to one embodiment, the zinc component is bonded to the ω carbon of the fatty acid component According to another embodiment, the zinc component is bonded to at least one amino acid of the amino acid component. The zinc component can be in the form of elemental zinc, or in the form of a derivative of zinc including, without limitation, zinc carbonate, zinc gluconate, zinc chloride, zinc pyrithione, zinc sulfide, zinc methyl or zinc diethyl.

Amino Acid Component:

The terms "amino acid component", "amino acid residue", "amino acid" or "residue" are used interchangeably to refer to an amino acid that is incorporated into the complex of the described invention, including, but not limited to, a naturally occurring amino acid and known analogs of natural amino acids that can function in a similar manner as naturally occurring amino acids. When utilized to denote an amino acid, the abbreviations for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=lsoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acid may be an L- or D-amino acid. An amino acid may be replaced by a synthetic amino acid. When the complex comprises two amino acid residues, the two amino acids are the same amino acid or two different amino acids.

Optional Additional Ligand:

According to one embodiment, the organometallic complex of the described invention further comprises at least one ligand. According to some embodiments, the at least one ligand is selected from an inorganic anionic ligand or a cationic ligand. Exemplary inorganic anionic ligands, include without limitation acetate, acetylacetonate, amine, ammonium chloride, ammonium nitrate, bromide, chloride, fluoride, iodide, nitrate, nitrite, oxalate, oxide, pyridine, sulfate and sulfide. Exemplary cationic ligands include, but are not limited to, sodium, potassium, magnesium, calcium, ammonia, vanadate, molybdate, zinc, tin, etc.

According to one embodiment, the ligand can be bound to any component of the organometallic complex.

Structural Properties of the Organometallic Complex:

According to one embodiment, the organometallic complex crystallizes to form an octahedrally shaped crystal. According to one embodiment, the organometallic complex is monomolecular.

According to some embodiments, the complexes of the invention can be identified using UV-visible spectroscopy, by cyclic voltammetry, and by Fourier transform-infrared spectroscopy (FTIR).

The complex of the invention may exist in a form including in a solid form, in a liquid form as a dispersion, suspension, or as a solution.

As is common in metal to ligand syntheses, multiple complexes may be produced.

Functional Properties of the Organometallic Complex

According to one embodiment, the organometallic complex is capable of spin transfer.

According to one embodiment, the organometallic complex has an electropositive standard potential. According to one embodiment, the organometallic complex is an oxidized form of the complex. According to one embodiment, the organometallic complex is a reduced form of the complex. Whether the oxidized or reduced form is favored will depend upon the pH of the particular solution containing the complex, and the value of the standard potential of the described organometallic complex, governed by the Nernst equation.

According to one embodiment, the organometallic complex is thermodynamically stable.

(b) At Least One Additive:

Exemplary additives include, but are not limited to, glycine, etc.

Properties of the Coordinate Alloy

Without being limited by theory, the coordinate alloy comprising the organometallic complex exhibits vortex pinning. The aggregate structure can be compared conceptually to solid state alloys. The contribution of vortex pinning to alloying had been suggested. (Blatter, G., et al., "Aspects of vortex pinning, Swiss Federal Institute of Technology—web posting, ETH Zurich, 20092).

The coordinate alloys of the present invention are distinct solid state alloys but share certain similar properties with alloys of hydrotalcite group which are multi-metal compounds with double layers of hydroxyls. (Nalawade, P. et al., "Layered double hydroxides: a review," J. Scientific and Industrial Research, 68: 267-272 (2009); Kloprogge J. T. et al., "FT-Raman and FT-IR spectroscopic study of synthetic Mg/Zn/Al-hydrotalcites," J. Raman Spectroscopy, 35: 967-974 (2004)).

Pharmaceutical Compositions Comprising an Organometallic Complex

According to another aspect, the described invention provides a pharmaceutical composition comprising:

(i) an organometallic complex of Formula I:

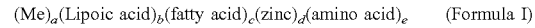

$(Me)_a(Lipoic\ acid)_b(fatty\ acid)_c(zinc)_d(amino\ acid)_e$ (Formula I)

wherein

Me signifies a metal;

the Me component contains a palladium component and a ruthenium component;

the lipoic acid component comprises lipoic acid or a derivative thereof, wherein the lipoic acid component comprises at least two sulfur atoms and at least one carboxyl group;

the fatty acid component comprises a hydrocarbon chain of from 2 to twenty carbon atoms wherein at one end of the hydrocarbon chain is a methyl group and at the other end is a carboxyl group; and the zinc component is bonded to a methyl group at one end of the fatty acid component, wherein a is at least 2;

b, and c are each 1;

d is 0 or 1;

e is 0, 1, or 2, and when e is 2, the amino acid component comprises a first amino acid and a second amino acid, wherein the first amino acid is bonded to the zinc component, and the second amino acid is bonded to the fatty acid component;

wherein the palladium component is bonded to the lipoic acid component via both sulfur atoms and by the carboxyl group oxygens of the lipoic acid component;

the fatty acid is bonded to the palladium via the carboxyl group of the fatty acid; and the ruthenium component is bonded to the amino acid that is bonded to the zinc component; and (ii) a pharmaceutically acceptable carrier.

The organometallic complex, the palladium component, the ruthenium component, the lipoic acid component, the fatty acid component, the zinc component, and the amino acid component are as have been described above.

According to one embodiment, the organometallic complex of the described invention further comprises at least one ligand. According to one embodiment, the organometallic complex of the described invention further comprises at least one additive. The ligand and the additive are as have been described above.

Structural and functional properties of the organometallic complex are as have been described above.

(ii) Pharmaceutically Acceptable Carrier

In some embodiments, the pharmaceutical composition can be formulated with an excipient, carrier or vehicle including, but not limited to, a solvent. The terms "excipient", "carrier", or "vehicle" as used herein refers to carrier materials suitable for formulation and administration of the chemotactic hematopoietic stem cell product described herein. Carriers and vehicles useful herein include any such materials know in the art which are nontoxic and do not interact with other components. As used herein the phrase "pharmaceutically acceptable carrier" refers to any substantially non-toxic carrier useable for formulation and administration of the composition of the described invention in which the organometallic complex of the described invention will remain stable and bioavailable.

The pharmaceutically acceptable carrier must be of sufficiently high purity and of sufficiently low toxicity to render it suitable for administration to the mammal being treated. It further should maintain the stability and bioavailability of the organometallic complex. The pharmaceutically acceptable carrier can be liquid or solid and is selected, with the planned manner of administration in mind, to provide for the desired bulk, consistency, etc., when combined with an active agent and other components of a given composition. For example, the pharmaceutically acceptable carrier may be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions of the described invention include, but are not limited to, water, buffers, salt solutions, alcohols, polyethylene glycols, gelatins, amyloses, magnesium stearates, talcs, silicic acids, viscous paraffins, hydroxymethylcelluloses, polyvinylpyrrolidones and the like. Such carrier solutions also can contain buffers, diluents and other suitable additives. The term "buffer" as used herein refers to a solution or liquid whose chemical makeup neutralizes acids or bases without a significant change in pH. Examples of buffers envisioned by the described invention include, but are not limited to, Dulbecco's phosphate buffered saline (PBS), Ringer's solution, 5% dextrose in water (D5W), and normal/physiologic saline (0.9% NaCl). In some embodiments, the infusion solution is isotonic to subject tissues. In some embodiments, the infusion solution is hypertonic to subject tissues.

Administration

In general, the pharmaceutical compositions of the present invention may be formulated by any means known in the art, including not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. Any route of administration by which provided compositions of the invention are introduced across an epidermal layer of cells may be employed. The pharmaceutical compositions of the present invention may be administered by any enteral or parenteral route. Administration routes may thus include administration through mucous membranes, enteral administration, parenteral administration, topical administration, inhalation administration, pulmonary administration, nasal administration, and the like.

Enteral administration includes any suitable form for oral consumption including, for example, tablets, pills, liquid gels, capsules, elixir, and troches. For instance, for oral administration in the form of tablets or capsules, the active drug components may be combined with any oral non-toxic pharmaceutically acceptable inert carrier such as starch, cellulose, magnesium stearate, dicalcium phosphate, calcium sulfate, mannitol, and the like. Moreover, when desired or necessary, suitable binders, lubricants, disintegrating agents and coloring agents can also be incorporated in the mixture. Suitable binders, for example, include starch, gelatin, natural and synthetic gums such as acacia, sodium alginate, carboxymethylcellulose, polyethylene glycol and waxes. Among the lubricants, there may be mentioned for use in these dosage forms, boric acid, sodium benzoate, sodium acetate, sodium chloride, etc. Disintegrators include, without limitation, starch, methylcellulose, agar, bentonite, guar gum, etc. Flavoring agents and preservatives can also be included where appropriate. In the case of tablets, they can be further coated with the usual coating materials to make, for example, sugar-coated tablets, gelatin film-coated tablets, tablets coated with enteric coatings, tablets coated with films or double-layered and multi-layer tablets.

The pharmaceutical composition of the described invention may be a sterile solution or suspension in a nontoxic parenterally acceptable diluent or solvent. A solution generally is considered as a homogeneous mixture of two or more substances; it is frequently, though not necessarily, a liquid. In a solution, the molecules of the solute (or dissolved substance) are uniformly distributed among those of the solvent. A suspension is a dispersion (mixture) in which a finely-divided species is combined with another species, with the former being so finely divided and mixed that it does not rapidly settle out. In everyday life, the most common suspensions are those of solids in liquid water. Among the acceptable vehicles and solvents that may be employed are water, Ringer's solution, and isotonic sodium chloride (saline) solution. In some embodiments, hypertonic solutions are employed. In addition, sterile, fixed oils conventionally are employed as a solvent or suspending medium. For parenteral application, suitable vehicles consist of solutions, e.g., oily or aqueous solutions, as well as suspensions, emulsions, or implants. Aqueous suspensions may contain substances, which increase the viscosity of the suspension and include, for example, sodium carboxymethyl cellulose, sorbitol and/or dextran. The aqueous sterile injectable solutions may further contain anti-oxidants, buffers, bacteriostats, isotonicity adjusters and like additions acceptable for parenteral formulations. Parental administration includes intravenous, intramuscular, subcutaneous, intradermal, topical, intra-thecal and intra-arterial methods. Compositions of the described invention that are for parenteral administration may include pharmaceutically acceptable carriers such as sterile aqueous solutions, non-aqueous solutions in common solvents such as alcohols, or solutions in a liquid oil base.

Formulations of the present invention suitable for topical application to the skin take the form of an ointment, cream, lotion, paste, gel, spray, aerosol, transdermal device or oil. Additives which may be used include vaseline, lanolin, polyethylene glycols, alcohols, transdermal enhancers, and combinations of two or more thereof. Transdermal pharmaceutical devices include patches, occlusive dressings, occlusive formulations, hypodermic sprays, iontophoretic systems, gels and infusion pumps, all of which are well known in the art. A transdermal patch which includes a pharmaceutical may generally include a backing layer impermeable to the pharmaceutical, a reservoir to house the pharmaceutical, and an adhesive cover to be removed upon use of the patch and for adhesion to the skin of a patient. Formulations suitable for transdermal administration may also be presented as medicated bandages or discrete patches adapted to remain in intimate contact with the epidermis of the recipient for a prolonged period of time. Representative examples of suitable transdermal patches include, for example, those developed by NeuroDerm Ltd (Israel) and/or that used to deliver estradiol, for example, those developed by Novogyne Pharmaceuticals. Formulations suitable for transdermal administration may also be delivered by iontophoresis (passage of a small electric current (about 15 mA) to "inject" electrically charged ions into the skin) through the skin. For this, the dosage form typically takes the form of an optionally buffered aqueous solution of the active compound. Formulations suitable for transdermal administration may also be delivered by using an infusion pump connected to a needle that is inserted through the skin, for example, those developed by Medtronic used to deliver insulin. Amounts used in a transdermal device as described herein may vary, depending on many factors including the size of the device and its release characteristics, the amount of the pharmaceutical active agent and the estimated duration of action of the device.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose in accordance with the invention.

In some embodiments, the carrier may include a release agent such as a sustained release or delayed release carrier. In such embodiments, the carrier may be any material capable of sustained or delayed release of the active to provide a more efficient administration, e.g., resulting in less frequent and/or decreased dosage of the composition, improve ease of handling, and extend or delay effects on diseases, disorders, conditions, syndromes, and the like, being treated, prevented or promoted. Non-limiting examples of such carriers include liposomes, microsponges, microspheres, or microcapsules of natural and synthetic polymers and the like. Liposomes may be formed from a variety of phospholipids such as cholesterol, stearylamines or phosphatidylcholines.

The pharmaceutical compositions of the described invention may be administered parenterally in the form of a sterile injectable aqueous or oleaginous suspension. The term "parenteral" or "parenterally" as used herein refers to introduction into the body by way of an injection (i.e., administration by injection), including, but not limited to, infusion techniques.

Various unit dose and multidose containers, e.g., sealed ampules and vials, may be used, as is well-known in the art. The essential ingredients of the sterile parenteral formulation, e.g., the water and the organometallic complex, may be presented in a variety of ways, as long as the solution ultimately administered to the patient contains the appropriate amounts of the essential ingredients. Thus, for example, the organometallic complex/water formulation may be presented in a unit dose or multidose container, ready for injection. As another example, a concentrated solution of the organometallic complex/water may be presented in a separate container from a diluting liquid (water or organometallic complex/water) designed so that the contents can be combined to give a formulation containing appropriate amounts for injection. As another alternative, the organometallic complex may be provided in a freeze-dried condition in one container, while a separate container contains diluting liquid (water or organometallic complex/water, depending on the amount of organometallic complex in the other container), again designed so that the contents can be combined to give a formulation containing the appropriate amounts of the water and selected organometallic complex. In any event, the contents of each container will be sterile. Suitable carriers for parenteral administration include, for example, water, ethyl alcohol, propylene glycol, ethoxylated isostearyl alcohol, polyoxylated isostearyl alcohol, polyoxyethylene sorbitol and sorbitate esters. In these instances, adequate amounts of sodium chloride, glucose or glycerin can be added to make the preparations isotonic.

Additionally, pharmaceutical compositions of the described invention may be prepared using technology, which is known in the art, such as described in Remington's Pharmaceutical Sciences, 18th or 19th editions, published by the Mack Publishing Company of Easton, Pa., which is incorporated herein by reference.

A skilled artisan may determine the therapeutic amount of the inventive compositions by determining the dose in a dosage unit (meaning unit of use) that elicits a given intensity of effect, hereinafter referred to as the "unit dose." The term "dose-intensity relationship" refers to the manner in which the intensity of effect in an individual recipient relates to dose. The intensity of effect generally designated is 50% of maximum intensity. The corresponding dose is called the 50% effective dose or individual ED50. The use of the term "individual" distinguishes the ED50 based on the intensity of effect as used herein from the median effective dose, also abbreviated ED50, determined from frequency of response data in a population. "Efficacy" as used herein refers to the property of the compositions of the described invention to achieve the desired response, and "maximum efficacy" refers to the maximum achievable effect. The therapeutic amount of the pharmaceutical compositions of the described invention that will be effective in the treatment of a particular disorder or condition will depend on the nature of the disorder or condition, and may be determined by standard clinical techniques. (See, for example, Goodman and Gilman's THE PHARMACOLOGICAL BASIS OF THERAPEUTICS, Joel G. Harman, Lee E. Limbird, Eds.; McGraw Hill, New York, 2001; THE PHYSICIAN'S DESK REFERENCE, Medical Economics Company, Inc., Oradell, N.J., 1995; and DRUG FACTS AND COMPARISONS, FACTS AND COMPARISONS, INC., St. Louis, Mo., 1993), each of which is incorporated by reference herein. The precise dose to be employed in the formulations of the described invention also will depend on the route of administration and the seriousness of the disease or disorder, and should be decided according to the judgment of the practitioner and each subject's circumstances.

The terms "therapeutic amount", "therapeutic effective amount" or an "amount effective" of one or more of the therapeutic agents is an amount that is sufficient to provide the intended benefit of treatment. According to one embodiment, the therapeutic amount has an anti-inflammatory effect. According to one embodiment, the anti-inflammatory effect comprises detoxification of a plurality of free radicals. The term "detoxification" as used herein refers to lowering of the level of free radicals such that their toxic effects are reduced. Detoxification includes, but is not limited to, depolarization of a plurality of free radicals. According to one embodiment, the anti-inflammatory effect comprises depolarization of a free radical. According to one such embodiment, the free radicals are reaction oxygen species. Exemplary reactive oxygen species include, but are not limited to, superoxide anion ($O_2^{\cdot-}$), peroxide ($O_2^{\cdot-2}$), hydroxyl radical (.OH), and singlet oxygen ($^1O_2$). The anti-inflammatory effect may be curing, minimizing, preventing or ameliorating an inflammatory disease or disorder, or may have any other adverse consequence reversing, or pharmaceutical beneficial effect. The concentration of the substance is selected so as to exert its therapeutic effect, but low enough to avoid significant side effects within the scope and sound judgment of the physician. The effective amount of the composition may vary with the age and physical condition of the biological subject being treated, the severity of the condition, the duration of the treatment, the nature of concurrent therapy, the timing of the infusion, the specific compound, composition or other active ingredient employed, the particular carrier utilized, and like factors.

For example, when the pharmaceutical composition of the present invention is parenterally administered to a patient, a dosage of between about 0.1 mL to 5 mL daily of a 25 mg/mL solution of the pharmaceutical composition for at least about 5-7 days is employed. A contemplated dosage pattern in adult humans is about 0.5 mL of 25 mg/mL of the composition administered daily for the first three days of treatment, followed by 0.3 mL daily for an additional 7 days of treatment. However, the precise route of administration, dosage and frequency of administration is individualized for each patient and can vary over a wide range depending on the particular disease state being treated, the condition of the patient and the like.

According to one embodiment, the complex in solution is present in an amount amount sufficient to produce a therapeutic effect after administration.

Methods of Treatment

According to another aspect, the described invention provides a method of treating an inflammatory disease or condition in a mammal, comprising:
a) providing a pharmaceutical composition comprising:
   (i) an organometallic complex of Formula I:

$$(Me)_a(Lipoic\ acid)_b(fatty\ acid)_c(zinc)_d(amino\ acid)_e \quad (Formula\ I)$$

wherein
Me signifies a metal;
the Me component contains a palladium component and a ruthenium component;
the lipoic acid component comprises lipoic acid or a derivative thereof, wherein the lipoic acid component comprises at least two sulfur atoms and at least one carboxyl group;
the fatty acid component comprises a hydrocarbon chain of from 2 to twenty carbon atoms wherein at one end of the hydrocarbon chain is a methyl group and at the other end is a carboxyl group; and
the zinc component is bonded to a methyl group at one end of the fatty acid,
wherein
a is at least 2;
b, and c are each 1;
d is 0 or 1;
e is 0, 1, or 2, and when e is 2, the amino acid component comprises a first amino acid and a second amino acid, wherein the first amino acid is bonded to the zinc component, and the second amino acid is bonded to the fatty acid component;
wherein the palladium component is bonded to the lipoic acid component via both sulfur atoms and by the carboxyl group oxygens of the lipoic acid component;
the fatty acid is bonded to the palladium via the carboxyl group of the fatty acid; and
the ruthenium component is bonded to the amino acid that is bonded to the zinc component; and
   (ii) a pharmaceutically acceptable carrier; and
b) administering a therapeutic amount of the pharmaceutical composition to the mammal such that the therapeutic amount has an anti-inflammatory effect.

In general, the pharmaceutical compositions of the present invention may be administered as described above. According to one embodiment, the complex in solution is present in an amount amount sufficient to produce a therapeutic effect after administration.

According to one embodiment, the organometallic complex of formula I comprises a coordinate alloy, wherein the coordinate alloy comprises at least one additive.

The organometallic complex, the palladium component, the ruthenium component, the lipoic acid component, the fatty acid component, the zinc component, and the amino acid component are as have been described above.

According to one embodiment, the organometallic complex of the described invention further comprise at least one ligand. According to one embodiment, the organometallic complex of the described invention further comprise at least one additive. The ligand and the additive are as have been described above.

Structural and functional properties of the organometallic complex are as have been described above.

Inflammation

Inflammation is the physiologic process by which vascularized tissues respond to injury. It is a protective response by the body to ensure removal of detrimental stimuli, as well as a healing process for repairing damaged tissue. See, e.g., FUNDAMENTAL IMMUNOLOGY, 4th Ed., William E. Paul, ed. Lippincott-Raven Publishers, Philadelphia (1999) at 1051-1053; and Takeuchi, O. and Akira, S., "Pattern recognition receptors and inflammation," Cell 140(6): 805-820 (2010), incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "acute inflammation" as used herein refers to the rapid, short-lived (minutes to days), relatively uniform response to acute injury characterized by accumulations of fluid, plasma proteins, and neutrophilic leukocytes. Examples of injurious agents that cause acute inflammation include, but are not limited to, pathogens (e.g., bacteria, viruses, parasites), foreign bodies from exogenous (e.g. asbestos) or endogenous (e.g., urate crystals, immune complexes), sources, and physical (e.g., burns) or chemical (e.g., caustics) agents. Tissue damage results in the release of intracellular damage-associated molecular patterns (DAMPs) usually hidden from the immune system (e.g., ATP, uric acid, lipids, DNA nuclear proteins), or extracellular DAMPs released through degradation of extracellular matrix upon tissue injury (e.g., hyaluronan, byglycan, heparan sulfate).

In contrast, the term "chronic inflammation" as used herein refers to inflammation that is of longer duration and which has a vague and indefinite termination. Chronic inflammation takes over when acute inflammation persists, either through incomplete clearance of the initial inflammatory agent or as a result of multiple acute events occurring in the same location. Chronic inflammation, which includes the influx of lymphocytes and macrophages and fibroblast growth, may result in tissue scarring at sites of prolonged or repeated inflammatory activity.

Regardless of the initiating agent, the physiologic changes accompanying acute inflammation encompass four main features: (1) vasodilation, which results in a net increase in blood flow, is one of the earliest s physical responses to acute tissue injury; (2) in response to inflammatory stimuli, endothelial cells lining the venules contract, widening the intracellular junctions to produce gaps, leading to increased vascular permeability, which permits leakage of plasma proteins and blood cells out of blood vessels; (3) inflammation often is characterized by a strong infiltration of leukocytes at the site of inflammation, particularly neutrophils (polymorphonuclear cells). These cells promote tissue damage by releasing toxic substances at the vascular wall or in uninjured tissue; and (4) fever, produced by pyrogens released from leukocytes in response to specific stimuli.

Inflammation is caused by various factors such as microbial infection, tissue injury, and cardiac infarction. Classically, inflammation is characterized by five symptoms: redness, swelling, heat, pain, and loss of tissue function. These macroscopic symptoms reflect increased permeability of the vascular endothelium allowing leakage of serum components and extravasation of immune cells. The inflammatory response is then rapidly terminated and damaged tissues are repaired. However, overproduction of cytokines (a cytokine storm) by immune cells to overwhelm pathogens can be fatal. A cytokine storm can also be caused by noninfectious diseases such as graft-versus-host disease (GVHD). Inflammatory responses are also critical for the pathogenesis of autoimmune diseases. (Reviewed in Takeuchi, O. and Akira, S., "Pattern recognition receptors and inflammation," Cell 140(6): 805-820 (2010)).

Germline-encoded pattern recognition receptors (PRRs) are responsible for sensing the presence of microorganisms. They do this by recognizing structures conserved among microbial species, which are called pathogen-associated molecular patterns (PAMPs). Recent evidence indicates that PRRs are also responsible for recognizing endogenous molecules released from damaged cells, termed damage-associated molecular patterns (DAMPs). Currently, four different classes of PRR families have been identified. These families include transmembrane proteins such as the Toll-like receptors (TLRs) and C-type lectin receptors (CLRs), as well as cytoplasmic proteins such as the Retinoic acid-inducible gene (RIG)-I-like receptors (RLRs) and NOD-like receptors (NLRs). These PRRs are expressed not only in macrophages and dentritic cells (DCs) but also in various nonprofessional immune cells. With the exception of some NLRs, the sensing of PAMPs or DAMPs by PRRs upregulates the transcription of genes involved in inflammatory responses. These genes encode proinflammatory cytokines, type I interferons (IFNs), chemokines and antimicrobial proteins, proteins involved in the modulation of PRR signaling, and many uncharacterized proteins. The expression patterns of the inducible genes differ among activated PRRs. (Reviewed in Takeuchi, O. and Akira, S., "Pattern recognition receptors and inflammation," Cell 140(6): 805-820 (2010)).

Mediators of Inflammation

During the inflammatory process, soluble inflammatory mediators of the inflammatory response work together with cellular components in a systemic fashion in the attempt to contain and eliminate the agents causing physical distress. The terms "inflammatory" or "immuno-inflammatory" as used herein with respect to mediators refers to the molecular mediators of the inflammatory process. These soluble, diffusible molecules act both locally at the site of tissue damage and infection and at more distant sites. Some inflammatory mediators are activated by the inflammatory process, while others are synthesized and/or released from cellular sources in response to acute inflammation or by other soluble inflammatory mediators. Examples of inflammatory mediators of the inflammatory response include, but are not limited to, plasma proteases, complement, kinins, clotting and fibrinolytic proteins, lipid mediators, prostaglandins, leukotrienes, platelet-activating factor (PAF), peptides and amines, including, but not limited to, histamine, serotonin, and neuropeptides, and proinflammatory cytokines. The major pro-inflammatory cytokines that are responsible for early responses are IL1-alpha, IL1-beta, IL6, and TNF-alpha. Other pro-inflammatory mediators include Leukemia inhibitory factor (LIF), interferon gamma (IFN-gamma), oncostatin M (OSM), ciliary neurotrophic factor (CNTF), transforming growth factor-beta (TGF-beta), granulocyte macrophage colony stimulating factor (GM-CSF), IL11, IL12, IL17, IL18, IL8, a variety of other chemokines that chemoattract inflammatory cells, and various neuromodulatory factors. The net effect of an inflammatory response is determined by the balance between pro-inflammatory cytokines and anti-inflammatory cytokines (for example IL4, IL10, and IL13, IL16, IFN-alpha, TGF-beta, interleukin 1 receptor antagonist (IL1ra), granulocyte colony stimulating factor (G-CSF), soluble receptors for tumor necrosis factor (TNF) or IL6).

Reactive Oxygen Species in Inflammatory Conditions

Reactive oxygen species ("ROS"), such as free radicals and peroxides, represent a class of molecules that are derived from the metabolism of oxygen and exist inherently in all aerobic organisms. The term "oxygen radicals" as used herein refers to any oxygen species that carries an unpaired electron (except free oxygen). The transfer of electrons to oxygen also may lead to the production of toxic free radical species. The best documented of these is the superoxide radical. Oxygen radicals, such as the hydroxyl radical ($OH^-$)

and the superoxide ion ($O_2^{\cdot-}$) are very powerful oxidizing agents that cause structural damage to proteins, lipids and nucleic acids. The free radical superoxide anion, a product of normal cellular metabolism, is produced mainly in mitochondria because of incomplete reduction of oxygen. The superoxide radical, although unreactive compared with many other radicals, may be converted by biological systems into other more reactive species, such as peroxyl ($ROO^-$), alkoxyl ($RO^-$) and hydroxyl ($OH^-$) radicals.

ROS generation can occur either as a by-product of cellular metabolism (e.g., in mitochondria through autoxidation of respiratory chain components) or it can be created by enzymes with the primary function of ROS generation. (M. Rojkind et al, Cellular & Molec. Life Sci. 59(11): 1872-1891 (2002)). Enzymes capable of rapidly increasing local $H_2O_2$ levels include the family of NADPH oxidases and other oxidases such as xanthine oxidase and 5-lipoxygenase. Since high concentrations of $H_2O_2$ may result in DNA damage and modifications of proteins, lipids and other molecules, excess $H_2O_2$ usually is rapidly catalyzed or reduced by various antioxidant enzymes, such as glutathione peroxidase and catalase.

The prevalent view is that leukocytes undergoing an oxidative burst response are the source of hydrogen peroxide at a site of trauma or infection. Sen, C K and Roy, S., Biochimica et Biophysica Acta, 1780 (11): 1348-1361 (2008). However, it has been shown that wounded epithelium of zebrafish larvae produce a tissue-scale gradient of hydrogen peroxide mediating leukocyte recruitment. Niethammer, C. et al., Nature 459 (7249): 996-999 (2009). Hydrogen peroxide alone and in conjunction with the amplification activity of myeloperoxidase (MPO) is responsible for bacterial killing via the NADPH-oxidase-mediated respiratory burst response of neutrophils. Rada, B., and Leto, T., Contributions to Microbiol. 15: 164-187 (2008); W. M. Nausseef, Histochem. and Cell Biol. 122(4): 277-291 (2004);); W. M. Nausseef, Intl J. Hematol. 74(2): 125-133 (2001).

Hydrogen peroxide is involved in many regulatory cellular events, including the activation of transcription factors, cell proliferation, and apoptosis. For example, hydrogen peroxide produced from the mitochondrial electron transport chain has been shown to play a role in hematopoietic cell differentiation and cell division in flies, can affect cardiac differentiation, vascularization, and angiogenesis, and is capable of modulating a number of principal signaling cascades, including ERK, JNK, p38, MAPK, and P13K/Akt. Hensley, K. et al, Free Radical Biology & Med. 28 (10): 1456-62 (2000); Gabbita, S. P., et al, Arch. Biochem. & Biophys. 376(1): 1-13 (2000).

In addition, hydrogen peroxide can act as an intracellular or local signaling molecule. For example, hydrogen peroxide can modulate protein function by reversible chemical modification of protein thiols, which can result in conformational changes affecting DNA binding, enzymatic activity, multimerization or protein complex formation. For example, hydrogen peroxide induced activation of NFkB, a key regulatory moelcule in the transcription of many genes involved in inflammation, has been reported. Schoonbroodt, S. et al., J. Immunol. 164(8): 4292-4300 (2000); Zin, Z et al, Cancer Res. 60(15): 4053-4057 (2000). Moreover, hydrogen peroxide can activate the release of high mobility group 1 protein from macrophages resulting in amplification of pro-inflammatory stimuli (Tang, D., et al., J. Leukocyte Biol. 81(3): 741-47 (2007)) or modulate leukocyte adhesion molecule expression and leukocyte endothelial adhesion (Sen, C K and Roy, S., Biochem. Biophys. Acta 1780 (11): 1348-61 (2008)).

Hydrogen peroxide has also been proposed as a causation model for inflammatory diseases such as asthma (Loukides, S., Bouros, D., Papatheodorou, G., Panagou, P., Siafakas, N. M., The Relationships Among Hydrogen Peroxide in Expired Breath Condensate, Airway Inflammation, and Asthma Severity, Chestjournal, v. 121, No. 2, 338-346, February 2002), and is believed to accumulate in a wide variety of inflammatory conditions, ischemic incidents, mechanical injuries, and infectious processes For example, in the organism, hydrogen peroxide is a cellular product originating in the mitochondria at Complex II, and a small portion becomes secreted as a caustic extracellular radical. During health and vigor, peroxidases and catalases eliminate accumulated peroxide. Local hydrogen peroxide transfer, in part driven by the gradient of peroxide in inflamed tissue, however, would become restricted by circulatory injury or tissue insult. The restriction would allow peroxide accumulation in the interstitial space. This would occur by capillary compression, and limitation of the avenues for fluid return to the blood. The extracellular matrix is an extension of the interstitial space. In acute inflammation, the extracellular matrix is not yet involved and the interstitial fluid expresses the inflammatory process. In chronic disease, peroxide spreads throughout all of the interstitial space, and the inflammatory condition comes to involve the stroma, bursa, cartilage and bone, causing deformation. The acute inflammatory stage is rapidly and easily treated and at lower doses (usually half) compared with the chronic states.

According to one embodiment, the organometallic complex of the present invention has an anti-inflammatory effect. According to another embodiment, the organometallic complex of the present invention has an antioxidant effect. According to one such embodiment, the complex is capable of denaturation or depolarization or removal of hydrogen peroxide from inflamed sites. According to one embodiment, GML-X3 has an anti-inflammatory effect by spin interaction and depolarization of peroxide in the presence of the global hyaluronic acid matrix. According to one embodiment, GML-X3 forms tube-like structures with hyaluronic acid in the extracellular matrix, that can act as channels for fluid return and charge transfer to the blood stream.

T Lymphocyte Involvement in Inflammation

Cellular immunity, the domain of T lymphocytes, is responsible for many immune reactions and is a major element in many autoimmune reactions. T cells are known to directly kill target cells, to provide "help" for such killers, to activate other immune system cells (e.g., macrophages), to help B cells make an antibody response, to downmodulate the activities of various immune system cells, and to secrete cytokines, chemokines, and other mediators.

The T cell compartment comprises distinct T cell subsets.

The type 1 and type 2 helper classes are defined by their cytokine secretion profiles. T-helper 1 (Th1) cells, which are implicated in the stimulation of inflammation, produce IFN-gamma, GM-CSF, TNF-beta, and TNF alfa. TNF and IFN-gamma signals synergize in inducing an activated state in the macrophage, and lead to increased expression of adhesion and homing molecules in the vascular endothelium, which recruit additional blood-born leukocytes to the site of inflammation. (Paul, Fundamentals of Immunol. p. 397). T helper 2 (Th-2) cells produce IL-4, IL-5, IL-10, and IL-13, and provide help for B cells in their activation and differentiation leading to the humoral immune response. de Waal Malefyt, Immunity 31: 700-702 (2009).

Regulatory T cells, either natural, induced, or Tr1 cells, produce IL-10 and TGFβ, suppress the activation of effector T cells, and provide a counter-balance against uncontrolled and harmful T cell responses. Id. Th9 cells may provide additional help for mast cells through the production of IL-9. Id. Th17, an additional T cell subset, produces IL-17A, 17-17F, IL-22 and CCL20, which act on stromal and epithelial cells to induce a number of secondary effector molecules, such as G-CSF, which stimulates the production and mobilization of neutrophils, acute phase proteins, chemokines, and antimicrobial peptides. Id.

Naive T cells can differentiate into any of the distinct T cell subsets when activated in the presence of appropriate signals and cytokines. The induction of a maturation process in dendritic cells is a crucial step for efficient priming of naive T cells. There is an extensive cross-regulation between subsets to ensure that the appropriate T cell subset is activated. Id.

Wound Healing

Wound healing progresses in distinct and overlapping phases (reviewed in Kanta, J., "The role of hydrogen peroxide and other reactive oxygen species in wound healing," Acta Medica (Hradec Králové) 54(3): 97-101 (2011)). An acute injury initiates a hemostatic phase (meaning the arrest of bleeding) in which blood spills into the site of injury and triggers the formation of a fibrin clot. Hemostasis is followed by an inflammatory phase, in which neutrophils and macrophages remove damaged tissue. During the inflammatory phase, both platelets and macrophages release growth factors and cytokines. This is followed by a proliferative phase, in which endothelial cells form new capillaries, fibroblasts deposit fibronectin, collagen and other components of new extracellular matrix, and keratinocytes restore surface integrity. Finally, during the remodeling phase, fibroblast-rich granulation tissue is replaced with an acellular scar with cross-linked collagen fibrils.

Wound healing depends on a fine balance between the advantageous and deleterious effects of reactive oxygen species (ROS). A characteristic feature of the inflammatory phase is oxidative burst. A majority of ROS is produced by neutrophils and macrophages during the inflammatory phase of wound healing. Wound fluid contains micromolar concentrations of hydrogen peroxide. While low concentrations of ROS may act as second messengers and facilitate wound healing, if the inflammatory phase does not resolve in time and the concentration of ROS exceeds the antioxidant capacity, oxidative stress results. Oxidative stress mediated by radical ROS (e.g., superoxide anion, hydroxyl radical) and nonradical ROS (hydrogen perozide, singlet oxygen) may inhibit cell migration and proliferation and cause tissue damage and perpetuation of inflammation. For example, while incubation of macrophages with low concentrations of $H_2O_2$ (0.1 mM) produces vascular endothelial growth factor (VEGF) that stimulates angiogenesis, high concentrations of $H_2O_2$ (50 mM) applied on excisional dermal wound in mice retard wound closure. Poorly healing wounds are often treated with hyperbaric oxygen therapy (HBOT), in which patients breathe 100% oxygen in a pressurized chamber. HBOT has been reported to improve wound healing and reduce ulcer size in diabetic patients; enhance keratinocyte migration and maturation in human dermis in vitro; and improve healing of ischemic wound in rats. (Kanta, J., "The role of hydrogen peroxide and other reactive oxygen species in wound healing," Acta Medica (Hradec Králové) 54(3): 97-101 (2011).

Previous studies have demonstrated the intrinsic antioxidant ability of several biomaterials in quenching ROS, which may be advantageous in chronic wounds. For example, hyaluron-based wound dressing materials (Moseley R. et al., "Comparison of the antioxidant properties of wound dressing materials—carboxymethylcellulose, hyaluronan benzyl ester and hyaluronan, towards polymorphonuclear leukocyte-derived reactive oxygen species," Biomaterials, 24(9): 1549-1557 (2003)); coenzyme Q10 (CoQ10) grafted on poly(lactic-co-glycolic acid) (PLGA) microspheres (Swarnakar, N. K. et al., "Oral bioavailability, therapeutic efficacy and reactive oxygen species scavenging properties of coenzyme Q10-loaded polymeric nanoparticles," Biomaterials, 32(28): 6860-6874 (2011)); platinum-ferritin nanoparticles (Fan, J. et al., "Direct evidence for catalase and peroxidase activities of ferritin-platinum nanoparticles," Biomaterials, 32(6): 1611-1618 (2011)).

Previous studies have demonstrated the instrinsic antioxidant ability of several biomaterials in quenching ROS, which may be advantageous in chronic wounds. For example, hyaluron-based wound dressing materials (Moseley R. et al., "Comparison of the antioxidant properties of wound dressing materials—carboxymethylcellulose, hyaluronan benzyl ester and hyaluronan, towards polymorphonuclear leukocyte-derived reactive oxygen species," Biomaterials, 24(9): 1549-1557 (2003)); coenzyme Q10 (CoQ10) grafted on poly(lactic-co-glycolic acid) (PLGA) microspheres (Swarnakar, N. K. et al., "Oral bioavailability, therapeutic efficacy and reactive oxygen species scavenging properties of coenzyme Q10-loaded polymeric nanoparticles," Biomaterials, 32(28): 6860-6874 (2011)); platinum-ferritin nanoparticles (Fan, J. et al., "Direct evidence for catalase and peroxidase activities of ferritin-platinum nanoparticles," Biomaterials, 32(6): 1611-1618 (2011)).

According to another embodiment, the organometallic complex is useful in increasing wound healing in treating a wound injury. According to another embodiment, the organometallic complex is useful in reducing inflammation associated with a wound injury. Exemplary injuries include, but are not limited to, physical, chemical, physiological, thermal, etc.

Tendinopathy

The term "tendon" as used herein refers to a nondistensible fibrous cord or band of variable length that is the part of muscle that connects the contracile part of the muscle with its bony attachment or other structure. Tendons are made of fascicles of very densely arranged, almost parallel collagenous fibers, rows of elongated fibrocytes, and minimal ground substance. Tendons connect muscle to bone and allow transmission of forces generated by muscle to bone, resulting in joint movements. Tendon injuries can result in morbidity and disability that can last for months without appropriate management. Tendinopathic lesions affect both collagen matrix and tenocytes. The parallel orientation of collagen fibrils is lost, there is a decrease in collagen fiber diameter and in the overall density of collagen. Normally, collagen fibers in tendons are tightly bundled in a parallel fashion. In tendinopathic samples, there is an unequal and irregular crimping, loosening and increased waviness of collagen fibers with an increase in Type III (reparative collagen). (Reviewed in Longo, U. et al., "Oxygen species and overuse tendinopathy in athletes," Disability and Rehabilitation, 30(20-22): 1563-1571 (2008); Sharma, P. et al., "Tendon injury and tendinopathy: healing and repair," The Journal of Bone & Surgery, 87: 187-202 (2005)).

Tendon healing occurs in three overlapping phases. In the initial, inflammatory phase, erythrocytes and inflammatory cells, especially neutrophils, enter the site of injury. Within 24 hours, monocytes and macrophages predominate and phagocytosis of necrotic material occurs. Vasoactive and chemotactic factors are released with increased vascular permeability, initiation of angiogenesis, stimulation of tenocyte proliferation and recruitment of more inflammatory cells. Tenocytes are tendon cells, which are elongated fibroblasts. Tenocytes gradually migrate to the wound, and type-III collagen synthesis is initiated. The inflammatory phase is followed, within a few days, by the proliferative phase begins, during which collagen III synthesis peaks. After approximately six weeks, the remodeling phase commences with decreased cellularity and decreased collagen and glycosaminoglycan synthesis. (Reviewed in Sharma, P. et al., "Tendon injury and tendinopathy: healing and repair," The Journal of Bone & Surgery, 87: 187-202 (2005)).

The term "tendinopathy" as used herein refers to a disease, disorder or condition of a tendon, e.g., tendinitis, and tendinosis. The terms "tendinitis" or "tendonitis" are used interchangeably to mean inflammation of a tendon. The term "tendinosis" as used herein refers to damage to a tendon at a cellular level exhibiting a pathology of chronic degeneration without inflammation. The term "tendinopathy" provides a generic descriptor of clinical conditions affecting tendons, characterized mainly by swelling, and impaired performance. Therefore, it has been suggested that the terms tendinitis and tendinosis be used only after biopsy and histological confirmation. (Wang, j. H-C. et al., "Biochemical basis for tendinopathy," Clinical Orthopaedics and Related Research, 443: 320-332 (2006)). Histological examination of a tendinosis shows disordered, haphazard healing with an absence of inflammatory cells, a poor healing response, noninflammatory intratendinous collagen degeneration, fiber disorientation and thinning. Hypercellularity, scattered vascular ingrowth, and increased interfibrillar glycosaminoglycans. Tendinosis can be viewed as a failure of the cell matrix to adapt to a variety of stresses as a result of an imbalance between matrix degeneration and synthesis (Sharma, P. et al., "Tendon injury and tendinopathy: healing and repair," The Journal of Bone & Surgery, 87: 187-202 (2005)).

Synthesis, structure and integrity of connective tissues, such as tendons, are influenced by ROS that are produced within the intra- and extra-tendinous environment. Excessive exercise, for example, can induce elevated ROS production primarily from mitochondria. Exercise can also stimulate immune responses with increased leukocyte numbers, in particular granulocytes, generated with bouts of moderate exercise. Increased phagocyte activity may not contribute to elevated ROS levels during short term exercise, but may act as a secondary source of ROS during recovery from heavy exercise. Tendons are cyclically loaded during locomotion as a result of fluctuating stresses. During cyclical tendon loading, a period of maximum tensile load associated with reduced oxygen flow or ischemia alternates with a period of relaxation with reperfusion, i.e., return of the blood flow to the tissue. It has been hypothesized that restoration of normal tissue oxygenation may lead to enhanced free radical production. (Reviewed in Longo, U. et al., "Oxygen species and overuse tendinopathy in athletes," Disability and Rehabilitation, 30(20-22): 1563-1571 (2008)).

Classical ischemia-reperfusion injury involves conversion of hypoxanthine/xanthine dehydrogenase to the superoxide generating oxidase within the ischemic-reperfused tissues. Neutrophil infiltration may also be a source of enhanced ROS production in reperfusion injury. Mitochondria may leak more electrons during reoxygenation. Hyperthermia, a feature of tendon use in exercise, may also lead to increased ROS production, since the central core temperature of muscles during exercise can exceed 47° C. and tendon core temperature may reach 45° C. Furthermore, tenocytes also possess the ability to specifically generate ROS in response to biochemical and physical stimuli that might be encountered on wounding and subsequent healing. Collagen matrix disruption is a critical feature of tendinopathy, which is in general prone to modification by ROS. (Longo, U. et al., "Oxygen species and overuse tendinopathy in athletes," Disability and Rehabilitation, 30(20-22): 1563-1571 (2008)).

Endogenous and exogenous ROS may also exert effects on tenocyte proliferation, development and viability with implications on tendinopathy and post-rupture healing. In wounded tendons, the pro-proliferative action of growth factors and of mechanical load may be mediated through hydrogen peroxide production. Control of ROS levels in the tendon is important in maintaining tenocyte function, as excessive apoptosis or induction of necrosis may cause a loss of tenocyte viability and inefficient matrix synthesis. This may lead both to degeneration and ineffective repair following wounding. (Longo, U. et al., "Oxygen species and overuse tendinopathy in athletes," Disability and Rehabilitation, 30(20-22): 1563-1571 (2008)). Fluoroquinolones, such as pefloxacin, ofloxacin, levofloxacin and ciprofloxacin, constitute a group of potent bactericidal agents, widely used in the treatment of a variety of infectious diseases. Fluoroquinolone use is associated with symtoms of tendinitis and tendon rupture. The increase of intracellular ROS accumulation by fluoroquinolones is believed to be partly responsible for fluoroquinolone-induced tendinopathy. (Reviewed in Kaleagasioglu, F. et al., "Fluoroquinolone-induced tendinopathy: etiology and preventive measures," Tohoku J. Exp. Med., 226: 251-258 (2012)).

According to another embodiment, the organometallic complex is useful in treating tendinopathy. According to one such embodiment, the tendinopathy comprises tendinitis. According to another such embodiment, the tendinopathy comprises tendinosis.

Metal Toxicity

Host response to wear and tear debris from an implantable device is key to clinical performance of the device. Wear debris is generated by mechanical wear, surface corrosion or a combination of both, and can be of two types; particulate and soluble or ionic. Particulate debris (of metals, ceramics or polymers) can range in size from nanometers to millimeters, while metal ion debris exist in soluble forms bound specifically or non-specifically to serum proteins. Corrosion of metal alloys can lead to release of metal ions (e.g., cobalt (Co(II)), titanium (Ti(V)), aluminium (Al(III)), iron (Fe (III)), nickel (Ni(II)), chromium (Cr(III)), etc.). Corrosion products predominantly consist of metal oxides (e.g., $Cr_2O_3$, $CoO$, $TiO_2$, $Al_2O_3$, etc.), and metal hydroxides (e.g., $Cr(OH)_3$, $Co(OH)_2$, etc.) in synovial environments, while deposition of calcium phosphate and subsequent formation of metal phosphates (e.g., $CrPO_4$, $CO_3(PO_4)_2$, etc.). (Reviewed in Hallab, N. J. et al., "Biologic effects of implant debris," Bulletin of the NYU Hospital for Joint Diseases, 67(2): 182-188 (2009); and Keegan, G. M. et al., "Orthopaedic metals and their potential toxicity in the arthroplasty patient," The Journal of Bone and Joint Surgery, 89-B(5): 567-573 (2007)).

Over the past 25 years, growing numbers of case reports have linked immunogenic reactions with the adverse performance of metallic cardiovascular, orthopedic, plastic, surgical and dental implants. Implant debris can lead to inflammation, osteolysis, and hypersensitivity due to metal allergies and neuropathy. For example, both soluble and particulate implant debris from Co—Cr—Mo alloy implants can induce monocyte-macrophage activation and secretion of proinflammatory cytokines (e.g., IL-1β, TNF-α, IL-6 and IL-8), as well as upregulate transcription factor NFκB and its downstream proinflammatory cytokines. All metals corrode in vivo and the released ions can activate the immune system by forming complexes with native proteins. Metal sensitizers including beryllium, nickel, cobalt and chromium elicit hypersensitivity type immune responses. Occasional responses have also been reported with tantalum, titanium, and vanadium. Hypersensitivity reactions include severe dermatitis, uticaria (sensitive and itching red circular wheals on the skin) and vasculitis (patch inflammation of walls of small blood vessels). These symptoms have been linked with metallosis (metallic staining of the surrounding tissue), periprosthetic fibrosis, and muscular necrosis. Generally, there are more case reports of hypersensitivity reactions associated with stainless steel and cobalt alloy implants than with titanium alloy components. The carcinogenic potential of metallic elements released from implantable devices is still speculative. (Hallab, N. J. et al., "Biologic effects of implant debris," Bulletin of the NYU Hospital for Joint Diseases, 67(2): 182-188 (2009)).

There are different mechanisms by which metal nanoparticles can translocate across the plasma membrane. Diffusion (either directly or through membrane channels, about 10-30 nm wide) and receptor-mediated endocytosis are two key mechanisms. Clathrin- or caveolae-mediated endocytosis result in the formation of pits of 120 nm or up to 150 nm, respectively, regulating the size of the nanoparticles that they enclose. Metal nanoparticles less than 200 nm are primarily internalized via receptor-mediated endocytosis. An alternate mechanism of internalization of small particles is via pinocytosis, a non-specific form of endocytosis. Once internalized, metal particles can induce cytotoxicity, chromosomal damage and oxidative stress. (Reviewed in Billi, F. et al., "Nanotoxicology of metal wear particles in joint arthroplasty: a review of current concepts," Journal of Applied Biomaterials & Biomechanics, 8(1): 1-6 (2010); and Keegan, G. M. et al., "Orthopaedic metals and their potential toxicity in the arthroplasty patient," The Journal of Bone and Joint Surgery, 89-B(5): 567-573 (2007)).

The specific mode of uptake of metal ions depend on the particular form of the metal ion. For example, uptake of Cr(VI) ions occur rapidly through anionic channels because of the structure of the chromate anion while Cr(III) accumulates in the plasma membrane. Divalent metal transporter (DMT-1), expressed in a range of tissues, and natural resistance-associated macrophage protein-1 (NRAMP)1, located on the phagosomal membrane, may facilitate the uptake of Co(II) and Ni(II). Transferrin-bound Fe(III), Al(III), Cr(III) or vanadium (V) can be internalized by cell-surface transferin receptors. Metal ions released from implants can induce apoptosis or necrosis in a wide variety of cells, and, within the nucleus can cause mutagenesis by forming adducts with DNA and DNA-DNA cross links. One mechanism that leads to genotoxic effects involves oxidative stress, a redox imbalance within the cell usually due to increased intracellular ROS and decreased antioxidants. The high surface area of metal nanoparticles and the presence of transition metals (such as Co, Cr, Ni, Ti) can promote the generation of ROS, such as the superoxide radical ($O_2$.) and the hydroxyl radical (.OH) via a Fenton-driven reaction with $H_2O_2$. ROS can induce oxidative damage to DNA, proteins, and lipids. Oxidative stress activates specific signal pathways, including NFκB, which, together with depletion of antioxidant defense, lead to the release of proinflammatory cytokines. This cascade of signals trigger inflammation, which leads to further ROS release from inflammatory cells. (Reviewed in Billi, F. et al., "Nanotoxicology of metal wear particles in joint arthroplasty: a review of current concepts," Journal of Applied Biomaterials & Biomechanics, 8(1): 1-6 (2010); and Keegan, G. M. et al., "Orthopaedic metals and their potential toxicity in the arthroplasty patient," The Journal of Bone and Joint Surgery, 89-B(5): 567-573 (2007)).

According to another embodiment, the organometallic complex is useful in treating metal toxicity. The metal toxicity can arise as a result of poisoning from chromium, molybdenum, cobalt, aluminium, nickel, vanadium, zirconium, or titanium. According to another embodiment, the organometallic complex is useful in treating metal toxicity associated with an implantable device. According to another embodiment, the organometallic complex is useful in treating inflammation associated with metal toxicity of an implantable device. Exemplary implantable devices include, but are not limited to, a surgical implant, a pacemaker, a defibrillator, a prosthetic device (e.g. a prosthetic joint, a plate, a rod, a screw, a hip replacement device, a joint arthroplasty implant), a heart valve, a catheter, a stent, a dental device, a metal containing contraception device, etc.

Pathologic Immune Responses

Allergic Disease/Allergic Reaction

Immune responses that are elicited in response to many otherwise innocuous environmental allergens, as well as in response to infections with many parasites, often are associated with high levels of immunoglobulin E ("IgE") production. The amount of immunoglobulins E/High affinity IgE receptor at the surface of basophils can be informative of the allergic status as well as the fact that patients can be on therapy. It generally is believed these immune responses are promoted by antigen-specific T helper 2 (Th2) cells and . that unwanted IgE-associated immune responses (i.e., allergic diseases or allergic reactions) are the unfortunate result of the immune system perceiving and responding to otherwise essentially harmless allergens as if they were derived from a parasite.

In the context of allergic diseases, allergen challenge of a sensitized host can result in a range of tissue responses, depending on such factors as the route and dose of allergen challenge, and on whether the allergen challenge represents a single transient exposure, results in the persistence of the allergen, or occurs seasonally (such as hay fever) or in some other repetitive fashion. Tissue responses also may be impacted by the genetic background of the host and by diverse nongenetic factors (such as certain concurrent infections), which can modify the host's response to allergen.

The effector phases of IgE-associated immune responses may be described as occurring in three temporal patterns: (i) acute reactions (acute response), which develop within seconds or minutes of allergen exposure; (ii) late-phase reactions (late phase response), which develop within hours of allergen exposure, often after at least some of the effects of the acute reaction have partially diminished; and (iii) chronic allergic inflammation (chronic allergic response), which can persist for days to years.

In the early stages of allergy, a hypersensitivity reaction against an allergen, encountered for the first time, causes a response in Th2 cells, a subset of T cells that produce the cytokine interleukin-4 ("IL-4"). The Th2 cells interact with B cells (lymphocytes that produce antibodies against antigens), and, coupled with the effects of IL-4, stimulate the B cells to begin production and secretion of IgE. The secreted IgE circulates in the blood and binds to the high affinity IgE receptor ("Fc∈RI") on the surface of mast cells and basophils, both of which are involved in the acute inflammatory response. At this state, the IgE-coated cells are sensitized to the allergen.

If later exposure to the same allergen occurs, the allergen can bind to the IgE molecules held on the surface of the mast cells or basophils. Cross-linking of the IgE and Fc receptors occurs when more than one IgE-receptor complex interacts with the same allergenic molecule, and activates the sensitized cell. Subsequently, these activated mast cells and basophils undergo the process of degranulation during which they release histamine and other inflammatory chemical mediators, such as cytokines, interleukins and prostaglandins, from their granules into the surrounding tissue causing several systemic effects, such as, for example, but not limited to, vasodilation, mucous secretion, nerve stimulation, and smooth muscle contraction. This may result in rhinorrhea (runny nose), itchiness, dyspnea (difficulty in breathing), or anaphylaxis. Depending on the individual patient, allergen, and mode of introduction, the symptoms may be system-wide (classical anaphylaxis) or localized to particular body systems, such as asthma (localized to the respiratory system) and eczema (localized to the dermis).

After the chemical mediators of the acute response subside, late phase responses may occur. Tissues may become red and swollen due to the migration, initiated by the release of cytokines from mast cells and basophils, of other leukocytes, such as neutrophils, lymphocytes, eosinophils and macrophages, to the initial site. Platelets also may participate. The reaction usually is seen from 2 hours to 24 hours after the original reaction.

Allergic diseases include the group of hypersensitivity disorders that may be (a) associated with the production of specific IgE to environmental allergens and (b) thought to involve, as part of their pathogenesis, IgE-mediated reactions. Allergic reaction can also be IgE independent.

Anaphylaxis

Anaphylaxis is an acute, systemic, hypersensitivity response to an allergen, which typically involves multiple organ systems and which, if untreated, rapidly can lead to death. The vast majority of anaphylactic or anaphylactoid reactions encountered clinically are due to IgE-dependent reactions to penicillin or other antibiotics, foods, or the venom of stinging insects. Further, anaphylaxis also may be IgE independent. It generally is believed that most, if not all, of the signs and symptoms of IgE-associated anaphylaxis in humans reflect (a) the systemic, FcεRI-dependent activation of mast cells and/or basophils and (b) the end-organ consequences of the release of mediators by these cells. Mild cases of acute systemic allergic reactions may primarily involve the skin, which exhibits widespread areas of increased vascular permeability, erythema, and itching (hives). In more severe cases, greatly increased vascular permeability occurs in multiple organ systems, including the upper airways, leading to laryngeal edema and upper airway obstruction. Further, the rapid loss of intravascular fluid volume, together with other consequences of mediator release in anaphylaxis, such as loss of tone in capacitance vessels and decreased contractility of the heart, leads to hypotension and shock. Breathing also may be impaired by marked narrowing of the lower airways, resulting in a severe case of acute asthma, and there may be pronounced gastrointestinal signs and symptoms, such as nausea and vomiting.

Allergic Rhinitis

Allergic rhinitis (hay fever) is one of the most prevalent allergic diseases. It generally is believed that symptoms, which include sneezing, nasal congestion and itching, and rhinorrhea (runny nose), primarily reflect the IgE-dependent release of mediators by effector cells (mainly mast cells and basophils) in response to aeroallergens. Accordingly, symptoms may be seasonal, correlating with the presence of the offending grass, weed or tree pollens, or mold spores, or year-round (for example, the presence of dust mites or animal dander). Typically, symptoms develop rapidly upon exposure to allergen. Nasal tissues usually exhibit marked infiltration with eosinophils and basophils.

ROS plays a prominent role in pathogenesis of allergic diseases. For example, in allergic rhinitis, nasal eosinophils generate hydrogen peroxide, which causes tissue injury and exacerbation of the allergic reaction. (Ogasawara, H. et al., "Hydrogen peroxide generation by eosinophils in allergic rhinitis," Auris, Nasus Larynx, 18(2): 133-143 (1991)). Another source of ROS is environmental pollutants, such as ozone, diesel exhaust, and cigarette smoke that can generate oxidative stress in the airways. Ozone exposure intensifies allergen-induced rhinitis sneezing, nasal secretion, hyperresponsiveness and eosinophil infiltration. (Iijima, M. K. et al., "Exposure to ozone aggravates nasal allergy-like symptoms in guinea pigs," Toxicol. Lett., 123(1): 77-85 (2001); Bacsi, A. et al., "Effect of pollen-mediated oxidative stress to immediate hypersensitivity reactions and late-phase inflammation in allergic conjunctivitis," J. Allergy Clin. Immunol., 116(4): 836-843 (2005)).

Allergic Conjunctivitis

Seasonal alleric conjunctivitis, or hay fever, is one of the most common allergic diseases. The immediate hypersensitivity associated with allergic conjunctivitis is characterized by allergen-mediated cross-linking of IgE on mast cells, leading to degranulation and release of allergic mediators, including histamine, tryptase, leukotrienes, cytokines and platelet activating factors. These mediators stimulate nerve endings, dilate blood vessels, and recruit inflammatory cells to the reaction site, causing clinical symptoms, such as itching, erythema, and palpebral and conjuncival edema. The late phase of the disease is associated with accumulation of inflammatory cells in the conjunctiva. Antigenic components of pollen grains have been implicated in allergic inflammation. Pollen grains contain oxidases that use nicotinamide adenine dinucleotide (reduced) or nicotinamide adenine dinucleotide phosphate (reduced) (NAD[P]H) as an electron donor, which produce ROS and lead to oxidative stress in cultured human epithelial cells and murine conjunctiva. The oxidative stress generated by NAD(P)H oxidase in pollen grains exacerbates the hypersensitivity reactions and pollen antigen-driven allergic conjunctivitis. (Bacsi, A. et al., "Effect of pollen-mediated oxidative stress to immediate hypersensitivity reactions and late-phase inflammation in allergic conjunctivitis," J. Allergy Clin. Immunol., 116(4): 836-843 (2005)).

Asthma

Asthma is an airway disease that can be classified physiologically as a variable and partially reversible obstruction to air flow, and pathologically with overdeveloped mucus glands, airway thickening due to scarring and inflammation, and bronchoconstriction (the narrowing of the airways in the lungs due to the tightening of surrounding smooth muscle). Bronchial inflammation also causes narrowing due to edema and swelling caused by an immune response to allergens. In human allergic asthma, it generally is believed that IgE-dependent mast-cell activation contributes to acute allergen-induced bronchoconstriction, and that mast cells can contribute to the airway inflammation associated with this disorder. In humans, the Fc∈RI can be expressed on several potential effector cells in addition to basophils and mast cells, including monocytes, macrophages, eosinophils, neutrophils and platelets. IgE can directly or indirectly upregulate Fc∈RI expression on basophils and mast cells, and, by binding to this receptor, prime the cells to release increased amounts of key mediators, such as histamine, IL-4, IL-13, macrophage inflammatory protein-1 (MIP-1) and other cytokines Atopic Dermatitis Atopic dermatitis is an inflammatory, chronically relapsing, non-contagious and pruritic skin disease. The skin of a patient with atopic dermatitis reacts abnormally and easily to irritants, food, and environmental allergens and becomes red, flaky and very itchy. It also becomes vulnerable to surface infections caused by bacteria. The skin on the flexural surfaces of the joints (for example, inner sides of elbows and knees) is the most commonly affected region in humans. Naturally occurring lesions of atopic dermatitis may include T cells, along with eosinophils and their products, although their roles are unclear.

Atopic dermatitis often occurs together with other atopic diseases like hay fever, asthma and conjunctivitis. It is a familial and chronic disease and its symptoms can increase or disappear over time. Atopic dermatitis in older children and adults often is confused with psoriasis. Atopic dermatitis afflicts humans, particularly young children; it is also a well-characterized disease in domestic dogs. There is no cure for atopic eczema, and its causes are not well understood.

Skin inflammation in atopic dermatitis is histologically characterized by the infiltration of lymphocytes monocytes, and eosonophils, which release proinflammatory cytokines and reactive oxygen species, such as the superoxide ion ($O_2^{\cdot-}$), hydrogen peroxide, and peroxinitrite ($ONOO^{\cdot-}$). (Leung, D. Y. M., "Atopic dermatitis: new insights and opportunities for therapeutic intervention," J. Allergy Clin. Immunol., 105(5): 860-876 (2000); Wakamatsu, T. H. et al., "Evaluation of lipid oxidative stress status and inflammation in atopic ocular surface disease," Molecular Vision, 16: 2465-2475 (2010)). Increased oxidative stress status, especially elevation of ROS, has been described in patients with atopic dermatitis. (Tsukahara, H. et al., "Oxidative stress and altered antioxidant defenses in children with acute exacerbation of atopic dermatitis," Life Sci., 72(22): 2509-2516 (2003)).

Atopic Keratoconjunctivitis

Atopic keratoconjunctivitis (AKC) is a bilateral, chronic inflammation of the conjunctiva and lids usually associated with atopic dermatitis. The primary symptoms and signs of AKC include itching of the lid skin, perioorbital area, and conjunctiva, tearing, mucous discharge, burning photophobia, and blurred vision. In the field of ophthalmology, oxidative stress has been reported to play a role in several ocular diseases including age-related macular degeneration, cataract, uveitis, retinopathy of prematurity, corneal inflammation, keratitis, etc. AKC patients show higher extent of inflammatory infiltrates in eosinophils, and significant increases in concentrations of proinflammatory cytokines, such as TNF-α, Il-5 and IL-4 in tears, as compared to normal patients. (Lipid peroxidation marker, hexanoyl-lysine (HEL) is significantly increased in tears and conjunctiva of patients with AKC as compared to controls. A close relationship between ROS production, peroxidative lipid membrane damage and an inflammatory pathological processes has been postulated for the ocular surface diseases in AKC. Wakamatsu, T. H. et al., "Evaluation of lipid oxidative stress status and inflammation in atopic ocular surface disease," Molecular Vision, 16: 2465-2475 (2010)).

Angioedema

Angioedema is a self-limited, localized swelling of the skin, which results from extravasation of fluid into interstitial tissues. It affects the skin and mucosal tissues of the face, lips, mouth, and throat, larynx, extremities, and genitalia, often in an asymmetric pattern. Bowel wall involvement presents as a colicky abdominal pain. Angioedema may occur in isolation, accompanied by urticaria, or as a component of anaphylaxis. Mast cell-mediated angioedema is associated with urticaria and/or pruritus in 90 percent of cases. There are many agents, including drugs and allergens, that can result in mast cell-mediated angioedema.

Contact Dermatitis

Contact dermatitis is a condition in which the skin becomes red, sore, or inflamed after direct contact with a substance. There are two kinds of contact dermatitis: irritant or allergic. Irritant dermatitis is caused by contact with acids, alkaline materials such as soaps and detergents, fabric softeners, solvents, and other chemicals. Other irritants may include cement, hair dyes, long term exposure to diapers, pesticides, rubber gloves, etc. Allergic dermatitis is caused by exposure to a substance to which a subject manifests an allergic response. Exemplary allergens include adhesives, antibiotics, fabrics, fragrances, poison ivy, rubber or latex gloves, etc. Treatment for contact dermatitis include, but are not limited to emollients or moisturizers, corticosteroid skin creams or ointments. Oral corticosteroids are administered in severe cases.

Allergic contact dermatitis (ACD) is a severe health problem with increasing worldwide prevalence. It is a T cell-mediated skin disease induced by protein-reactive organic and inorganic chemicals. A key feature of contact allergens is their ability to trigger innate immune response that leads to skin inflammation. Esser et al. have shown that contact allergens induce ROS production that triggers innate inflammatory signaling involving the breakdown of hyaluronic acid of extracellular matrix and generation of endogenous danger signals both in vitro and in vivo. (Esser, P. R. et al., "Contact sensitizers induce skin inflammation via ROS production and hyaluronic acid degradation," PLoS ONE, 7(7): e41340, pp. 1-15 (2012)).

Seborrheic Dermatitis

Seborrheic dermatitis, commonly called dandruff, is a common, inflammatory skin condition that causes itchiness and flaking of skin with or without redness. It affects the scalp, face, trunk, and particularly the sebum-gland rich areas of the skin, usually causing the skin to look inflamed and scaly. The exact cause of seborrheic dermatitis is not known, however, it is thought to be due to a combination of over-production of skin oil and from microbial infections. The treatment depends on body location and age. Dandruff is often treated with a shampoo that contains salicylic acid, the prescription medicine selenium sulfide, zinc pyrithione, ketoconazole or coal tar. Steroid lotions may be used in adolescents and adults.

Rosacea

Rosacea is a chronic inflammatory skin condition associated with redness, swelling and skin sores resembling acne. The condition is characterized by a number of symptoms that include central facial erythema, telangiectasias, papules, granulomatous nodules, phyma formation and ocular changes. Flares and remissions occur without rationale. There are no known cures for rosacea.

Psoriasis

Psoriasis is a chronic inflammatory skin condition associated with redness, and irritation. Psoriasis may affect any or all parts of the skin. Current treatments include topical treatments such as cortisone creams and ointments, creams containing coal tar or anthralin, creams, creams to remove scaling (salicylic acid or lactic acid), dandruff shampoos, moisturizers, or systemic treatments, such as methotrexate, cyclosporine, acitretin, and biologics, such as adalimumab (Humira®), alefacet (Amevive®), etanercept (Enbrel®), infliximab (Remicade®), etc. Psoriasis is a life long condition and is controlled by treatment. There are no known cures for psoriasis.

Acne

Acne or acne vulgaris is one of the most common skin disorders. It is believed to be caused by genetic, hormonal, microbiological and immunological mechanisms. reviewed in Akhavan et al., Am J Clin Dermatol, 2003, 4: 473-492). The pathogenesis of acne is initiated by the follicular occlusion of adherent keratinocytes and hormone-triggered secretion of sebum resulting in the formation of pathophysiological microstructures called microcomedomes. These may enlarge to form visible non-inflammatory acne lesions, often referred to as open or closed comedomes. Conversion of such non-inflammatory acne lesions to an inflamed acne stage occurs principally as a result of the colonization of microcomedomes and comedomes with *Propionibacterium acnes*, an aerotolerant anerobic Gram-positive bacterium, which is largely commensal and constitutes a part of the human skin flora. Acne is commonly treated with topical antibiotics, topical retinoids, salicylic acid, sulfur and azelaic acid.

Autoimmune Disorders

The term "autoimmune disorder" as used herein refers to disease, disorders or conditions in which the body's immune system, which normally fights infections and viruses, is misdirected and attacks the body's own normal, healthy tissue. In higher organisms, multiple mechanisms of immunological tolerance eliminate or inactivate lymphocytes that bear receptors specific for autoantigens. However, some autoreactive lymphcytes can escape from such mechanisms and present themselves within the peripheral lymphocyte pool.

Autoimmunity is caused by a complex interaction of multiple gene products, unlike immunodeficiency diseases, where a single dominant genetic trait is often the main disease determinant. (Reviewed in Fathman, C. G. et al., "An array of possibilities for the study of autoimmunity" Nature, 435(7042): 605-611 (2005); Anaya, J.-M., "Common mechanisms of autoimmune diseases (the autoimmune tautology)," Autoimmunity Reviews, 11(11): 781-784 (2012)).

Autoimmune diseases are major causes of morbidity and mortality throughout the world and are difficult to treat. (Reviewed in for example in Hayter, S. M. et al., "Updated assessment of the prevalence, spectrum and case definition of autoimmune disease," Autoimmunity Reviews, 11(10): 754-765 (2012); and Rioux, J. D. et al., "Paths to understanding the genetic basis of autoimmune disease," Nature, 435(7042): 584-589 (2005)).

One mechanism by which the pathogenic potential of such autoreactive lymphocytes is kept in check is through a dedicated lineage of regulatory T ($T_R$) cells. These have been targeted for therapeutic intervention in a wide variety of autoimmune disorders (Reviewed in Kronenberg, M. et al., "Regulation of immunity by self-reactive T cells," Nature, 435(7042): 598-604 (2005)).

Other components of the pathological cascade in autoimmune disorders that have received attention include, for example, factors involved in lymphocyte homing to target tissues; enzymes that are critical for the penetration of blood vessels and the extracellular matrix by immune cells; cytokines that mediate pathology within the tissues; various cell types that mediate damage at the site of disease, cell antigens; specific adaptive receptors, including the T-cell receptor (TCR) and immunoglobulin; and toxic mediators, such as complement components and nitric oxide. (Reviewed in Feldmann, M. et al., "Design of effective immunotherapy for human autoimmunity," Nature, 435(7042): 612-619 (2005)).

Although mutations in a single gene can cause autoimmunity, most autoimmune diseases are associated with multiple sequence variants. (Reviewed in Rioux, J. D. et al., "Paths to understanding the genetic basis of autoimmune disease," Nature, 435(7042): 584-589 (2005); and Goodnow, C. C. et al., "Cellular and genetic mechanisms of self-tolerance and autoimmunity," Nature, 435(7042): 590-596 (2005)).

Autoimmune disorders can be associated with chronic inflammation. Such autoimmune disorders are known as "autoinflammatory conditions". (Reviewed in Hashkes, P. J. et al., "Autoinflammatory syndromes," Pediatr. Clin. North Am., 59(2): 447-470 (2012)). Exemplary autoimmune disorders or autoinflammatory conditions include, but are not limited to, rheumatoid arthritis, spondyloarthritis, Sjogren syndrome, systemic lupus, multiple sclerosis, cortical encephalitis, etc.

Inflammasomes have been implicated in the pathology of autoinflammatory conditions. An inflammasome is a multiprotein complex that serves as a platform for caspase-1 activation and caspase-1-dependent proteolytic maturation and secretion of interleukin-1β (IL-1β). Despite the wide array of inflammasome activators, the actual triggering is controlled by integration of a comparatively small number of signals that are common to nearly all activators. For example, such triggers can include potassium efflux, elevated levels of reactive oxygen species (ROS), and, for certain activators, lysosomal destabilization. (Reviewed in Gross, O. et al., "The inflammasome: an integrated view," Immunological Reviews, 243(1): 136-151 (2011)); Goldbach-Mansky, R., "Immunology in clinic review series; focus on autoinflammatory diseases: update on monogenic autoinflammatory diseases: the role of interleukin (IL)-1 and an emerging role for cytokines beyond IL-1," Clin. Exp. Immunol. 167(3): 391-404 (2012); Ozkurede, V. U. et al., "Immunology in clinic review series; focus on autoinflammatory diseases: role of inflammasomes in autoinflammatory syndromes," Clin. Exp. Immunol. 167(3): 382-90 (2012); Mankan, A. K. et al., "Immunology in clinic review series; focus on autoinflammatory diseases: inflammasomes: mechanisms of activation," Clin. Exp. Immunol. 167(3): 369-381 (2012)). Recent advances have also been made in the development of biologic drugs in the treatment of autoinflammatory syndromes. (Reviewed in Caorsi, R. et al., "Biologic drugs in autoinflammatory syndromes," Autoimmunity Reviews, Available online Aug. 1, 2012).

Measuring Cellular ROS Production

A number of techniques have been described for measuring cellular ROS based on excitation or spectroscopic shift in a reporter molecule, as quantified by luminometry, flow cytometry or microscopy. Exemplary ROS probes include but are not limited to Pholasin®, luminol (5-amino-2,3-dihydro-1,4-phthalazinedione), 2,7-dichlorodihydrofluorescein (DCFH), lucigenin (10-methyl-9-(10-methylacridin- 10-ium-9-yl)acridin-10-ium dinitrate), cytochrome C, etc. (Reviewed in Bryan, N. et al., "Reactive oxygen species (ROS)—a family of fate deciding molecules pivotal in constructing inflammation and wound healing," European Cells and Materials, 24: 249-265 (2012)). Pholasin® is a ROS excitable photo-protein derived from the marine mollusc *Pholas dactylus*, which emits measurable photons in the presence of most intra- and extracellular derived ROS. Luminol is a synthetic molecule with the ability to oxidize, producing nitrogen and light-emitting aminophthalate. Luminol can also diffuse across cell membranes, thereby allowing detection of both intra- and extracellular ROS, and can be used microscopically to visually track ROS producing cells. DCFH is oxidized in the presence of ROS to 2,7-dichlorofluorescein (DFH), a fluorescent compound which emits light at 520 nm, and can be used for detection of both intra- and extracellular ROS. Lucigenin, another synthetic ROS probe, is not membrane permeable and may be specific to superoxide in extracellular fluids. The spectroscopic shift caused by reduction of iron bound to cytochrome C that can be detected at 550 nm can also be used to quantify production of superoxide. In addition, electron spin resonance uses a family of spin trapping molecules. In ESR, ROS binds to a synthetic molecule causing a measurable shift in the ESR of that molecule. Spin trap molecules include, but are not limited to, nitroso compounds, such as 2-methyl-2-nitrosopropane (MP), 3,5-dibromo-4-nitrosobenzene sulfonic acid (DBNBS) and 5,5-dimethyl-1-pyrroline N-oxide (DMPO).

Combination Therapy

According to some embodiments, one or more of the organometallic complexes of the present invention can be administered in combination with one or more active agents. According to some embodiments, the active agents are administered as part of a single composition. According to some embodiments, the active agents are administered as separate compositions.

For example, one or more of the organometallic complexes of the present invention can be administered in combination with one or more anti-inflammatory agents. Exemplary anti-inflammatory agents include, but are not limited to, non-steroidal anti-inflammatory drugs (NSAIDs) such as acetominaphen (Tylenol), aspirin, celecoxib (Celebrex), diclofenac (Voltaren), diflunisal (Dolobid), etodolac (Lodine), ibuprofen (Motrin), indomethacin (Indocin), ketoprofen (Orudis), ketorolac (Toradol), nabumetone (Relafen), naproxen (Aleve, Naprosyn), oxaprozin (Daypro), piroxicam (Feldene), salsalate (Amigesic), sulindac (Clinoril), tolmetin (Tolectin); and/or steroids such as glucocorticoids, cortisol, testoterone, estrogen, estradiol, progesterone, and/or combinations thereof.

For example, one or more of the organometallic complexes of the present invention can be administered in combination with one or more pain relieving agents, such as, without limitation, non-steroidal anti-inflammatory drugs (NSAIDs) such as acetominaphen (Tylenol), aspirin, celecoxib (Celebrex), diclofenac (Voltaren), diflunisal (Dolobid), etodolac (Lodine), ibuprofen (Motrin), indomethacin (Indocin), ketoprofen (Orudis), ketorolac (Toradol), nabumetone (Relafen), naproxen (Aleve, Naprosyn), oxaprozin (Daypro), piroxicam (Feldene), salsalate (Amigesic), sulindac (Clinoril), tolmetin (Tolectin); steroids such as glucocorticoids, cortisol, testoterone, estrogen, estradiol, progesterone; articaine, benzocaine, bupivacaine, carticaine, chloroprocaine, cinchocaine/dibucaine, cocaine, cyclomethycaine, dimethyocaine/larocaine, etidocaine, levobupivacaine, lidocaine/lignocaine, mepvacaine, piperocaine, prilocalne, propoxycaine, procaine/novocaine, proparacaine, ropivacaine, saxitoxin, tetracaine/amethocaine, trimecaine, and/or combinations thereof.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Making the Organometallic Complex

Initial Scale-up Method

To synthesize GML-X3, a series of four primary feedstock solutions were first prepared: (Step A): Palladium-lipoic acid complex solution (PdLA); (Step B): Arginine-linoleic acid solution (ALI); (Step C): Ruthenium-formyl methionine complex solution (RUF); and (Step D): Zinc chloride solution ($ZnCl_2$).

The next step involved making two secondary feedstock solutions: (Step E): an intermediate complex termed "G10" was prepared by combining PdLA and ALI (Secondary Feedstock Solution #1); and (Step F): a second intermediate complex termed "RUF-ZnCl$_2$" was prepared by separately combining Ruthenium-formyl methionine complex solution (RUF) with ZnCl$_2$ (Secondary Feedstock Solution #2).

Step G: The final product, GML-X3 was prepared by combining RUF-ZnCl$_2$ (Secondary Feedstock Solution #2), with G10 (Secondary Feedstock Solution #1).

Synthesis of GML-X3 Primary Feedstock Solutions

Step A: Method for Making 1 Liter of 0.06 M Palladium Lipoic Acid Primary Feedstock Solution (PdLA)

A 1 liter solution of 0.06 M Palladium Lipoic Acid Primary Feedstock Solution (PdLA) was prepared by the following steps:

Step 1: Palladium dichloride powder (99.9% purity) (FW 177.3 g/mole) was obtained from Alfa Aesar or DeGussa. Analytical grade HCl and NaOH were obtained from Baker. Water was deionized. All metal surfaces involved in the reaction are plastic coated.

A solution of 120.0 mL or 0.12 mole of 1.0 N HCl was placed in a 2 liter round glass reactor in a hemispherical heater. 10.64 g PdCl$_2$ (0.06 mole) was added to the HCl solution. The reactor vessel was continuously stirred with a lightning type motorized stirrer having a plastic coated shaft and rotor so that no metal is exposed to the solution. When a suspension formed, the heat was turned on and the mixture was brought to a gentle boil. Boiling, stirring, and heating were continued for ten minutes. The boiling temperature was close to that of water, eg., 100 degrees C. After ten minutes boiling, a clear dark amber solution was produced. The material was allowed to cool overnight. The material was then filtered free of insolubles using a Buchner funnel with a 3.0 µm pore size fiberglass membrane. The resultant solution was a solution of H$_2$PdCl$_4$.

Step 2: 70.0 mL of 6.0 N or 0.42 mole NaOH solution was placed in a separate similar reactor. 200.0 mL of water was added. 12.38 g or 0.06 mole of DL-α-alpha lipoic acid (Sigma) (FW 206.3 g/mole) was added with constant stirring. The solution was stirred vigorously until it becomes a clear yellow. Any undissolved residue was filtered to clarity resulting in an alkalized yellow lipoic acid solution.

Step 3: The H$_2$PdCl$_4$ solution from Step 1 was added to the round flask containing the alkalized yellow lipoic acid solution from Step 2 and stirred thoroughly. The material was stirred continuously and brought to a gentle boil. Boiling temperature was close to that of water, eg., 100 degrees C. Boiling was continued for fifteen minutes, producing a clear dark reddish brown solution. The material was allowed to cool overnight. Sufficient water was stirred into the cooled solution to achieve a final volume of 1000.0 mL. The resulting solution is a 0.06 M solution of the complex of palladium-lipoic acid (PdLA).

The PdLA solution was mixed well and bottled and labeled as 0.06 M Palladium-Lipoic Acid Primary Feedstock Solution. The composition of the PdLA solution is the following:
Pd$^{2+}$=0.06 M
Lipoic acid=0.06 M
Na$^+$=0.42 M
Cl$^-$=(2×Pd+0.12 from HCl)/1.0=0.24 M Step B: Method for Making 1 Liter of 0.06 M Arginine-Linoleic Acid Primary Feedstock Solution (ALI)

All reactants are reagent grade. In a 2.0 liter beaker with a magnetic stirrer, 11.0 g or 0.063 mole L-arginine base (Sigma) (FW 174.2 g/mole) was dissolved in 800 mL purified H$_2$O with continuous stirring. 16.8 g or 0.06 mole linoleic acid (Alfa Aesar) (FW 280.5 g/mole) was added with vigorous stirring for five minutes until a smooth gel was obtained. 11.25 mL (6 N or 0.0675 mole) NaOH (Baker) was added and stirred until clear. Water was added to make up the volume to 1000 mL and the resulting mixture was stirred until a clear solution was obtained. The resulting solution is a 0.06 M solution of Arginine-Linoleic Acid (ALI).

The ALI solution was mixed well and bottled and labeled as 0.06 M Arginine-Linoleic Primary Feedstock Solution (ALI), and stored at 4° C. The composition of the ALI solution is the following:
Arginine=0.063 M
Linoleic acid=0.06 M
Na$^+$=0.0675 M Step C: Method for Making 1800 mL of 0.014 M Ruthenium-0.132 M N-Formyl Methionine Primary Feedstock Solution (RUF).

42.012 g or 0.2371 mole N-formyl-L-methionine (FW 177.2 g/mole) were added to one liter distilled water placed in a 4 liter beaker with a magnetic stirrer. The solution was continuously stirred until the formyl methionine was clearly dissolved. Next, 372 g or 0.0244 mole RuCl$_3$·XH$_2$O (X<1) (FW 207.43+54.0 g/mole) was added to the formyl methionine solution and continuously stirred until clear. The resultant solution was heated to boiling and boiled for about 5 minutes. The solution was then cooled overnight. Next, the pH of the solution was adjusted to pH 7.8 by adding 50 mL (6N) NaOH and then adjusting the final volume to 1800 mL with distilled water. The resulting solution is a Ruthenium-N-formyl methionine (RUF) solution.

The RUF solution was mixed well and bottled and labeled as 0.014 M Ruthenium-0.132 M N-formyl methionine Primary Feedstock Solution (RUF). The composition of the RUF solution is the following:
RuCl$_3$·3H$_2$O=(6.372/261.43)/1.8=0.01354 M=0.014 M
N-formyl-L-methionine=(42.012/177.2)/1.8=0.13172 M=0.13 M
Na$^+$=(6×0.05)/1.8=0.1667 M
Cl$^-$=3×Ru=3×0.01354=0.0406 M
Ru:N-formyl-L-methionine=1:9.73

Step D: Method for Making Zinc Chloride Solution (ZnCl$_2$)

0.365 M ZnCl$_2$ solution was prepared with the following method to reduce the weighing error associated with the rapid hygroscopic behavior of dry ZnCl$_2$. A new sealed bottle of Reagent Grade ZnCl$_2$ (eg. Sigma 5.0 g) was obtained. The tape seal was removed and the bottle was dusted carefully. The entire closed bottle and its contents were weighed. The bottle was then thoroughly and completely emptied into a beaker. The empty bottle and cap were then weighed and this weight was subtracted from the weight obtained with the full bottle. Sufficient water was added to the ZnCl$_2$ powder (FW 136.30 g/mole) to achieve a concentration of 50 mg/mL (0.365 M). The material was stirred to solution, sealed well and labeled ZnCl$_2$ 0.365 M.

Step E: Method for Making 210 mL of 0.03 M G10 Secondary Feedstock Solution #1): (or 0.03 M Palladium Lipoic Acid-0.03M Arginine-linoleic Acid Feedstock Solution) (Assembly)

A one liter beaker was placed inside a 4 liter beaker and a perforated plastic spacer was placed on the bottom between the two beakers. The beakers were placed on a magnetic stirrer hot plate. This created a water-jacketed double boiler arrangement that prevented foaming and over-boiling during the process. For this example, 105.0 mL of 0.06 M PdLA was poured into the inner 1 liter beaker. Next 105.0 mL of 0.06 M arginine-linoleic acid solution (ALI)

solution was added to this inner beaker. This was followed by pouring water in the outer beaker to reach the level of the two aliquots in the inner beaker. Next, a magnetic stir bar was placed in the inner beaker and the heater and stirrer were turned on. An electronic thermometer probe was placed in contact with the inner beaker liquid surface. A watch glass was placed over the outer beaker. The outer water jacket was brought to a gentle boil. The temperature of the inner liquid was allowed to rise to about 100 degrees C. and this temperature was maintained for six minutes. The heat was turned off. After five minutes, the stirrer was turned off and the resulting solution was allowed to cool. The resulting solution is a 0.03 M G10 Secondary Feedstock Solution #1) (or 0.03 M Palladium Lipoic Acid-0.03M Arginine-linoleic acid).

The resulting intermediate was labelled 0.03 M G10 Secondary Feedstock Solution #1, and contains 210 mL of the following:

$Pd^{2+}$=0.03 M
Lipoic acid=0.03 M
Arginine=0.0315 M
Linoleic acid=0.03 M
$Na^+$=0.2438 M
$Cl^-$=(2×Pd+0.12 from HCl)/1.0=0.12 M Step F: Method for Making 1.8 Liters of Zn—Ru—N-Formyl-L-Methionine Secondary Feedstock Solution #2.

17.12 mL of the 0.365 M $ZnCl_2$ solution was mixed with 1779.46 mL of the 0.014 M Ruthenium-0.13 M N-formyl-L-methionine RUF solution. 3.42 mL 6 N NaOH was added with continuous stirring. The total volume of the resulting solution was 1,800 mL. The resulting solution is a Zn—Ru—N-formyl-L-methionine Secondary Feedstock Solution #2.

The resulting solution was labeled as $ZnCl_2$-Ruthenium-N-formyl methionine Secondary Feedstock Solution #2. The constituents of the resulting solution are:

$ZnCl_2$=0.365×0.01712/1.8=0.003472 M
$RuCl_3.3H_2O$=(0.01354×1.77946)/1.8=0.01339 M
N-formyl-L-methionine=(0.13172×1.77946)/1.8=0.13022 M
$Na^+$=[(0.1667×1.77946)+(6×0.00342)]/1.8=0.1762 M
$Cl^-$=(0.0406×1.77946)+2×0.365×0.01712)/1.8=0.0471 M Step G: Method for Making 2 Liters of GML-X3 or Zn—Ru—N-Formyl-L-Methionine-PdLA-Arginine-Linoleic Acid Formulation 1800. mL of the $ZnCl_2$-Ruthenium-N-formylmethionine Secondary Feed stock solution #2, was mixed with 205.2 mL of 0.03 M G10 Secondary Feedstock Solution #1. The pH was adjusted to 8.0 with a sufficient amount of 6N NaOH. The resulting solution was stirred, and brought to boil for one minute. The process caused darkening of the solution. The solution was allowed to cool to room temperature. The pH was adjusted to 9.0 with a sufficient amount of 6N NaOH. The resulting solution was stirred well and filtered through a filter paper. Any residue remaining was collected for quantification of batch mass. The volume of the filtrate was adjusted to 2,000 mL. The filtrate was then lyophilized to a powder. The lyophilized powder was resolubilized in purified water in concentrations designed for dosage forms. The solution was sterilized by passing through a 0.2µ microfilter. The resultant product is GML-X3. Total concentration after removal of residue is 23.4 mg/mL in the standard solution. The solution was bottled, labeled and stored at 4° C. The composition of GML-X3 is:

1) Ruthenium=0.0120 M
2) N-formyl-L-methionine=0.1171 M
3) Zinc=3.122×10$^{-3}$ M
4) Pd=3.078×10$^{-3}$ M
5) Lipoic acid=3.078×10$^{-3}$ M
6) Arginine=3.232×10$^{-3}$ M
7) Linoleic acid=3.078×10$^{-3}$ M
8) $Na^+$=[(0.1762×1.7982)+(0.2438×0.205a)]/2=0.1834 M
9) $Cl^-$=[(0.0471×1.7982)+(0.12×0.2052)]/2=0.0547 M Example 2

Crystallization of GML-X3

Solid state crystals of GML-X3 were prepared by making a dozen glass streak slides from a stock solution of GML-X3. A 10.0 µL loupe is used to spread the GML-X3 evenly over an entire slide. The slides are allowed to dry for three days and then examined under low power Nikon Labophot-2 Phase Fluorescence microscope at phase magnification of 300×. The crystals appear octahedral in shape. FIG. 1 shows a low power phase microscope picture of a solid-state crystal of GML-X3.

Example 3

Structure Determination

[to be added once data available]

Example 4

Characterization of GML-X3

4.1. High Pressure Liquid Chromatography (HPLC)

Figure 2:
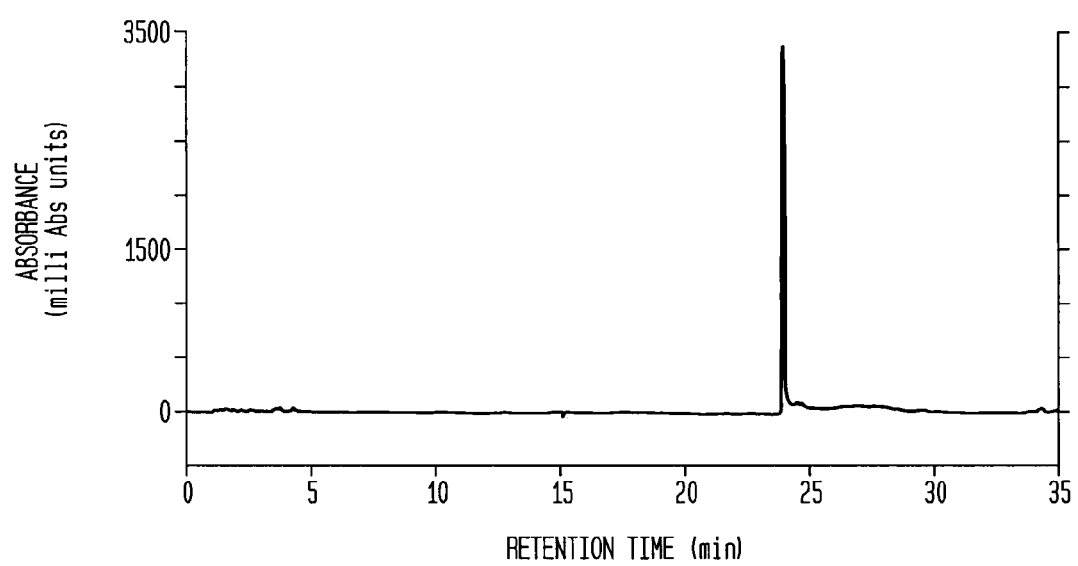
FIG. 2 shows the HPLC elution profile of GML-X3.

GML-X3 has been characterized by High Pressure Liquid Chromatography (HPLC). HPLC was performed on GML-X3 solution with a Beckman System Gold column with isopropanol and ammonium sulfate as the mobile phase. 250 µL GML-X3 stock solution was injected into a Zorbax reverse phase GF450 HPLC column. A 0.05 M ammonium sulfate solution was used as the starting phase, which was subjected to a gradient change against pure isopropanol. Absorbance was detected from 168-264 nm. As shown in FIG. 2, a single sharp peak is demonstrated to elute at 23 minutes showing that GML-X3 is monomolecular. A faint shoulder at the baseline is believed to be an excess of formyl methionine ligand that is used to drive the synthesis and preserve the stability of ruthenium complexation. [

4.2. SDS-PAGE

Figure 3:
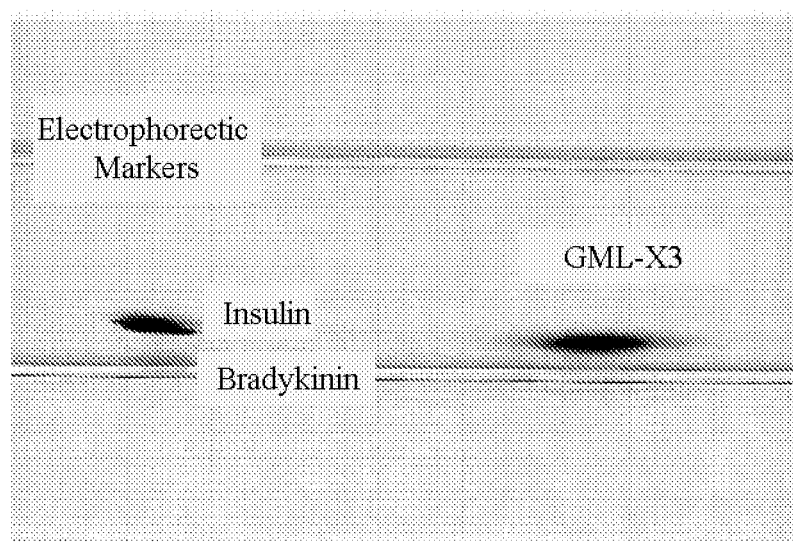
FIG. 3 shows the electrophoretic profile of GML-X3 on NuPage 7.0% Tris-Acetate acrylamide gels. A 20 μl aliquot of GML-X3 stock solution was loaded in lane 2 and electrophoretic marker in lane 1.

GML-X3 was characterized by electrophoresis. Electrophoresis was performed on NuPage 7.0% Tris-Acetate acrylamide gels. Color stained protein markers were migrated in tandem to calibrate the molecular weight of GML-X3. FIG. 3 shows the electrophoretic profile of GML-X3 on NuPage 7.0% Tris-Acetate acrylamide gels. GML-X3 migration is intermediate between insulin (chain B, oxidized bovine marker, 3,496 Da) and bradykinin (1,060 Da). GML-X3 molecular weight is estimated to be about 2520 Daltons.

4.3. UV-Spectroscopy

Figure 4:
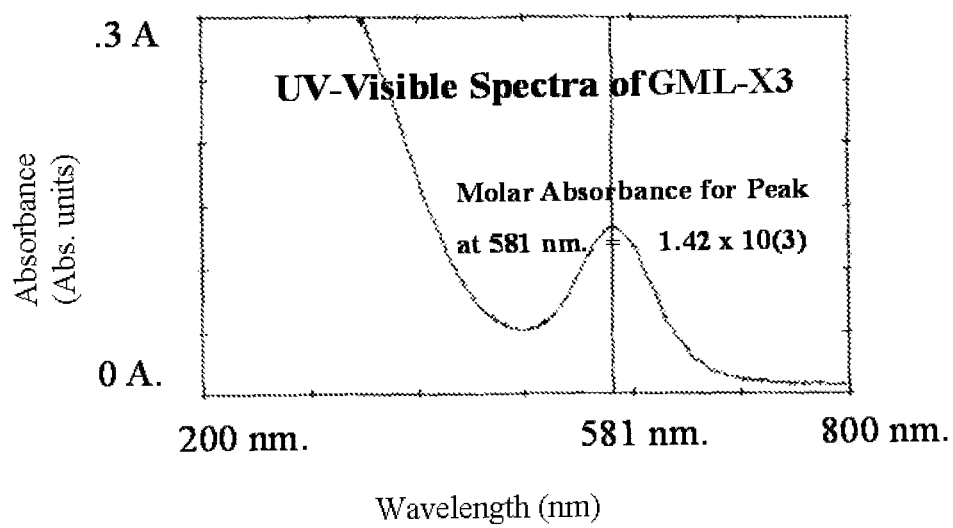
FIG. 4 shows the Ultra-violet-Visible spectrum of GML-X3 scanned with a Shimadzu Model UV 160U Recording Spectrophotometer. The blue solution of GML-X3 shows its characteristic absorbance peak at 581 nm. with a molar absorbance of $1.42 \times 10^3$.

The ultraviolet (UV)-visible spectrum of GML-X3 was recorded with a Shimaduzu UV 160U Spectrophotometer. FIG. 4 shows the UV-Visible spectrum of GML-X3. The blue solution of GML-X3 showed a characteristic absorbance peak at 581 nm. with a molar absorbance of 1.42×10$^3$.

4.5. Fourier Transform Infrared (FTIR) Spectroscopy

In Infrared spectroscopy, infrared (IR) radiation is passed through a sample. Some of the radiation is absorbed by the sample and some of it is transmitted. The resulting spectrum represents the molecular absorption and transmission, creating a molecular fingerprint of the sample. Fourier Transform Infrared (FTIR) spectroscopy overcomes the limitations of dispersive instruments used in IR spectroscopy, allowing the measurement of all of the infrared frequencies simultaneously, rather than individually. Because an analyst requires a frequency spectrum (a plot of the intensity at each individual frequency) in order to make an identification, the measured signal cannot be interpreted directly. A means of decoding is required. This is accomplished by Fourier transformation that is performed by a computing device. The fingerprint peaks from a particular sample originate as a result of molecular vibrations within the sample. There are two types of molecular vibrations: stretching and bending (or scissoring). A molecule consisting of n atoms has a total of 3n degrees of freedom, corresponding to the Cartesian coordinates of each atom in the molecule. In a non-linear molecule, 3 of these degrees are rotational and 3 are translational, and the remaining correspond to fundamental vibrations. The net number of fundamental vibrations in a linear molecule is 3n-5 and in a non-linear molecule is 3n-6. Each vibrational motion can give rise to a distinct peak on the FTIR spectrum if there is a change in the associated dipole. For example, carbon dioxide, $CO_2$, is a linear molecule, and hence has 4 fundamental vibrations: asymmetrical stretching, symmetrical stretching, scissoring (bending in and out of the plane); and scissoring (bending in one side of the plane). The asymmetrical stretch of $CO_2$ gives a strong band in the IR at 2350 $cm^{-1}$.

The formation of GML-X3 and of each intermediate in the process was shown by Fourier Transform Infrared (FTIR) analyses. For the FTIR analyses, desiccated samples were prepared as a KBr mull with a sample weight of 2.0% and assayed with two instruments. Samples were first prepared for Fourier Transform Infrared (FTIR) analysis with a Shimadzu Model 8400S FTIR Spectrophotometer.

Figure 5:
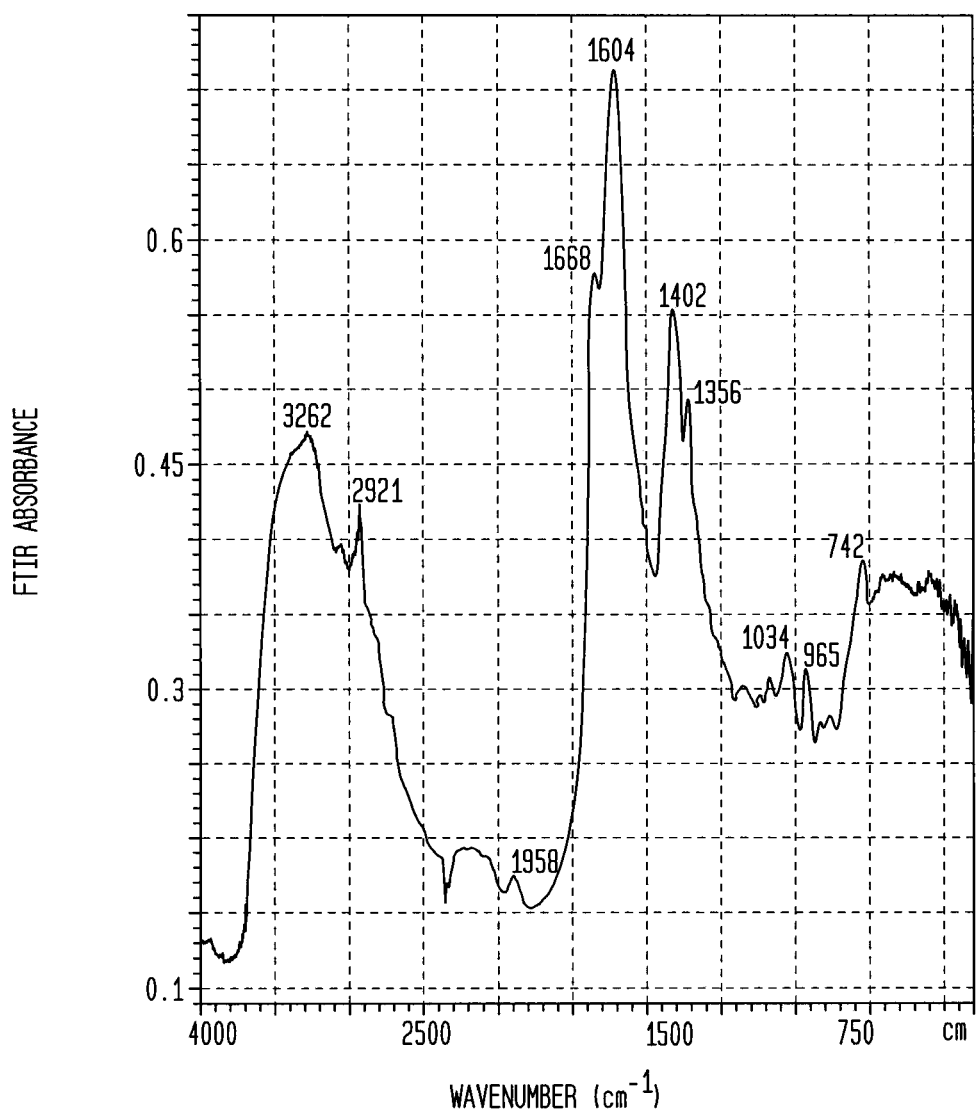
FIG. 5 shows a Fourier Transform Infrared (FTIR) spectrum of GML-X3 using a Shimadzu Model 8400S FTIR Spectrophotometer. Desiccated GML-X3 was prepared in KBr. The FTIR spectrum of GML-X3 shows ten characteristic peaks at: 3262 cm (−1), 2921 cm (−1), 1958 cm (−1), 1668 cm (−1), 1604 cm (−1), 1402 cm (−1), 1356 cm (−1), 1034 cm (−1), 965 cm (−1), and 742 cm (−1).

FIG. 5 shows a Fourier Transform Infrared (FTIR) spectrum of GML-X3 obtained with the Shimadzu Model 8400S FTIR Spectrophotometer. The FTIR spectrum of GML-X3 shows ten characteristic peaks at: 742 cm(-1), 965 cm(-1), 1034 cm(-1), 1356 cm(-1), 1402 cm(-1), 1604 cm(-1), 1668 cm(-1), 1958 cm(-1), 2921 cm(-1), and 3262 cm(-1). The 2921 cm(-1) peak disappears on lyophilization as a result of removal of water of formic acid and the generation of the formate state.

Figure 6:
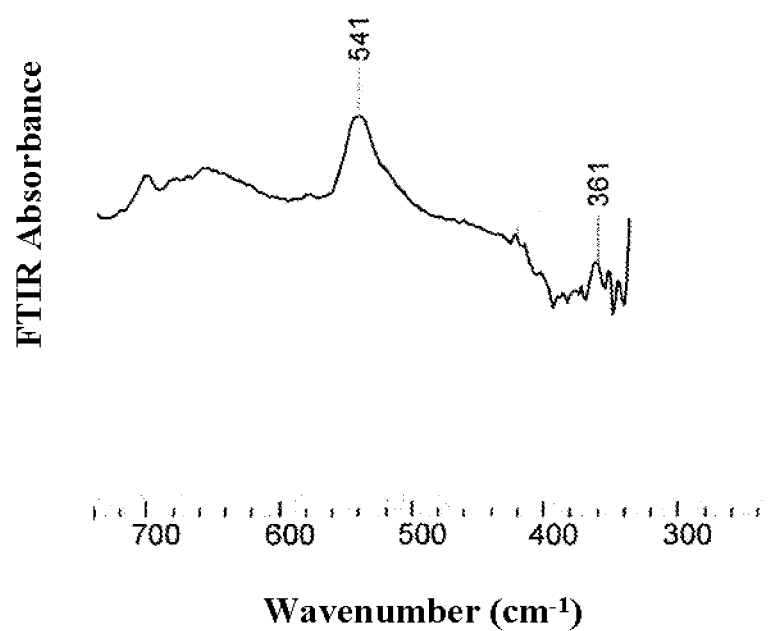
FIG. 6 shows an expanded scale of the a Fourier Transform Infrared (FTIR) spectrum of GML-X3 in KBr with a Cary 630 Spectrophotometer revealing two additional peaks at 361 and 541 wavenumbers.

For a wider band assay, an Agilent Cary 630 FTIR KBr version with the diamond attenuated reflectance attachment was used. FIG. 6 shows an expanded scale of the a Fourier Transform Infrared (FTIR) spectrum of GML-X3 revealing two additional peaks at 361 and 541 wavenumbers.

Figure 7:
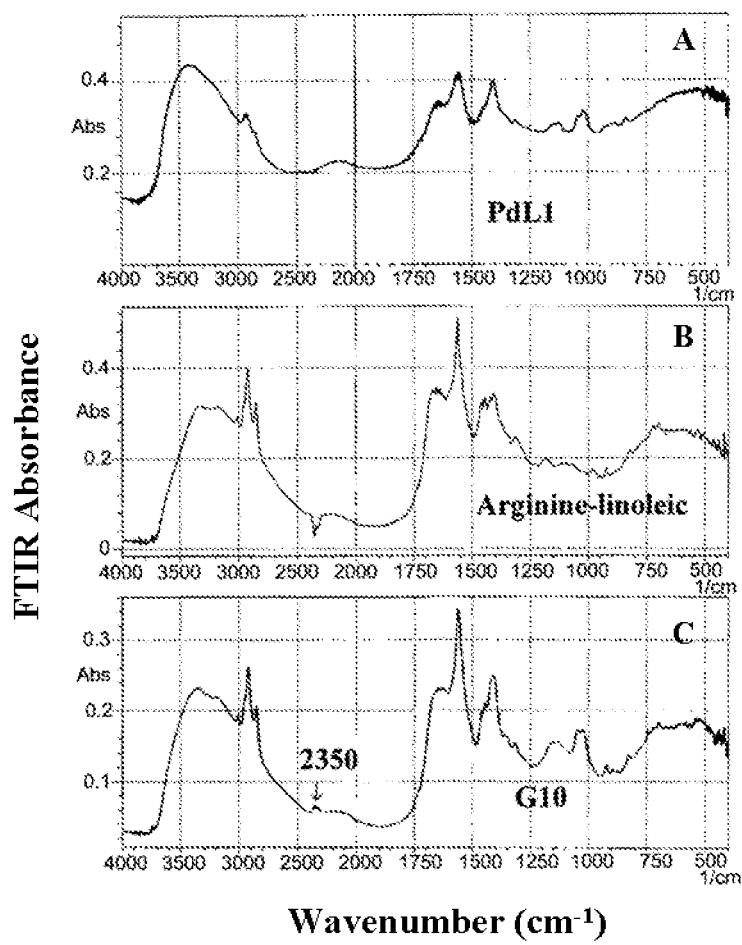
FIG. 7 shows Fourier Transform Infrared (FTIR) spectra, obtained using a Shimadzu Model 8400S FTIR Spectrophotometer, of palladium lipoic acid complex (PLA) (FIG. 7 (a)), arginine-linoleic acid (FIG. 7 (b)), and intermediate G10 obtained upon reacting PLA with arginine linoleic acid (FIG. 7 (c)). Samples were prepared as potassium bromide mulls.

Intermediates formed during the synthesis of GML-X3 were also studied by FTIR spectroscopy with the Shimadzu Model 8400S FTIR Spectrophotometer. In the early stage assembly of GML-X3, palladium-lipoic acid complex was reacted with linoleic acid that was solubilized with arginine and NaOH. FIG. 7 shows Fourier Transform Infrared (FTIR) spectra of palladium lipoic acid complex (PLA) (FIG. 7 (a)), arginine-linoleic acid (FIG. 7 (b)), and the intermediate product G10 (FIG. 7 (c)). When palladium lipoic acid complex (PLA) is reacted with arginine linoleic acid a new FTIR peak appears at 2350 cm (-1) ("2350 peak"), a peak characteristic of the presence of $CO_2$ corresponding to asymmetrical stretching motion of the $CO_2$ molecule. The 2350 peak represents an increased affinity for ambient $CO_2$ in the product (intermediate G10) when compared with the individual reactants. Without being limited by theory, this affinity may correlate with carbonic acid transport kinetics in the GML-X3 complex. In other words, the affinity for $CO_2$ enables use of carbonic acid as a catalytic proton source for the attack on peroxide. Without being limited by theory, the contributing carboxyl of linoleic acid is spin activated by palladium to increase its exchange rate with the gas phase of carbon dioxide.

Figure 8:
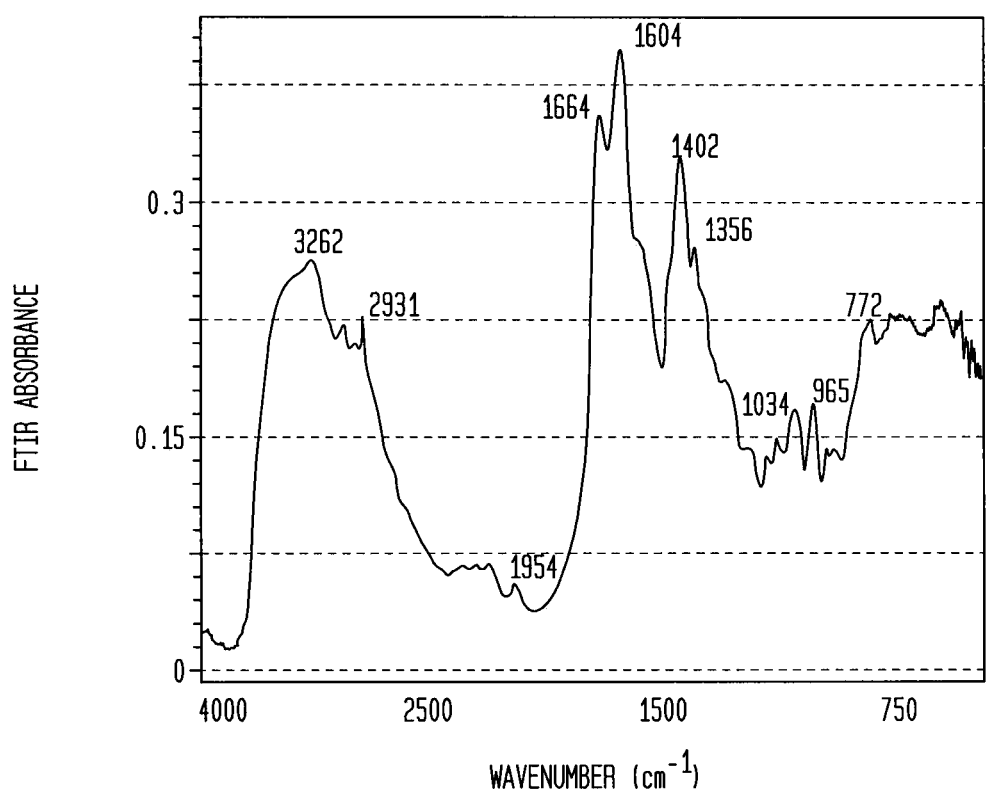
FIG. 8 shows a Fourier Transform Infrared (FTIR) spectrum of a ruthenium complex with formyl methionine, obtained using a Shimadzu Model 8400S FTIR Spectrophotometer. The colorful coordination complex of ruthenium formyl-methionine has distinct FTIR spectrum with ten clearly defined peaks at: 3262 cm (−1), 2931 cm (−1), 1954 cm (−1), 1664 cm (−1), 1604 cm (−1), 1402 cm (−1), 1356 cm (−1), 1034 cm (−1), 965 cm (−1), and 772 cm (−1). Samples were prepared as potassium bromide mulls.

A Fourier Transform Infrared (FTIR) spectrum was also obtained for the ruthenium complex with formyl methionine. FIG. 8 shows a Fourier Transform Infrared (FTIR) spectrum of a ruthenium complex with formyl methionine. The colorful coordination complex of ruthenium formyl-methionine has distinct FTIR spectrum with ten clearly defined peaks at: 772 cm (-1), 965 cm (-1), 1034 cm (-1), 1356 cm (-1), 1402 cm (-1), 1604 cm (-1), 1664 cm (-1), 1954 cm (-1), 2931 cm (-1), and 3262 cm (-1).

Figure 9:
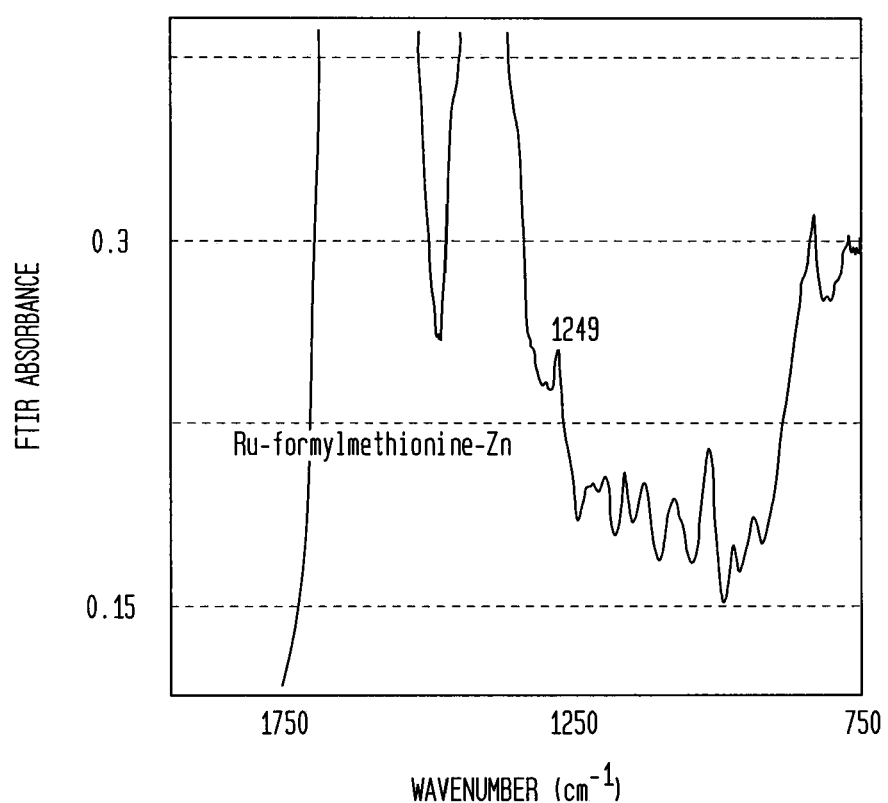
FIG. 9 shows a Fourier Transform Infrared (FTIR) spectrum of a zinc complex of ruthenium formyl methionine, obtained using a Shimadzu Model 8400S FTIR Spectrophotometer. Samples were prepared as potassium bromide mulls. The zinc complex of ruthenium formyl methionine shows the acquisition of a new FTIR peak at 1249 cm (−1).

A Fourier Transform Infrared (FTIR) spectrum was also obtained for zinc complexation with ruthenium formyl methionine. FIG. 9 shows a Fourier Transform Infrared (FTIR) spectrum of a zinc complex of ruthenium formyl methionine. The zinc complex of ruthenium formyl methionine shows the acquisition of a new FTIR peak at 1249 cm (-1).

Finally, the reaction of zinc ruthenium formyl methionine complex with G10 to form GML-X3 results in new peaks characteristic of the association, as shown in FIG. 5.

Figure 10:
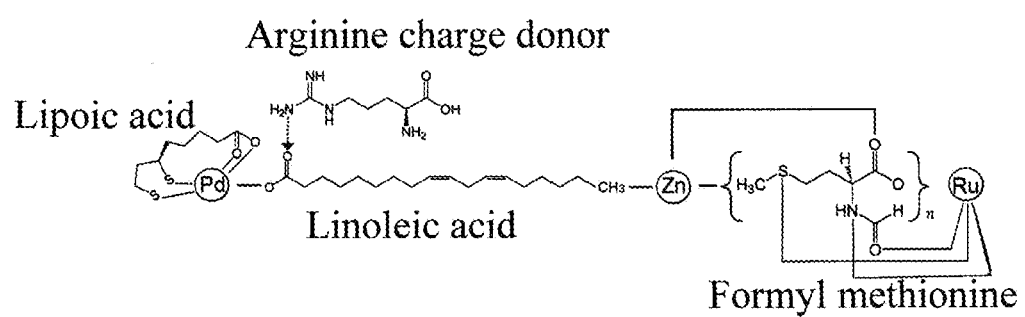
FIG. 10 shows an exemplary structure of an exemplary organometallic complex GML-X3 according to the present invention, consistent with and implied by FTIR and UV visible data from the defined reactants—palladium lipoic acid and ruthenium formyl methionine.

FIG. 10 shows an exemplary structure of an exemplary organometallic complex according to the present invention, GML-X3, consistent with and implied by FTIR and UV visible data from the defined reactants—palladium lipoic acid and ruthenium formyl methionine.

Example 5

In Vitro Interaction of GML-X3 with Hyaluronic Acid (HA)

5.1. Phase Contrast Microscopy

Figure 11:
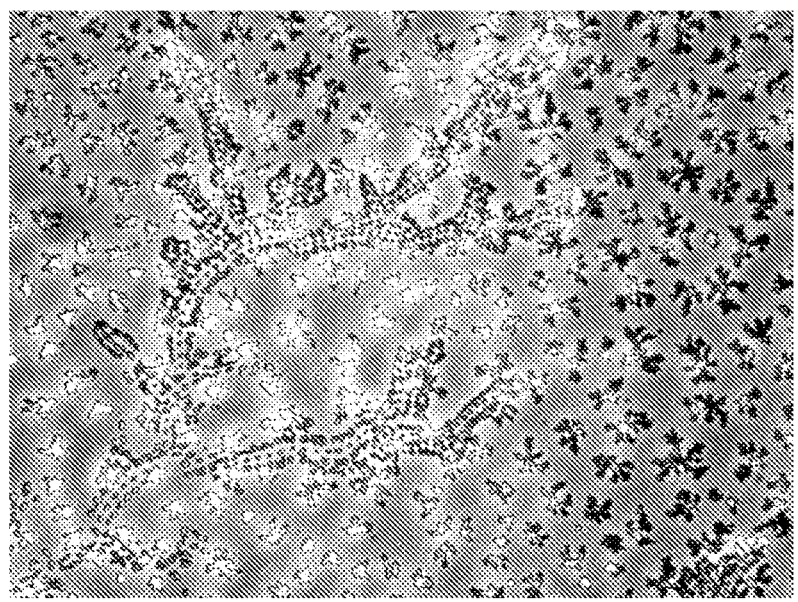
FIG. 11 shows a phase contrast image of a dried sample of a mixture of GML-X3 with sodium hyaluronic acid (HA) at 300× magnification. The diameter of the induced HA tube is about 0.2 µm.

A solution of sodium hyaluronic acid (HA) was prepared (Sigma). Equal volumes of the HA solution and stock GML-X3 solution were mixed. A 10.0 μL loupe was used to spread the mixture on a microscope slide, and the material allowed to dry for five minutes. FIG. 11 shows a phase contrast image of a dried sample of a mixture of GML-X3 with sodium hyaluronic acid (HA). A liquid crystal-like pattern resembling small channels or tubes is observed by low power phase microscopy. Such liquid crystal-like patterns formed with hyaluronic acid, a component of the extracellular matrix, suggests that the tube-like structures constitute a model charge and/or spin transfer structure in vivo. The diameter of the induced HA tube is about 0.2 μm.

5.2. Electron Spin Resonance (ESR) Spectroscopy

In Electron Spin Resonance (ESR) spectroscopy, the interaction between the magnetic moment of an electron with the magnetic moment of a spinning nucleus in its vicinity is known as spin-spin coupling. Spin-spin coupling causes the splitting of ESR lines, a phenomenon known as hyperfine splitting or hyperfine interaction.

Figure 12:
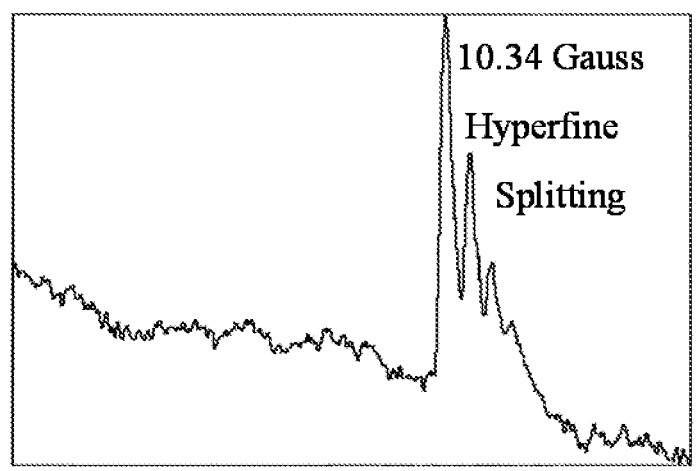
FIG. 12 shows an electron spin resonance ("ESR") scan of GML-X3 with hyaluronic acid ("HA") performed on a Resonance 8400 X-Band continuous wave instrument. The ESR spectrum shows hyperfine splitting to produce a symmetrical quartet with the repetitive splitting interval at 10.34 Gauss, consistent with spin transfer kinetics. The vertical Y axis is the molecular magnetic susceptibility in arbitrary instrument units sometimes referred to as Intensity. The horizontal X axis is the magnetic field in Gauss with a scan range here of 304.96 Gauss.

An electron spin resonance ("ESR") scan of GML-X3 with hyaluronic acid ("HA") was performed on a Resonance 8400 X-Band continuous wave ESR spectrometer. A mixture of GML-X3 with an equal volume of 5.0 mg/mL hyaluronic acid (HA) was prepared. The mixture was injected into Nuclear Magnetic Resonance (NMR) tubes and frozen. The frozen samples were then inserted into the electron spin resonance (ESR) spectrometer. FIG. 12 shows a representative electron spin resonance ("ESR") scan of GML-X3 with HA. The ESR spectrum shows hyperfine splitting to produce a symmetrical quartet with a hyperfine splitting constant at 10.34 Gauss, consistent with a mechanism of spin transfer kinetics. This supports that GML-X3 is capable of spin transfer interaction with hyaluronic acid.

Example 6

In Vitro Interaction of GML-X3 with Hydrogen Peroxide

Single Frequency Mott-Schottky Type Electrochemical Impedance Analysis

The impedance or capacitance can be measured at a single frequency instead of multiple frequencies as in EIS. Single-frequency electrochemical impedance spectroscopy (SF-EIS) monitors a specific characteristic of an electrochemical system occurring at one frequency point. (Crescentini, M. et al., "Recent trends for (bio)chemical impedance sensor electronic interfaces," Electroanalysis, 24(3): 563-572 (2012); Daniels, J. S. et al., "Label-free impedance biosensors: opportunities and challenges," Electroanalysis, 19(12): 1239-1257 (2012)). Graphic techniques, such as Mott-Schottky analyses, can be applied for single-frequency measurements when the frequency selected excludes the contributions of confounding phenomena. For example, impedance measurements at a sufficiently high frequency exclude the influence of leakage currents and electronic transitions. The capacitance can be extracted from the imaginary part of impedance as $$C = \frac{1}{\omega Z_j}.$$

(Orazem, M. E. and Tribollet, B., "Electrochemical impedance spectroscopy," Wiley & Sons, Hoboken, "Mott-Schottky analysis" pp. 225-230 (2008)).

In the Mott-Schottky method, the Y impedance axis can be plotted from the voltage and current data. A software implementing the Mott-Schottky method allows plotting choices including capacitance and inductance as the impedance vector. For spin active molecules (such as GML-X3) that involve magnetic field transfer and minimal electric charge transfer, inductance is the long-range bulk signal. Hence, in such cases, inductance, recorded in Henry units, is plotted as the impedance vector of interest. This inductance resides within impedance data by the retardation of the current pulse with respect to the voltage pulse. SF-EIS was used to study the effect of the mixture of GML-X3 and HA on the electrochemical properties of hydrogen peroxide. A gold working electrode on a Princeton Applied Research Parstat Model 2263 Potentiostat was used with a AgCl reference and Pt counter electrodes. The samples were purged with nitrogen and perturbed at 150 mhz. Peroxide solution was dispersed in NaAcetate. The inductance of hydrogen peroxide is a large electrochemical impedance signal similar to other radicals. This is due to precession pulsation, which advances the angular orbit of unpaired electrons. This movement invokes Faraday's law that a displaced or moving charge forms a magnetic field in its path. The SF-EIS analysis shows that the mixture of GML-X3 and HA is capable of flipping the inductance peak of $H_2O_2$, supporting that GML-X3 is capable of charge transfer, and detoxification and depolarization of $H_2O_2$. The reversal of the polarity of the inductance spike represents a plot of the inductance field discharge and the denaturation of the peroxide in the electric double layer. It is a phase angle reversal and bears no relation to solute flow or hydrodynamics. There is no peroxide flow here, and there are no negative fields. Instead, without being limited by theory, there is a capacitive transient in the electric double layer.

Figure 13:
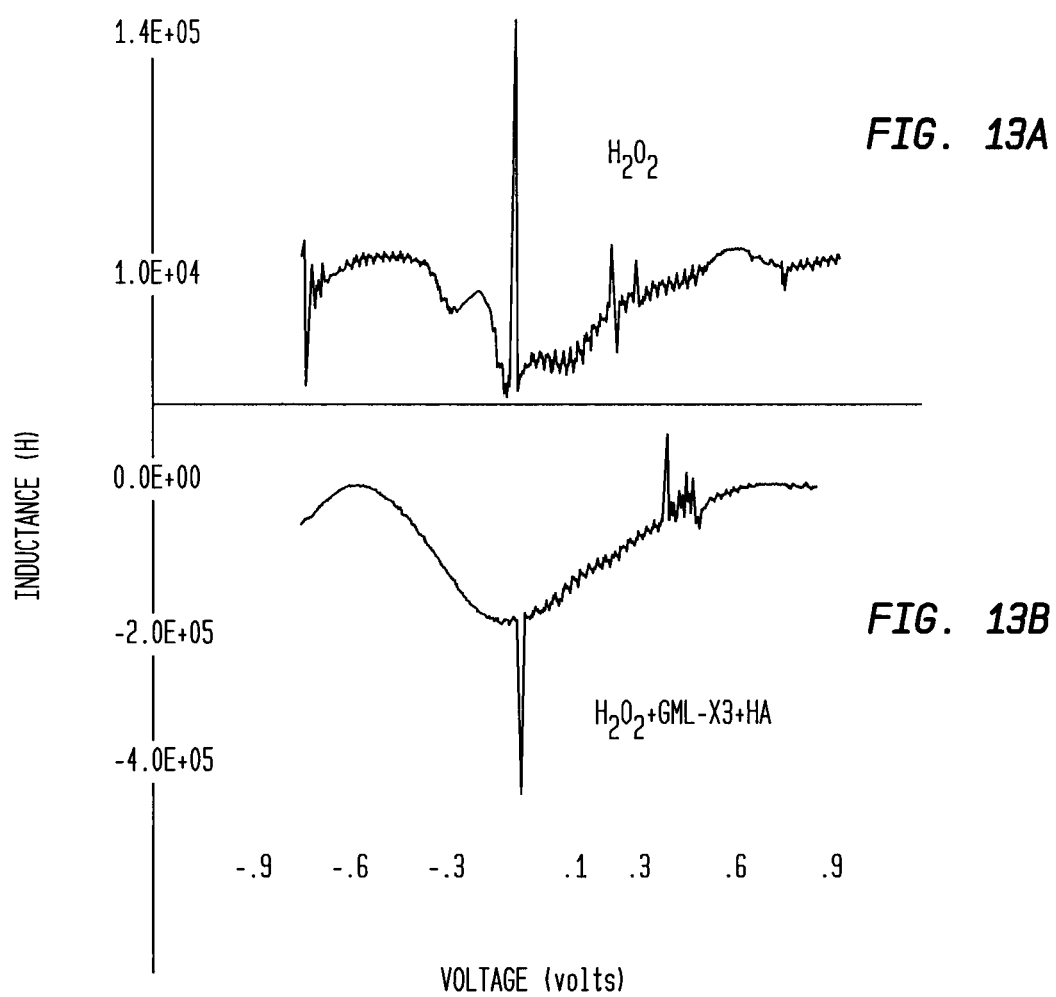
FIG. 13 shows a single frequency Mott-Schottky type electrochemical impedance scan, showing a plot of inductance (Y-axis) over voltage (in volts on X-axis), performed with an EG&G Parstat Model 2263 potentiostat with $H_2O_2$ (FIG. 13 (a)) and with $H_2O_2$ in the presence of a mixture of GML-X3 with hyaluronic acid (FIG. 13 (b)). The peroxide shows a high inductance spike at 150 mHz perturbation, and shows a disproportionately large inductive spike at −16.0 millivolts (FIG. 13 (a)). If GML-X3 and hyaluronic acid are added to the peroxide, the peroxide scan reverses its polarity downwards (FIG. 13 (b)).
Figure 14:
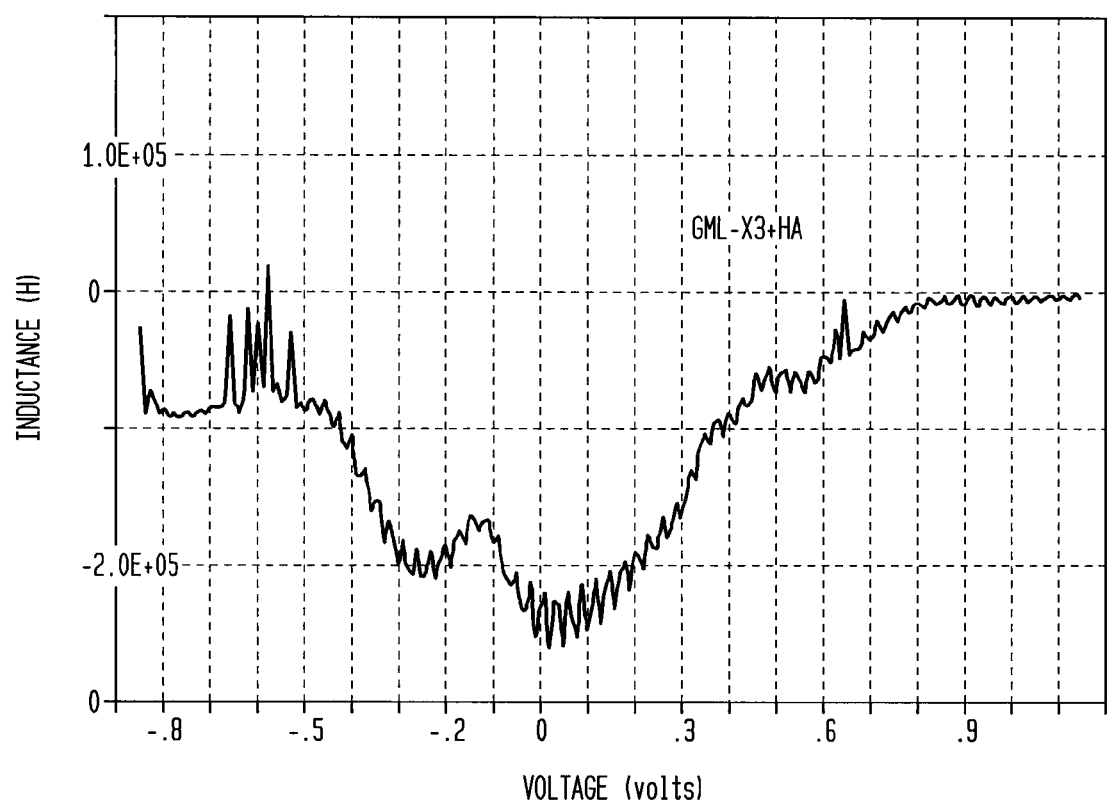
FIG. 14 shows a single frequency Mott-Schottky type electrochemical impedance scan, showing a plot of inductance (Y-axis) over voltage (in volts on X-axis), using a mixture of GML-X3 and hyaluronic Acid (HA). The mixture of GML-X3 and Hyaluronic Acid shows no inductance spike.

Using a potentiostat, electrochemical impedance spectroscopy (EIS) is performed with a gold working electrode, a platinum counter electrode, and a Ag/KCl reference electrode. A 0.1 M sodium acetate background electrolyte is used and the solution is purged with nitrogen for 12 minutes. FIG. 13 shows a single frequency Mott-Schottky type electrochemical impedance scan, showing a plot of inductance (Y-axis) over voltage (in volts on X-axis), performed with an EG&G Parstat Model 2263 potentiostat with $H_2O_2$ (FIG. 13 (a)) and with $H_2O_2$ in the presence of a mixture of GML-X3 with hyaluronic acid (FIG. 13 (b)). The peroxide shows a high inductance spike at 150 mHz perturbation, and shows a disproportionately large inductive spike at −16.0 millivolts (FIG. 13 (a)). In addition, single frequency impedance (Mott-Schottky method) of hydrogen peroxide at 150 mHz perturbation shows a disproportionately large inductive spike at −16.0 millivolts. If GML-X3 and hyaluronic acid are added to the peroxide, the peroxide scan reverses its polarity downwards (FIG. 13 (b)). FIG. 14 shows a single frequency Mott-Schottky type electrochemical impedance scan, showing a plot of inductance (Y-axis) over voltage (in volts on X-axis), using a mixture of GML-X3 and hyaluronic Acid (HA). The mixture of GML-X3 and Hyaluronic Acid shows no inductance spike but shows inductance oscillation in the electronegative range. FIG. 13 illustrates peroxide depolarization by GML-X3 and hyaluronic acid, showing a dramatic inversion of the peroxide peak. FIG. 14 is a control slide showing that GML-X3 and hyaluronic acid do not exhibit the peroxide type inductance peak.

The reversal of the hydrogen peroxide inductance polarity is consistent with its denaturation, and is interpreted as a discharge of the micro-magnetic field. It is thought that in peroxide depolarization, GML-X3 with hyaluronic acid forms an intermediate liquid crystal-like complex assembling into tube-like structures. (FIG. 11). The negative inductance peak is analogous to negative differential resistance (NDR) which is occasionally observed in impedance measurements of discharging capacitance. The peroxide reaction can be termed a "negative differential inductance (NDI)", that emphasizes the discharge of the inductance field, and a basis for spin transfer.

Example 7

In Vitro Interaction of GML-X3 with Glycine 7.1. Phase Contrast Microscopy

Figure 15:
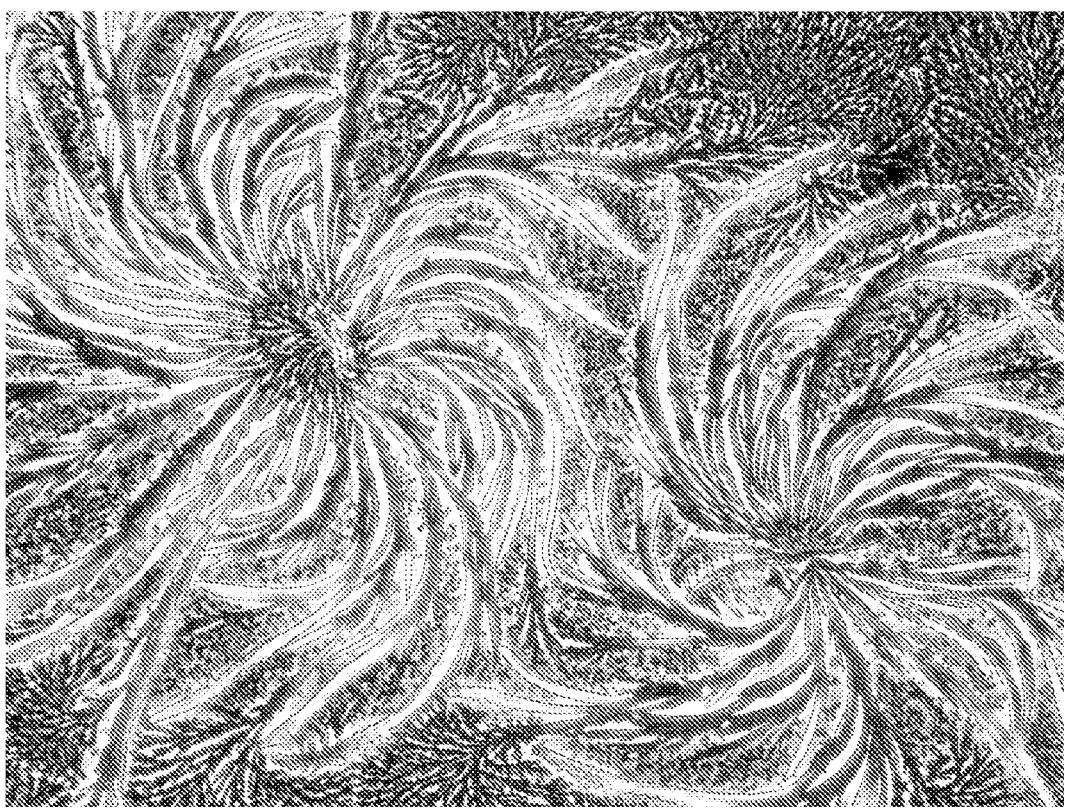
FIG. 15 shows a 300× phase contrast microscope image of a dried sample of GML-X3 in glycine. The phase contrast image shows structures resembling swirling vortices that may represent induction of a high energy spatial transition suitable for energy transfer.

A pair of unique and correlated signatures further allowed the identification of GML-X3. The method involved admixing 5 µl of GML-X3 solution with an equal volume of 0.05 M glycine. The 10 µl sample mixture was spread on a glass slide with a loupe and allowed to dry. The slide was visualized under a 300× phase microscope. FIG. 15 shows a 300× phase contrast microscope image of a dried sample of GML-X3 in glycine. At this magnification a variety of sizes of structures resembling swirling geometrically detailed and distinct vortices can be seen depending on the stage of development. Control slides of individual reactants show no such patterns of swirling vortices. Without being limited by theory, such swirling vortex-like patterns may represent induction of a high energy spatial transition suitable for energy transfer. Without being limited by theory, the interaction between GML-X3 and glycine may be an example of three dimensional vortex pinning, as described in Blatter, G., et al., "Aspects of vortex pinning, Swiss Federal Institute of Technology—web posting, ETH Zurich, 2009; and Chen, Z. et al., "Three-dimensional vortex pinning by nano-precipitates in a Sm-doped YBa2Cu3O7-x coated conductor," Supercond. Sci. Technol. v. 20, S205-S210, 2007. Localization and maturation of a vortex with a surface or a matrix is called pinning and is a dynamic phase change. When an inductive or magnetic vortex is pinned, it is localized and discharges its field to the receptor or discharges as part of a chemical reaction. Glycine is one example of a chemical matrix suitable for pinning certain vortices. Pinning involves exchange of vortex energy with the matrix or surface. Whether a vortex is a hurricane or a whirlpool or a black hole in space, there is a unique funnel geometry supremely designed for energy focus. Pinning is a phase state but has unique geometry. The vortex literature is large and shows great varieties of examples. Vortices are widely seen under the microscope. Vortices shown in FIG. 15 are pinned by the use of glycine.

7.2. Fourier Transform Infrared (FTIR) Spectroscopy

The mixture of GML-X3 and glycine was subjected to FTIR analysis. FIG. 16 shows a Fourier Transform Infrared (FTIR) spectrum of a mixture of GML-X3 in glycine with a Shimadzu Model 8400S FTIR Spectrophotometer, revealing induction of a new peak at 3410 cm(−1), which is not present in the FTIR spectra of either GML-X3 alone (FIG. 6) or glycine alone (data not shown). This peak is referred to as the vortex associated conformation peak. Vortex structures can be visualized with phase microscopy with GML-X3 and glycine (FIG. 15), but not with GML-X3 alone (data not shown). Formation of the vortex is a phase change.with an FTIR vibrational interaction showing at 3410 cm-1, as a kinetic transient interaction. The remaining FTIR peaks of the GML-X3-glycine mixture are: 742 cm(−1), 905 cm(−1), 1034 cm(−1), 1356 cm(−1), 1406 cm(−1), 1600 cm(−1), 2101 cm(−1), 2285 cm(−1), 2922 cm(−1), and 3253 cm(−1).

Example 8

Bioavailability

The bioavailability of GML-X3 was studied in mice. GML-X3 was administered orally to 6 female Swiss mice at 1.84 mg/Kg/day for 30 days, and 2 mice acted as controls drinking only water. The blood was removed and the serum isolated for assay. Instrument controls on raw GML-X3 were also established at 1:1, 100:1, and 1000:1 dilution. The organs of mice that had received GML-X3 were removed. Inductively Coupled Plasma Mass Spectrometry (ICP-MS) was performed to assess the presence of the GML-X3 metals in the tissues. The serum of mice on prolonged oral dosage of GML-X3 were analyzed with Inductively Coupled Plasma Mass Spectrometry (ICP-MS).

ICP-MS is an analytical technique that performs elemental analysis with high sensitivity. The ICP-MS instrument employs an argon plasma (ICP) as an ionization source and a mass spectrometer (MS), usually with a quadruple mass filter to separate the ions produced. It can simultaneously measure most elements in the periodic table and determine analyte concentrations down to subnanogram per liter or parts per trillion (ppt) levels. In an ICP-MS instrument, liquid samples are introduced by a peristaltic pump to a nebulizer where a sample aerosol is formed. A double-pass spray chamber ensures that aconsistent aerosol is introduced to the plasma. Argon gas is introduced through a series of concentric quartz tubes, known as the ICP torch. The torch is located in the center of a radio frequency (RF) coil. A Tesla coil ionizes the argon gas and free electrons are accelerated by a 27 MHz radio frequency field. Collisions between the accelerated electrons and the argon gas generate a high-temperature plasma. The sample aerosol is instantaneously decomposed in the plasma to form analyte atoms, some of which are ionized. The ions produced are extracted from the plasma into the mass spectrometer region, which is maintained at a high vacuum (typically 10-6 torr) using differential pumping. The analyte ions are extracted through a pair of orifices, approximately 1 mm in diameter, known as the sampling cone and the skimmer cone. The analyte ions are then focused by a series of lenses into a quadrupole mass analyzer which separates the ions based on their mass-to-charge ratio (m/z). Finally, ions are detected using an electron multiplier, and data at all masses are collected and stored through a computer interface. Each elemental isotope appears at a different mass on a mass spectrum obtained with the ICP-MS instrument.

Table 1 shows serum levels of GML-X3 in GML-X3-treated and control mice.

TABLE 1

| Bioavailablity data of GML-X3 | | | |
|---|---|---|---|
| | Zinc | Ruthenium | Palladium |
| GML-X3 Treatment | 1.06 | 117142.2 | 30061.7 |
| Control | 0.88 | 23845.5 | 6979.5 |

The levels of palladium and ruthenium increased in the treated mice as compared with controls. The zinc levels appear in a natural physiologic background level and are therefore less clear. Therefore GML-X3 appears to achieve bioavailability as evidenced by the bioavailability of palladium and ruthenium.

Example 9

Effect of GML-X3 in Inflammatory Models of Contact Dermatitis

Esser et al. have shown that contact allergens induce ROS production that triggers innate inflammatory signaling involving the breakdown of hyaluronic acid of extracellular matrix and generation of endogenous danger signals both in vitro and in vivo. (Esser, P. R. et al., "Contact sensitizers induce skin inflammation via ROS production and hyaluronic acid degradation," PLoS ONE, 7(7): e41340, pp. 1-15 (2012), which is incorporated by reference in its entirety). Anti-inflammatory, and detoxifying effects of GML-X3 can be shown by rescuing toxic effects of contact sensitizers in vitro with inflammatory cell lines (e.g. murine keratinocyte cell line, such as Pam212 and fibroblast cell line such as L929), and in vivo by the treatment of mouse ears with the contact sensitizers. Exemplary contact sensitizers that can be used to trigger ROS production and inflammation include, but are not limited to 2,4,6-trinitrobenzene sulfonic acid (TNBS), 2,4,6-trinitrochlorobenzene (TNCB), or lipopolysaccharide (LPS), 4-ethoxylmethylene-2-phenyloxazol-5-one (oxalone), etc.

To study the effect of GML-X3 in rescuing toxic effects of contact sensitizers in vitro, intracellular oxidant production in inflammatory cells, e.g., murine keratinocyte cells (Pam212) and fibroblast cells (L929), is determined based on the oxidation of chloromethyl-2',7'-dichlorodihydrofluorescein diacetate (CM-H$_2$DCFDA) by intracellular ROS resulting in the formation of a detectable fluorescent product, 2',7'-dichlorodihydrofluorescein (DCF), as described in Esser et al., PLoS ONE, 7(7): e41340, pp. 1-15 (2012). The cells are divided into two batches: test and control. The test batch cells are preincubated for one hour with GML-X3 (25 mg/ml in a suitable carrier, such as phosphate buffered saline), while the control batch is preincubated with the carrier alone at room temperature. The ROS indicator dye, CM-H$_2$DCFDA (5 µm) is added to the cells and incubated for 30 minutes at room temperature. ROS production is induced using contact sensitizers, 2,4,6-trinitrobenzene sulfonic acid (TNBS), 2,4,6-trinitrochlorobenzene (TNCB), or lipopolysaccharide (LPS), and 4-ethoxylmethylene-2-phenyloxazol-5-one (oxalone). ROS production is determined by measuring DCF fluorescence at OD 485/528 every 10 minutes for 1 hour using an ELISA reader. The results from the control and GML-X3 treated cells are then analyzed using suitable software and compared to determine the detoxifying effect of GML-X3 on ROS production.

The effect of GML-X3 in rescuing toxic effects of contact sensitizers ex vivo is tested according to the method described in Esser et al., PLoS ONE, 7(7): e41340, pp. 1-15 (2012). Mice (6-10 weeks age) are divided into two groups: a control untreated group and a treated group. Ears of mice are wiped excessively with ethanol and then topically treated with either phosphate buffered saline (PBS) (control) or GML-X3 (treated) for 15 minutes, and subsequently with a contact sensitizer 2,4,6-trinitrochlorobenzene (TNCB) for 15 minutes. The ears are taken after euthanasia and incubated ex vivo for 30 minutes with dihydroethidium (DHE) (5 mM) in DMSO. 8 mm punches are applied to glass slides and ROS production is monitored using fluorescence microscopy as oxidation of DHE results in the generation of fluorescent 2-hydroxyethidium.

To study the anti-inflammatory effect of GML-X3 on contact hypersensitivity in vivo, mice are pretreated with either PBS alone (control) or oral GML-X3 (treated) daily for 7 days. Mice are first sensitized with 100 µl contact sensitizer or respective solvent on shaved abdomens of 3-5 mice/group. Ear thickness is measured on day 5 and mice are challenged by the application of 20 µl contact sensitizer (1% oxazolone or 1% TCNB) or respective solvent control to the ears. Ear thickness is measured 24 hours later.

Example 10

Effect of GML-X3 on Atherosclerotic Plaques and Oxidative Stress

Vascular inflammatory responses are linked with oxidative stress that stimulate the development of pre-atherosclerotic lesions. Oxidized low density lipoprotein and macrophage foam infiltrates are pro-inflammatory substrates that contribute to proinflammatory states involved in the initiation of atherosclerotic plaques. Yu et al. described the application of electrochemical impedance spectroscopy in assessing electrochemical changes in preatherosclerotic lesions in explants of human and rabbit aortas. Concentric bipolar microelectrodes were applied to the explants and frequency dependent EIS measurements were taken between 10 kHz and 100 KHz. Yu et al. showed that the EIS measurements and vascular resistance were significantly elevated where explants were associated with atherosclerotic and preatherosclerotic lesions. (Yu, F. t al., "Electrochemical impedance spectroscopy to characterize inflammatory atherosclerotic plaques," Biosensors and Bioelectronics, 30(1): 165-173 (2011); Yu, F. et al., "Electrochemical impedance spectroscopy to asses vascular oxidative stress," Ann. Biomed. Engg., 39(1): 287-296 (2011), each of which is incorporated by reference in its entirety).

The effect of GML-X3 on electrochemical properties of preatherosclerotic lesions are studied using the methods described in Yu et al. 10 week old rabbits are divided into three groups: a normal group, a control group with atherosclerotic lesions treated with PBS and a test group with atherosclerotic lesions treated with GML-X3. The rabbits from the control and test groups are fed with a high fat, high cholesterol diet for 8 weeks. The normal group rabbits are fed a fat-free diet for 8 weeks. The test group rabbits are given GML-X3 daily for the final week. The control group rabbits are given PBS. The rabbits are then euthanized, the hearts and aorta resected for ex vivo study. The rabbit aorta is flushed with physiological saline solution and resected longitudinally to expose the inner lumen. Tissue specimens at approximately 2 cm in length are isolated from the aortic arch, thoracic aorta, and abdominal aorta, respectively. Endoluminal EIS measurements are performed at multiple sites associated with the plaque lesions, compared to the healthy arterial lumens. The concentric bipolar working microelectrodes are used; with an inner platinum pole, and the stainless steel outer shell. An Ag/AgCl electrode immersed in the PBS solution is used as a reference electrode. EIS measurements were performed by using a potentiostat. An input of 10 mV peak-to-peak AC voltage and a frequency decay ranging from 300 kHz to 100 Hz are delivered to the sites. The magnitudes and phases of the impedance are acquired at at least 20 data points per frequency decade. The impedance measurements obtained from the normal, control and test groups are compared to determine the effect of GML-X3 on atherosclerotic lesions.

Example 11

Effect of GML-X3 on Allergic Asthma

Human allergic asthma is a chronic inflammatory disorder of the airways, characterized by airway inflammation, persistent airways hyeprresponsiveness (AHR), intermittent, reversible airways obstruction, and airway remodeling symptoms that include structural changes in the airway, such as subepithelial and airway wall fibrosis, goblet cell hyperplasia/metaplasia, smooth muscle thickening and increased vascularity. Chronic allergen exposure in mice is the model of choice for studying the role of specific cell types and inflammatory cytokines and mediators involved in inflammation, including structural changes to the airways (Nials, A. T. et al., "Mouse models of allergic asthma: acute and chronic allergen challenge," Dis. Model Mech., 1(4-5): 213-220 (2008)). The anti-inflammatory effect of GML-X3 is studied in a mouse model for allergic asthma, as described in McMillan, S. J. et al., "Therapeutic administration of budesonide ameliorates allergen-induced airway remodeling," Clin. Exp. Allergy, 35: 388-396 (2005), which is incorporated by reference in its entirety. Female Balb/c mice are divided into 3 groups: alum control group, test group, and vehicle control group. Airway inflammation and remodeling is induced in the test and vehicle control group mice sensitized with intraperitoneal administration of ovalbumin (OVA) at a concentration of 0.01 mg/mouse in 0.2 mL alum on days 0 and 12. Alum control mice receive the same volume of phosphate buffered saline (PBS) in alum. Prolonged inflammation is induced by subsequent exposure to aerosolized OVA (5%) three times a week for 20 minutes in the test and vehicle control mice until mice are sacrificed at various time points. After establishment of considerable lung eosinophilia and airway hyper-reactivity, test group mice are treated intraperitoneally with GML-X3 (1 mg/kg), and vehicle control mice with the same dose of vehicle alone (PBS). Mice are then sacrificed at week 2, week 4, week 6 and week 8.

Airway responsiveness is measured indirectly by whole body plethysmography to calculate the enhanced pause, as described in Hamelmann, E. et al., "Noninvasive measurement of airway responsiveness in allergic mice using barometric plethysmography. Am J Respir Crit Care Med. 1997 September; 156(3 Pt 1):766-75, which is incorporated by reference in its entirety. Pressure differences (box pressure signals) are measured between a main chamber of the plethysmograph box and a reference chamber. Mice are placed in the main chamber, and baseline readings are taken. Aerosolized PBS or methacholine in increasing concentrations (3 to 50 mg/ml) are nebulized through an inlet of the main chamber for 3 min, and readings are taken and averaged. Airway reactivity is expressed as fold increase for each concentration of methacoline as compared with PBS readings, and dose response curves are calculated for all groups of mice.

For quantification of pulmonary inflammation, bronchoalveolar lavage (BAL) is performed as described in McMillan et al. (2005). The airways of mice are lavaged with PBS via a tracheal cannula, the BAL fluid is centrifuged, the cells are pelleted, and differential cell counts are performed. Lung tissue histopathology is performed to evaluate the number and size of inflammatory foci with paraffin embedded lung tissue sections stained with hematoxylin/eosin (H&E).

Airway remodeling is assessed by determining the amount of extracellular matric (ECM) deposition in the lungs, as described in McMillan et al. (2005). Total peribronchiolar matrix deposition is assessed on Martius Scarlet Blue (MSB) stained sections. Cytokine profiles are analyzed from supernatants generated from homogenizing isolated lobes of lungs. Paired antibodies for murine interleukin-4 (IL-4), interferon-γ (IFN-γ), and active tumor growth factor-β1 (TGF-β1), IL-5 are used in standardalized sandwich ELISAs according to manufacturer's protocol.

Example 12

Effect of GML-X3 on Arthritic Pain

Six individuals with moderate to chronic arthritic pain were administered 10 drops of GML-X3 solution daily (about 0.5 mL of 25 mg/mL solution) for 7 days.

BC is a 60 year old man suffering from chronic hip pain, which limits his ability to walk, run and exercise. Most of the pain was eliminated within three days of administration of GML-X3 solution daily (about 0.5 mL of 25 mg/mL solution), and all pain was eliminated within seven days. BC has been physically active without medication.

JR is a 65 year old woman with hip pain, which limits her activity to do housework and shop. She has not danced in years. Most of the hip pain was eliminated within three days of administration of GML-X3 solution daily (about 0.5 mL of 25 mg/mL solution). JR has been able to walk distances, do housework, and even dance. Her physical stamina has returned so that she can dance throughout the evening.

RN is a 77 year old woman with generalized arthritis. She has pain in her back, knees and one shoulder. Most of the pain was eliminated within seven days of administration of GML-X3 solution daily (about 0.5 mL of 25 mg/mL solution).

AL is a 26 year old woman with pain all over her body especially her knees and back. She was relieved of most of her pain within three days of administration of GML-X3 solution daily (about 0.5 mL of 25 mg/mL solution). This was especially notable in her back, knees, and neck. Her normal sleep pattern returned that has given her more energy.

IM is a 76 year old woman with severe arthritic pain all over her body especially her back. She was relieved of most of her pain within three days of administration of GML-X3 solution daily (about 0.5 mL of 25 mg/mL solution). This was especially notable in her back and knees. She was able to eat and sleep better and felt more energetic. She attended the gym, did shopping, housework and was able to resume normal social life.

EM is a 86 year old woman with severe hip pain, which has limited her walking She was relieved of most of her pain within five days of administration of the GML-X3 solution. She was able to walk with ease.

Example 13

Effect iof GML-X3 on a Wound Healing Model in Rabbits

The effect of GML-X3 in wound healing in vivo is tested in a rabbit wound healing model based on the method described in Aksoy, B. et al., "A new experimental delayed wound healing model in rabbits," Eur. J. Dermatol., 19(6): 565-569 (2009), which is incorporated by reference in its entirety. Young adult rabbits are divided into two groups: a control untreated group and a treated group. A horizontal incision about 4 cm in length is made on the dorsal part of the torso in each animal of each group and skin flaps are raised in front of and behind this incision exposing the panniculus carnosus layer, which is resected, and the skin flaps returned and sutured. Following a three week healing period, a third degree burn injury is inflicted using hot metal plate on the healed flaps. In the treated group animals, the resulting wounds are treated with 0.5 mL of 25 mg/mL GML-X3 solution daily for 14 days, while the resulting wounds of the control group animals are treated with PBS alone. Histopathological examination is performed on scar samples after healing. The antioxidant capacity of GML-X3 to scavenge ROS is measured according to the method described in Schonfelder, U. et al., "Influence of selected wound dressings on PMN elastase in chronic wound fluid and their antioxidant potential in vitro," Biomaterials, 26: 6664-6673 (2005) using chemiluminescent antioxidant test kits for ROS containing Pholasin®.

Example 14

Effect on GML-X3 on Fluoroquinolone-Induced Tendon Toxicity

The effect of GML-X3 on fluoroquinolone-induced tendon toxicity is tested with primary cultures of rabbit tendon cells. Tenocytes are isolated from the Achilles tendons of young adult rabbits (about 4 months of age) and primary tenocyte cultures are maintained, as described in Pouzaud, F. et al., "Age-dependent effects on redox status, oxidative stress, mitochondrial activity and toxicity induced by fluoroquinolones on primary cultures on rabbit tendon cells,"

Comparative Biochemistry and Physiology, Part C, 143: 232-241 (2006), which is incorporated by reference in its entirety. Tenocytes obtained from each rabbit are seeded into 200 μl fresh culture medium in microtiter plates and kept at 37° C. for 24 hours. The tenocytes are incubated at 37° C. in a humidified atmosphere with 5% $CO_2$ as follows: an untreated control group with culture medium alone for 72 hours; an experimental fluoroquinolone-treated group with nalidixic acid, a fluoroquinolone, for 72 hours; an experimental fluoroquinolone- and GML-X3-treated group with nalidixic acid for 72 hours followed by GML-X3 for 24 hours; and an experimental GML-X3- and fluoroquinolone-treated group with GML-X3 for 24 hours and then with nalidixic acid for 72 hours.

Redox status of the tenocyte groups is monitored using an Alamar Blue® assay that uses a visible blue fluorogen probe resazurin as described in Pouzaud, F. et al., "Age-dependent effects on redox status, oxidative stress, mitochondrial activity and toxicity induced by fluoroquinolones on primary cultures on rabbit tendon cells," Comparative Biochemistry and Physiology, Part C, 143: 232-241 (2006). Alamar Blue® is added to each well and incubated at 37° C. for 12 hours. Intracellular fluorescence is detected using cold-light cytofluorometry with an excitation wavelength of 535 nm and an emission wavelength of 600 nm. ROS production is detected using 2',7'-dihydrodichlorofluorescein diacetate) (DCFH-DA) fluorogen probe. Inside the cell, DCFH-DA becomes converted to a fluorescent compound, 2',7'-dichlorofluorescein (DCF) on oxidation by ROS. For detection of ROS production, cells are incubated with DCFH-DA in phosphate-buffered saline for 20 minutes prior to incubation with nalidixic acid or GML-X3. The fluorescence intensity is analyzed using a cold-light cytofluorometer with an excitation wavelength of 485 nm and an emission wavelength of 535 nm.

Example 15

Effect of GML-X3 on Metal Alloy Particle-Induced Toxicity and Inflammatory Cytokines The effect of GML-X3 on metal alloy particle-induced toxicity is tested according to a modification of a method described in Dalal, A. et al., "Orthopedic implant cobalt-alloy particles produce greater toxicity and inflammatory cytokines than titanium alloy and zirconium alloy-based particles in vitro, in human osteoblasts, fibroblasts, and macrophages," J. Biomed. Mater. Res. Part A, 100A: 2147-2158 (2012), which is incorporated by reference in its entirety. Perimplant cell lines, such as a monocyet/macrophage cell line (e.g., THP-1), a fibroblast cell line, an osteoblast cell line, etc, are challenged with Co—Cr—Mo alloy wear debris particles produced by milling of implant alloy pieces. Average particle size is characterized by microscopy. Each challenged cell line is divided into two groups: untreated and GML-X3 treated. Cell viability of each group is assessed using a cell viability assay, such as a luciferase based cell viability assay. Particle-induced IL-1β, IL-6, IL-8, and TNF-α production by each cell line are assessed by Luminex multiplex array (Invitrogen). Redox status and ROS production of the tested cells can also be analyzed as described in Example 14.

Example 16

Effect of GML-X3 on Copper Ion Toxicity in a Mouse Fibroblast Model

Sustained release of copper (Cu) ions from Cu-containing intrauterine devices (CuIUD) is an effective means of contraception but the tissue surrounding the CuIUD is prone to Cu ion toxicity. Cu ion extracts from Cu-containing intrauterine devices are prepared according to the method described in Cao, B. et al., "Concentration-dependent cytotoxicity of copper ions on mouse fibroblasts in vitro: effects of copper ion release from TCu380A vs TCu220C intrauterine devices," Biomed. Microdevices 14: 709-720 (2012), which is incorporated by reference in its entirety. A fibroblast cell line is divided into several sample groups, which are respectively challenged with Cu ion extracts, or serial dilutions of a 100 μg/ml commercial standard cupric ion solution. Each sample group is subdivided randomly into untreated and GML-X3 treated groups. Cell viability is assessed with a cell viability assay. Redox status and ROS production of the tested cells can also be analyzed as described in Example 14.

Example 17

Effect of GML-X3 on Metal Particle-Induced Inflammation in a Murine Model

The effect of GML-X3 on particle-induced inflammation is tested using a murine air pouch model according to a modified method as described in Mao, X. et al., "Therapeutic potential of the proteasome inhibitor Bortezomib on titanium particle-induced inflammation in a murine model," Inflammation, 35(3): 905-912 (2012), which is incorporated by reference in its entirety. 6-week old Balb/c mice are quarantined for about 3 weeks, the dorsal skin (about 2 $cm^2$) shaved and sterilized with alcohol to provide the pouch site. 3 ml of filtered air is injected subcutaneously at a single site with a 5 ml syringe fitted with a 25-gauge needle. The air pouches are injected with 1 ml filtered air on alternate days to maintain pouch integrity. The mice are challenged with several commercial metal particles, e.g., titanium, cobalt, chromium, nickel, and aluminium. Six days after pouch formation, for each commercial metal particle tested, the mice are divided randomly into three groups: (1) control (0.2 ml PBS in saline); (2) metal (0.2 ml of 5% (w/v) metal particle suspension in saline); and (3) metal+GML-X3 (0.2 ml of 5% (w/v) metal particle suspension and 0.2 ml of 25 mg/ml GML-X3). The pouches of each group are injected with the respective solutions. The mice are euthanized 7 days after treatment and the pouch tissues are collected for analysis. Redox status and ROS production of the pouch tissue sample can also be analyzed according to a modification of the method described in Example 14, in which the pouch tissue is homogenized prior to analysis. Gene expression for inflammatory cytokines, such as TNF-α, IL-1β, NF-κB, etc. is analysed by quantitative polymerase chain reaction (qPCR) of total RNA isolated from the pouch tissue samples as described in Mao, X. et al., Inflammation, 35(3): 905-912 (2012), which is incorporated by reference in its entirety.

Example 18

Effect of GML-X3 on Atopic Keratoconjunctivitis (Chronic Conjunctivitis)

A 95 year old woman suffering from chronic conjunctivitis was administered 10 drops of GML-X3 solution daily (about 0.5 mL of 25 mg/mL solution) for 7 days. She obtained complete relief of symptoms within 5 days of treatment with GML-X3.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed:

1. An organo-metallic complex comprising a palladium component, a ruthenium component, a zinc component, a first organyl component comprising a hydrocarbon chain of from 2 to 20 carbon atoms, and a second organyl component comprising a non-polar aliphatic amino acid, polar uncharged amino acid, or a derivative thereof, wherein the first organyl component is a structural link between the palladium component and the zinc component and wherein the second organyl component is a structural link between the zinc component and the ruthenium component;
wherein the ruthenium component is not directly bonded to the first organyl component and the palladium component is not directly bonded to the second organyl component;
the complex being characterized by a charge transfer effective to denature, depolarize, or remove hydrogen peroxide from a site of inflammation in the presence of hyaluronic acid.

2. The complex according to claim 1, wherein the palladium component is a palladium complex.

3. The complex according to claim 1, wherein the ruthenium component is a ruthenium complex.

4. The complex according to claim 1, wherein the organyl component comprises lipoic acid or a derivative thereof, a fatty acid component or a derivative thereof, at least one amino acid component, or a combination thereof.

5. The complex according to claim 4, wherein the fatty acid component is linoleic acid or a derivative thereof.

6. The complex according to claim 4, wherein a first amino acid component comprises arginine.

7. The complex according to claim 6, wherein the arginine is linked to the fatty acid component, and wherein the fatty acid component is a linoleic acid.

8. The complex according to claim 7, wherein the arginine facilitates water solubility of the linoleic acid.

9. The complex according to claim 1, wherein the second organyl component is N-formyl methionine.

10. An organometallic complex of Formula I:

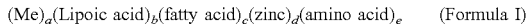

(Me)$_a$(Lipoic acid)$_b$(fatty acid)$_c$(zinc)$_d$(amino acid)$_e$  (Formula I)

wherein
Me signifies a metal;
the Me component contains a palladium component and a ruthenium component;
the lipoic acid component comprises lipoic acid or a derivative thereof, wherein the lipoic acid component comprises at least two sulfur atoms and at least one carboxyl group;
the fatty acid component comprises a hydrocarbon chain of from 2 to twenty carbon atoms wherein one end of the hydrocarbon chain (ω carbon) is a methyl group and at the other end (α carbon) is a carboxyl group; and
the zinc component is bonded to a methyl group at one end of the fatty acid component,
wherein
a is at least 2;
b, and c are each 1;
d is 0 or 1;
e is 1 or 2, and when e is 2, the amino acid component comprises a first amino acid and a second amino acid, wherein the first amino acid is bonded to the zinc component, and the second amino acid is bonded to the fatty acid component;
wherein the palladium component is bonded to the lipoic acid component via both sulfur atoms and by the carboxyl group oxygens of the lipoic acid component;
the fatty acid is bonded to the palladium via the carboxyl group of the fatty acid; and
the ruthenium component is bonded to the amino acid that is bonded to the zinc component;
wherein a Fourier Transform infrared spectrum of the complex comprises peaks at: 742 cm(−1), 965 cm(−1), 1034 cm(−1), 1356 cm(−1), 1402 cm(−1), 1604 cm(−1), 1668 cm(−1), 1958 cm(−1), 2921 cm(−1), and 3262 cm(−1);
the complex being characterized by a charge transfer effective to denature, depolarize, or remove hydrogen peroxide from a site of inflammation in the presence of hyaluronic acid.

11. The organometallic complex of claim 10, wherein the palladium component is elemental palladium or a palladium salt selected from the group consisting of palladium chloride, palladium bromide, palladium iodide, palladium nitrate, palladium oxide, palladium sulfide, or a combination thereof.

12. The organometallic complex of claim 10, wherein the ruthenium component is elemental ruthenium or a ruthenium salt selected from the group consisting of ruthenium chloride, ruthenium bromide, ruthenium iodide, ruthenium nitrate, ruthenium oxide, ruthenium sulfide, or a combination thereof.

13. The organometallic complex of claim 10, wherein the lipoic acid comprises a side group selected from a carboxyl, a sulfur, an amine or a combination thereof.

14. The organometallic complex of claim 13, wherein the lipoic acid derivative is lipoamide.

15. The organometallic complex of claim 10, wherein the fatty acid component is linoleic acid.

16. The organometallic complex of claim 10, wherein the fatty acid component is docosahexaenoic acid.

17. The organometallic complex of claim 10, wherein the zinc component is a form of zinc selected from elemental zinc, zinc carbonate, zinc gluconate, zinc chloride, zinc pyrithione, zinc sulfide, zinc methyl or zinc diethyl.

18. The organometallic complex of claim 10, wherein the first amino acid is formyl-methionine.

19. The organometallic complex of claim 10, wherein the second amino acid is arginine.

20. The organometallic complex of claim 10, wherein the complex further comprises at least one ligand, selected from an inorganic anionic ligand or a cationic ligand.

21. The organometallic complex of claim 20, wherein the inorganic anionic ligand is acetate, acetylacetonate, amine, ammonium chloride, ammonium nitrate, bromide, chloride, fluoride, iodide, nitrate, nitrite, oxalate, oxide, pyridine, sulfate or sulfide.

22. The organometallic complex of claim 20, wherein the cationic ligand selected from sodium, potassium, magnesium, calcium, ammonia, vanadate, molybdate, zinc, and tin.

23. The organometallic complex of claim 10, wherein the complex is thermodynamically stable.

24. The organometallic complex of claim 10, wherein an electron spin resonance spectrum of the complex with hyaluronic acid is associated with a hyperfine splitting constant at 10.34 Gauss.

25. A pharmaceutical composition comprising a therapeutic amount of a complex according to claim 10, and a pharmaceutically acceptable carrier.

26. The pharmaceutical composition of claim 25, wherein the complex is a solution or a dispersion.

27. The pharmaceutical composition of claim 26, wherein the complex is a solution, and wherein the complex in solution is present in an amount sufficient to obtain a concentration of about 5 mg/mL to 50 mg/mL.

28. The pharmaceutical composition of claim 25, wherein the composition is administered orally, enterally, parenterally, or topically.

29. A method of treating an inflammatory disease or condition in a mammal, comprising:
   (a) providing the therapeutic amount of the pharmaceutical composition according to claim 25; and
   (b) administering the therapeutic amount of the pharmaceutical composition to the mammal such that the therapeutic amount has at least one of the following effects:
      (i) an anti-inflammatory effect; and
      (ii) an anti-oxidant effect.

30. The method according to claim 29, wherein the inflammatory disease or condition is selected from the group consisting of an allergic condition, asthma, atopic dermatitis, atopic keratoconjunctivitis, angioedema, contact dermatitis, seborrheic dermatitis, rosacea, psoriasis, acne, an autoimmune disorder, an atherosclerotic condition, an arthritic condition, an inflammatory condition associated with a wound injury, a tendinopathy, an inflammatory condition associated with metal toxicity from an implantable device, or a combination thereof.

31. The method according to claim 29, wherein the inflammatory disease or condition is an allergic condition.

32. The method according to claim 31, wherein the allergic condition is allergic rhinitis.

33. The method according to claim 31, wherein the allergic condition is allergic conjunctivitis.

34. The method according to claim 29, wherein the inflammatory disease or condition is asthma.

35. The method according to claim 29, wherein the inflammatory disease or condition is atopic dermatitis.

36. The method according to claim 29, wherein the inflammatory disease or condition is atopic keratoconjunctivitis.

37. The method according to claim 29, wherein the inflammatory disease or condition is angioedema.

38. The method according to claim 29, wherein the inflammatory disease or condition is contact dermatitis.

39. The method according to claim 29, wherein the inflammatory disease or condition is seborrheic dermatitis.

40. The method according to claim 29, wherein the inflammatory disease or condition is rosacea.

41. The method according to claim 29, wherein the inflammatory disease or condition is psoriasis.

42. The method according to claim 29, wherein the inflammatory disease or condition is acne.

43. The method according to claim 29, wherein the inflammatory disease or condition is an autoimmune disorder.

44. The method according to claim 29, wherein the inflammatory disease or condition is an atherosclerotic condition.

45. The method according to claim 29, wherein the inflammatory disease or condition is an arthritic condition.

46. The method according to claim 29, wherein the inflammatory disease or condition is an inflammatory condition associated with a wound injury.

47. The method according to claim 29, wherein the inflammatory disease or condition is a tendinopathy.

48. The method according to claim 47, wherein the tendinopathy is a tendonitis.

49. The method according to claim 47, wherein the tendinopathy is a tendinosis.

50. The method according to claim 29, wherein the inflammatory disease or condition is an inflammatory condition associated with toxicity from a metal released from an implantable device.

51. The method according to claim 50, wherein the implantable device is selected from the group consisting of a surgical implant, a prosthetic device, a dental device, a metal containing contraception device, or a combination thereof.

52. The method according to claim 51, wherein the prosthetic device is selected from the group consisting of a prosthetic joint, a hip replacement device, a joint arthroplasty implant, a heart valve, or a combination thereof.

53. The method according to claim 51, wherein the surgical implant is selected from the group consisting of a plate, a rod, a screw, a stent, a pacemaker, a defibrillator, a catheter, or a combination thereof.

54. The method according to claim 51, wherein the metal containing contraception device is an intra-uterine device.

55. The method according to claim 50, wherein the metal is selected from the group consisting of copper, chromium, molybdenum, aluminium, vanadium, nickel, iron, titanium, or a combination thereof.

56. The method according to claim 50, wherein the metal is in a form selected from the group consisting of a metal particle, a metal ion, a metal oxide, a metal hydroxide, or a combination thereof.

57. The method according to claim 56, wherein the metal particle is at least 5 nm, at least 50 nm, or at least 500 nm in size.

58. The method according to claim 29, wherein the anti-inflammatory effect of the therapeutic amount is effective to reduce the level of at least one inflammatory mediator selected from the group consisting of TNF-$\alpha$, IL-1$\beta$, NF-$\kappa$B, IL-6, and IL-8, as compared to a normal control.

59. The method according to claim 29, wherein the anti-oxidant effect of the therapeutic amount is effective to increase the oxidation-reduction status of an affected cell, as compared to a normal control.

60. The method according to claim 29, wherein the anti-oxidant effect of the therapeutic amount is effective to reduce oxidative stress by reducing the level of at least one reactive oxygen species in an affected cell, as compared to a normal control.

61. The method according to claim 29, wherein the administering is parenterally, enterally, topically, transdermally, or nasally by inhalation.

* * * * *